(12) United States Patent
Stringer et al.

(10) Patent No.: US 11,208,639 B2
(45) Date of Patent: Dec. 28, 2021

(54) POLYPEPTIDES HAVING DNASE ACTIVITY

(71) Applicant: Novozymes A/S, Bagsvaerd (DK)

(72) Inventors: Mary Ann Stringer, Bagsvaerd (DK); Jesper Salomon, Holte (DK); Klaus Gori, Dyssegaard (DK); Jürgen Carsten Franz Knötzel, Copenhagen (DK)

(73) Assignee: Novozymes A/S, Bagsvaerd (DK)

( * ) Notice: Subject to any disclaimer, the term of this patent is extended or adjusted under 35 U.S.C. 154(b) by 1 day.

(21) Appl. No.: 16/495,151

(22) PCT Filed: Mar. 23, 2018

(86) PCT No.: PCT/EP2018/057472
§ 371 (c)(1),
(2) Date: Sep. 18, 2019

(87) PCT Pub. No.: WO2018/177938
PCT Pub. Date: Oct. 4, 2018

(65) Prior Publication Data
US 2020/0109381 A1 Apr. 9, 2020

(30) Foreign Application Priority Data

Mar. 31, 2017 (EP) ..................................... 17164331
Jul. 7, 2017 (EP) ..................................... 17180194

(51) Int. Cl.
*C12N 9/22* (2006.01)
*C11D 3/386* (2006.01)
*C11D 11/00* (2006.01)

(52) U.S. Cl.
CPC ................ *C12N 9/22* (2013.01); *C11D 3/386* (2013.01); *C11D 11/0017* (2013.01)

(58) Field of Classification Search
None
See application file for complete search history.

(56) References Cited

FOREIGN PATENT DOCUMENTS

| EP | 2617824 A1 | 7/2013 |
| EP | 3088505 A1 | 11/2016 |
| WO | 2014087011 A1 | 6/2014 |
| WO | 2015155350 A1 | 10/2015 |
| WO | WO 2015/155351 | * 10/2015 |
| WO | 2017001472 A1 | 1/2017 |

OTHER PUBLICATIONS

Wibberg et al., "Establishment and interpretation of the genome sequence of the phytopathogenic fungus Rhizoctonia solani AG1-IB isolate Jul. 3, 2014", J. Biotechnology, 2013, vol. 167, No. 2, pp. 142-155. doi: 10.1016/j.jbiotec.2012.12.010.*
UniProt A0A0K6GHI4_9AGAM, deposited Nov. 11, 2015. Retrived from < https://www.uniprot.org/uniprot/A0A0K6GHI4 >.*
UniProt M5C218_THACB, deposited May 29, 2013. Retrived from < https://www.uniprot.org/uniprot/M5C218 >.*
Pfam DUF1524 (PF07510) family—Retrieved from EMBL-EBI on Aug. 16, 2021 < https://pfam.xfam.org/family/PF07510#tabview=tab 1 >.*
Kohler et al, 2015, EBI Accession No. A0A0D2KRL1.
Kuo et al, 2015, EBI Accession No. A0A0C3C1D2_HEBCY.
Min et al, 2016, EBI Accession No. A0A151VWF3.
Noorani, 2015, EBI Accession No. A0A0K6FXN0.

* cited by examiner

*Primary Examiner* — Suzanne M Noakes
(74) *Attorney, Agent, or Firm* — Yoshimi Barron

(57) ABSTRACT

The present invention relates to polypeptides having DNase activity and polynucleotides encoding the polypeptides. The invention also relates to nucleic acid constructs, vectors, and host cells comprising the polynucleotides as well as methods of producing and using the polypeptides.

Figure 2:
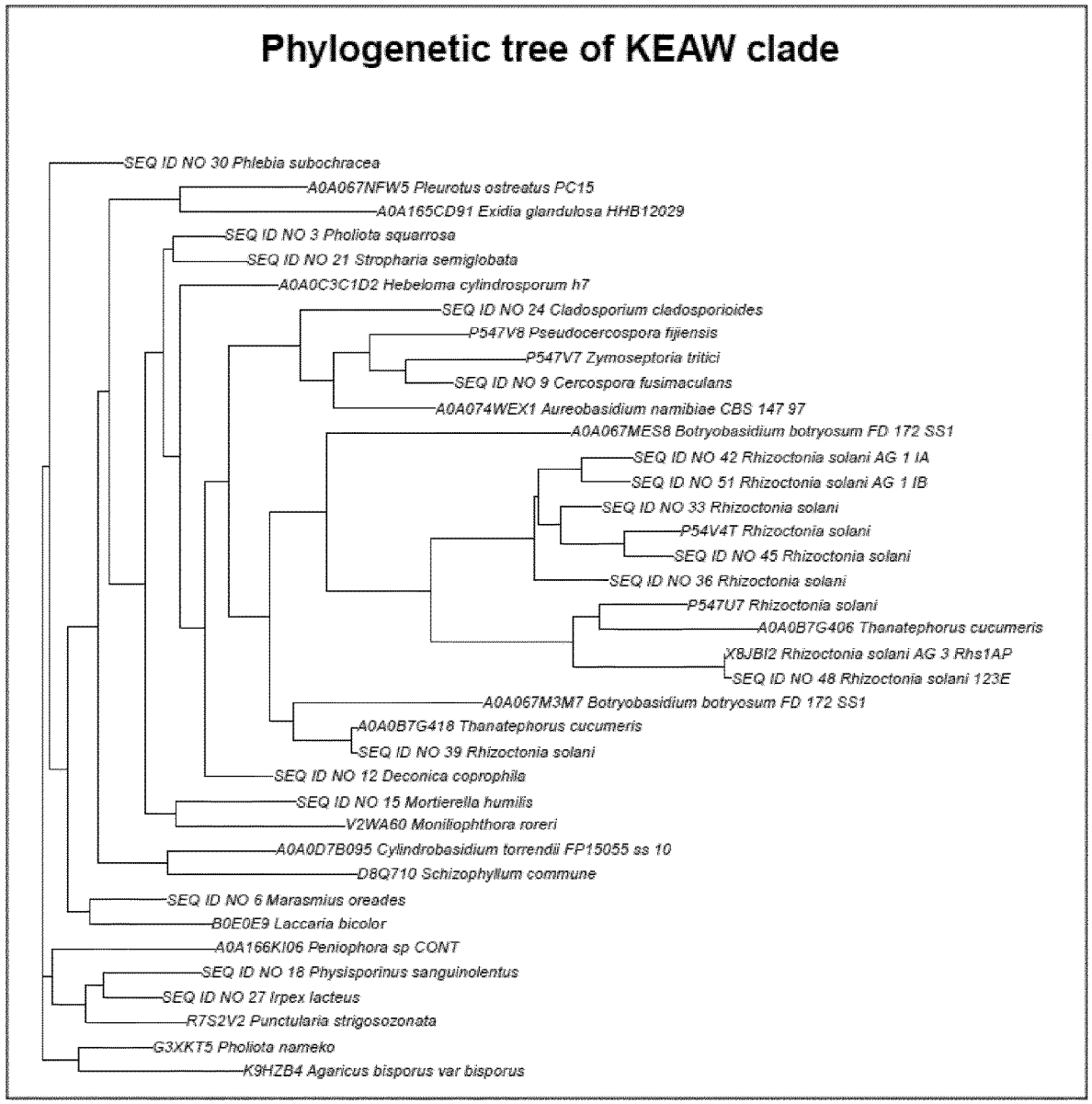

25 Claims, 5 Drawing Sheets
Specification includes a Sequence Listing.

```
                        SEQUENCE LISTING

<160> NUMBER OF SEQ ID NOS: 57

<210> SEQ ID NO 1
<211> LENGTH: 1091
<212> TYPE: DNA
<213> ORGANISM: Pholiota squarrosa
<220> FEATURE:
<221> NAME/KEY: CDS
<222> LOCATION: (1)..(127)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1088)
<220> FEATURE:
<221> NAME/KEY: CDS
<222> LOCATION: (190)..(255)
<220> FEATURE:
<221> NAME/KEY: CDS
<222> LOCATION: (326)..(352)
<220> FEATURE:
<221> NAME/KEY: CDS
<222> LOCATION: (434)..(552)
<220> FEATURE:
<221> NAME/KEY: CDS
<222> LOCATION: (638)..(756)
<220> FEATURE:
<221> NAME/KEY: CDS
<222> LOCATION: (864)..(880)
<220> FEATURE:
<221> NAME/KEY: CDS
<222> LOCATION: (943)..(1088)

<400> SEQUENCE: 1 atg cac ttc tcc acc gcg ttc gtc tct ctc ctc ctc gct gca cct gct      48
Met His Phe Ser Thr Ala Phe Val Ser Leu Leu Leu Ala Ala Pro Ala
            -15                 -10                  -5 gcc ttg ggc gcc gcc atc gag tcg cgc gcc ctg ccc acc ccc gtc agt      96
Ala Leu Gly Ala Ala Ile Glu Ser Arg Ala Leu Pro Thr Pro Val Ser
     -1   1                 5                  10 gcg gcc act gcg agg acc tat ctt gct gcc t gtacgtatga tgctgacgca     147
Ala Ala Thr Ala Arg Thr Tyr Leu Ala Ala
         15                  20 agcgcctatg tatttgtgct gaacgtatac tacttacttt ag tg  act gtc gcc     200
                                                 Leu Thr Val Ala
                                                          25 gcc gag tcc aac tca ccc gcg tac gac cgt gac ctt ttc aac cat tgg      248
Ala Glu Ser Asn Ser Pro Ala Tyr Asp Arg Asp Leu Phe Asn His Trp
         30                  35                  40 atc acc a gtgcgtcgcc tctttcggag tctctatctc gtccaaatgt tatcgcgcta    305
Ile Thr
    45 aaccacttcg atgattatag tc  tcc ggc tcg tgc aac acc cgc gag a          352
                         Ile Ser Gly Ser Cys Asn Thr Arg Glu
                                         50 gtgcgtccta cctctttccc aaccccgat cctttttaaag tacaaggttg accaatgtat    412 ctgttctgtt ataccacaca g cc  gtc ctc aag cgc gac ggc acc agc gtc      462
                            Thr Val Leu Lys Arg Asp Gly Thr Ser Val
```

```
                  55                  60
gtc gtc gac tcc agc tgc gcg tcc acg tcg ggc cac tgg gtg tcg ccc      510
Val Val Asp Ser Ser Cys Ala Ser Thr Ser Gly His Trp Val Ser Pro
 65                  70                  75                  80 tac gac aac gtc gcc acc acg ctt gcg agc gac ctc gac atc              552
Tyr Asp Asn Val Ala Thr Thr Leu Ala Ser Asp Leu Asp Ile
                 85                  90 gtgagtactt tcgattttc atactcttgt tcagttatac aattatattt atgttgtttt     612 ttatttttt tatttttgtg tttag gac cac ctc gtc cct ctg aaa gaa gcc       664
                            Asp His Leu Val Pro Leu Lys Glu Ala
                             95                 100 tgg gtc tcc ggt gcg cgt ctg tgg acg aac gca cag cgc gag gca ttc      712
Trp Val Ser Gly Ala Arg Leu Trp Thr Asn Ala Gln Arg Glu Ala Phe
    105                 110                 115 gcg aat gac ctt acg cgc ccg cag ctt gtc gct gtt act gac aa           756
Ala Asn Asp Leu Thr Arg Pro Gln Leu Val Ala Val Thr Asp Asn
120                 125                 130 gtaagtacac gttttccctg ttagtgggct aatcccaaca cacacgct gacctactgt      816 ttcccctacc atcactccca cttcgcttcc tttaattcca ttgacag c ctc aac caa    873
                                                    Leu Asn Gln
                                                            135 gcc aaa g gtccgcctct acttctcgcg ctccactgac actgacacgt atacgtatat     930
Ala Lys ttatttgtgt ag gc  gac caa gac ccc gcg gaa tgg atg ccc cca ctc gcg    980
                  Gly Asp Gln Asp Pro Ala Glu Trp Met Pro Pro Leu Ala
                                 140                 145                 150 agc tac cgc tgc acc tac gtg cgc gcg tgg gtc cag gtt aaa tat tat     1028
Ser Tyr Arg Cys Thr Tyr Val Arg Ala Trp Val Gln Val Lys Tyr Tyr
    155                 160                 165 tat ggc ctt agc gtg gac agt gcg gag aag gct gcg ctt acg agc tat     1076
Tyr Gly Leu Ser Val Asp Ser Ala Glu Lys Ala Ala Leu Thr Ser Tyr
170                 175                 180 ttg tct ggg tgt tag                                                 1091
Leu Ser Gly Cys
185

<210> SEQ ID NO 2
<211> LENGTH: 207
<212> TYPE: PRT
<213> ORGANISM: Pholiota squarrosa

<400> SEQUENCE: 2

Met His Phe Ser Thr Ala Phe Val Ser Leu Leu Ala Ala Pro Ala
                -15                 -10                  -5

Ala Leu Gly Ala Ala Ile Glu Ser Arg Ala Leu Pro Thr Pro Val Ser
         -1   1               5                  10

Ala Ala Thr Ala Arg Thr Tyr Leu Ala Ala Leu Thr Val Ala Ala Glu
         15                  20                  25

Ser Asn Ser Pro Ala Tyr Asp Arg Asp Leu Phe Asn His Trp Ile Thr
 30                  35                  40                  45

Ile Ser Gly Ser Cys Asn Thr Arg Glu Thr Val Leu Lys Arg Asp Gly
                 50                  55                  60

Thr Ser Val Val Asp Ser Ser Cys Ala Ser Thr Ser Gly His Trp
                 65                  70                  75

Val Ser Pro Tyr Asp Asn Val Ala Thr Thr Leu Ala Ser Asp Leu Asp
             80                  85                  90

Ile Asp His Leu Val Pro Leu Lys Glu Ala Trp Val Ser Gly Ala Arg
```

```
                95                 100                 105
Leu Trp Thr Asn Ala Gln Arg Glu Ala Phe Ala Asn Asp Leu Thr Arg
110                 115                 120                 125

Pro Gln Leu Val Ala Val Thr Asp Asn Leu Asn Gln Ala Lys Gly Asp
                130                 135                 140

Gln Asp Pro Ala Glu Trp Met Pro Pro Leu Ala Ser Tyr Arg Cys Thr
            145                 150                 155

Tyr Val Arg Ala Trp Val Gln Val Lys Tyr Tyr Tyr Gly Leu Ser Val
        160                 165                 170

Asp Ser Ala Glu Lys Ala Ala Leu Thr Ser Tyr Leu Ser Gly Cys
    175                 180                 185

<210> SEQ ID NO 3
<211> LENGTH: 188
<212> TYPE: PRT
<213> ORGANISM: Pholiota squarrosa

<400> SEQUENCE: 3

Ala Ala Ile Glu Ser Arg Ala Leu Pro Thr Pro Val Ser Ala Ala Thr
1               5                  10                 15

Ala Arg Thr Tyr Leu Ala Ala Leu Thr Val Ala Ala Glu Ser Asn Ser
            20                  25                  30

Pro Ala Tyr Asp Arg Asp Leu Phe Asn His Trp Ile Thr Ile Ser Gly
        35                  40                  45

Ser Cys Asn Thr Arg Glu Thr Val Leu Lys Arg Asp Gly Thr Ser Val
    50                  55                  60

Val Val Asp Ser Ser Cys Ala Ser Thr Ser Gly His Trp Val Ser Pro
65                  70                  75                  80

Tyr Asp Asn Val Ala Thr Thr Leu Ala Ser Asp Leu Asp Ile Asp His
                85                  90                  95

Leu Val Pro Leu Lys Glu Ala Trp Val Ser Gly Ala Arg Leu Trp Thr
            100                 105                 110

Asn Ala Gln Arg Glu Ala Phe Ala Asn Asp Leu Thr Arg Pro Gln Leu
        115                 120                 125

Val Ala Val Thr Asp Asn Leu Asn Gln Ala Lys Gly Asp Gln Asp Pro
    130                 135                 140

Ala Glu Trp Met Pro Pro Leu Ala Ser Tyr Arg Cys Thr Tyr Val Arg
145                 150                 155                 160

Ala Trp Val Gln Val Lys Tyr Tyr Tyr Gly Leu Ser Val Asp Ser Ala
                165                 170                 175

Glu Lys Ala Ala Leu Thr Ser Tyr Leu Ser Gly Cys
            180                 185

<210> SEQ ID NO 4
<211> LENGTH: 1150
<212> TYPE: DNA
<213> ORGANISM: Marasmius oreades
<220> FEATURE:
<221> NAME/KEY: CDS
<222> LOCATION: (1)..(103)
<220> FEATURE:
<221> NAME/KEY: sig_peptide
<222> LOCATION: (1)..(51)
<220> FEATURE:
<221> NAME/KEY: mat_peptide
<222> LOCATION: (52)..(1147)
<220> FEATURE:
<221> NAME/KEY: CDS
<222> LOCATION: (170)..(235)
<220> FEATURE:
```

```
<221> NAME/KEY: CDS
<222> LOCATION: (288)..(314)
<220> FEATURE:
<221> NAME/KEY: CDS
<222> LOCATION: (378)..(402)
<220> FEATURE:
<221> NAME/KEY: CDS
<222> LOCATION: (480)..(573)
<220> FEATURE:
<221> NAME/KEY: CDS
<222> LOCATION: (637)..(660)
<220> FEATURE:
<221> NAME/KEY: CDS
<222> LOCATION: (715)..(777)
<220> FEATURE:
<221> NAME/KEY: CDS
<222> LOCATION: (836)..(884)
<220> FEATURE:
<221> NAME/KEY: CDS
<222> LOCATION: (949)..(957)
<220> FEATURE:
<221> NAME/KEY: CDS
<222> LOCATION: (1011)..(1147)

<400> SEQUENCE: 4
```

```
atg tta ctg caa gcc gtt gtt gtc ttt ggt gcc ctt ggg act gct ctt        48
Met Leu Leu Gln Ala Val Val Val Phe Gly Ala Leu Gly Thr Ala Leu
        -15                 -10                  -5 gcc gct ctc cct act cct gtt aca gct gcc acc gct cgg acg tac ttg        96
Ala Ala Leu Pro Thr Pro Val Thr Ala Ala Thr Ala Arg Thr Tyr Leu
 -1  1               5                  10                  15 tct gag c gtcagtcgtt tcttgtttcc aattcccagc gatcccttct catctctgtt      153
Ser Glu gtgtatgtct ctttag tg  act gtc gcg gcc gaa tcc aac gtt ccc gct tat     204
                      Leu Thr Val Ala Ala Glu Ser Asn Val Pro Ala Tyr
                              20                  25 tcg agg gat ctg ttc aag act tgg gat att a gtgcgtcgcg cttcctagcg       255
Ser Arg Asp Leu Phe Lys Thr Trp Asp Ile
 30              35 cccacatagt cactcgttga gatatgttat ag tc  tct ggg act tgt gat act       307
                                        Ile Ser Gly Thr Cys Asp Thr
                                              40                  45 cgc gaa a gtaagtgttt cccgcttgaa atattcctac ccgtcaacga tcactcatcg      364
Arg Glu actgattttc tag ct  gtc cta ata cgt gat ggg acg aa  gtacgtcttc         412
                   Thr Val Leu Ile Arg Asp Gly Thr Asn
                           50                  55 tcttttcttc gttcgattca acgtgtcgtt aaatttgaat ttttaattct ttcattgtga     472 aaaacag c gtt gtg act gac agc tcg tgc aaa gct acc gcc ggt cac tgg     522
          Val Val Thr Asp Ser Ser Cys Lys Ala Thr Ala Gly His Trp
                      60                  65                  70 gtt tca ccc tat gac gct gta gcc acg act ttg gct agc gat tta gat       570
Val Ser Pro Tyr Asp Ala Val Ala Thr Thr Leu Ala Ser Asp Leu Asp
             75                  80                  85 att gtccgtcttt ttttctattg cagctatgtc tacgatggca tgttgaaacc            623
Ile tcgctgtttt tag gat cac ctc gtt cct ttg aag gaa gtacgtcttt             670
                Asp His Leu Val Pro Leu Lys Glu
                         90                  95 caatgaatct cctcgtcaat tccaatatta aggatgcgtt ttag gca tgg gtc tcg      726
                                                   Ala Trp Val Ser
                                                               100 ggg gct aga ttg tgg act gat gct cag agg gag gca ttt gca aat gac       774
Gly Ala Arg Leu Trp Thr Asp Ala Gln Arg Glu Ala Phe Ala Asn Asp
```

```
                    105                 110                 115
ttg gtatggattt catcactctt tcagataaga atgtctcctc aacgatccgg           827
Leu atgaacag aca cgt ccg caa ctt gtc gcc gtc acg gat aat ctg aac gaa    877
         Thr Arg Pro Gln Leu Val Ala Val Thr Asp Asn Leu Asn Glu
             120                 125                 130 tct aag g gtatggtgtt tatcatttta gccttttgt gtttctcaag tacaagtgtt     934
Ser Lys cgtttgctgt tcag gt  gac caa g gtgcgttctc gggctgccgg tactgtgaga      987
                Gly Asp Gln
                    135 atggagattg aataactaat gag at  gtc gct aat tgg gtt cct cca ctc gcg   1039
                              Asp Val Ala Asn Trp Val Pro Pro Leu Ala
                                      140                 145 agc tac gtc tgc acc tac gta cgg gca tgg gtg acc gtg aag cat ttt     1087
Ser Tyr Val Cys Thr Tyr Val Arg Ala Trp Val Thr Val Lys His Phe
            150                 155                 160 tac aag ctt tca gtc gat tct gtg gag aag acg gct ctt caa aat tat     1135
Tyr Lys Leu Ser Val Asp Ser Val Glu Lys Thr Ala Leu Gln Asn Tyr
        165                 170                 175 ctg gca aac tgt tga                                                  1150
Leu Ala Asn Cys
    180

<210> SEQ ID NO 5
<211> LENGTH: 199
<212> TYPE: PRT
<213> ORGANISM: Marasmius oreades

<400> SEQUENCE: 5

Met Leu Leu Gln Ala Val Val Phe Gly Ala Leu Gly Thr Ala Leu
        -15                 -10                  -5

Ala Ala Leu Pro Thr Pro Val Thr Ala Ala Thr Ala Arg Thr Tyr Leu
 -1  1              5                  10                  15

Ser Glu Leu Thr Val Ala Ala Glu Ser Asn Val Pro Ala Tyr Ser Arg
                20                  25                  30

Asp Leu Phe Lys Thr Trp Asp Ile Ile Ser Gly Thr Cys Asp Thr Arg
            35                  40                  45

Glu Thr Val Leu Ile Arg Asp Gly Thr Asn Val Val Thr Asp Ser Ser
        50                  55                  60

Cys Lys Ala Thr Ala Gly His Trp Val Ser Pro Tyr Asp Ala Val Ala
    65                  70                  75

Thr Thr Leu Ala Ser Asp Leu Asp Ile Asp His Leu Val Pro Leu Lys
80                  85                  90                  95

Glu Ala Trp Val Ser Gly Ala Arg Leu Trp Thr Asp Ala Gln Arg Glu
                100                 105                 110

Ala Phe Ala Asn Asp Leu Thr Arg Pro Gln Leu Val Ala Val Thr Asp
            115                 120                 125

Asn Leu Asn Glu Ser Lys Gly Asp Gln Asp Val Ala Asn Trp Val Pro
        130                 135                 140

Pro Leu Ala Ser Tyr Val Cys Thr Tyr Val Arg Ala Trp Val Thr Val
    145                 150                 155

Lys His Phe Tyr Lys Leu Ser Val Asp Ser Val Glu Lys Thr Ala Leu
160                 165                 170                 175

Gln Asn Tyr Leu Ala Asn Cys
            180
```

<210> SEQ ID NO 6
<211> LENGTH: 182
<212> TYPE: PRT
<213> ORGANISM: Marasmius oreades

<400> SEQUENCE: 6

```
Ala Leu Pro Thr Pro Val Thr Ala Ala Thr Ala Arg Thr Tyr Leu Ser
1               5                   10                  15

Glu Leu Thr Val Ala Ala Glu Ser Asn Val Pro Ala Tyr Ser Arg Asp
            20                  25                  30

Leu Phe Lys Thr Trp Asp Ile Ile Ser Gly Thr Cys Asp Thr Arg Glu
        35                  40                  45

Thr Val Leu Ile Arg Asp Gly Thr Asn Val Val Thr Asp Ser Ser Cys
    50                  55                  60

Lys Ala Thr Ala Gly His Trp Val Ser Pro Tyr Asp Ala Val Ala Thr
65                  70                  75                  80

Thr Leu Ala Ser Asp Leu Asp Ile Asp His Leu Val Pro Leu Lys Glu
                85                  90                  95

Ala Trp Val Ser Gly Ala Arg Leu Trp Thr Asp Ala Gln Arg Glu Ala
            100                 105                 110

Phe Ala Asn Asp Leu Thr Arg Pro Gln Leu Val Ala Val Thr Asp Asn
        115                 120                 125

Leu Asn Glu Ser Lys Gly Asp Gln Asp Val Ala Asn Trp Val Pro Pro
    130                 135                 140

Leu Ala Ser Tyr Val Cys Thr Tyr Val Arg Ala Trp Val Thr Val Lys
145                 150                 155                 160

His Phe Tyr Lys Leu Ser Val Asp Ser Val Glu Lys Thr Ala Leu Gln
                165                 170                 175

Asn Tyr Leu Ala Asn Cys
            180
```

<210> SEQ ID NO 7
<211> LENGTH: 682
<212> TYPE: DNA
<213> ORGANISM: Cercospora fusimaculans
<220> FEATURE:
<221> NAME/KEY: CDS
<222> LOCATION: (1)..(425)
<220> FEATURE:
<221> NAME/KEY: sig_peptide
<222> LOCATION: (1)..(45)
<220> FEATURE:
<221> NAME/KEY: mat_peptide
<222> LOCATION: (46)..(679)
<220> FEATURE:
<221> NAME/KEY: CDS
<222> LOCATION: (481)..(679)

<400> SEQUENCE: 7

```
atg aag tcc gcc ctt ctc gtc gct ctg gcc gtt ggc gct att gcc gca    48
Met Lys Ser Ala Leu Leu Val Ala Leu Ala Val Gly Ala Ile Ala Ala
-15                 -10                 -5                  -1  1 ccc agt cac ttc gaa gtc gtt aag aga ggc aat ctc cca aca cca gtc    96
Pro Ser His Phe Glu Val Val Lys Arg Gly Asn Leu Pro Thr Pro Val
        5                   10                  15 tct gcc gca aca gct cga tcc tac ttg agc cag atc ccc acg gaa gcc   144
Ser Ala Ala Thr Ala Arg Ser Tyr Leu Ser Gln Ile Pro Thr Glu Ala
    20                  25                  30 gag aac aac agc cct gca tac aat cgc gac ctc ttc aat cat tgg atc   192
Glu Asn Asn Ser Pro Ala Tyr Asn Arg Asp Leu Phe Asn His Trp Ile
35                  40                  45
```

```
aca atc tct ggt cgg tgc aac acg cgt gaa gaa gtc ctc aaa cgc gat    240
Thr Ile Ser Gly Arg Cys Asn Thr Arg Glu Glu Val Leu Lys Arg Asp
 50                  55                  60                  65 ggc tcc aat gtc gtg acc gac agt gag tgt cga gcg act tcg ggt tct    288
Gly Ser Asn Val Val Thr Asp Ser Glu Cys Arg Ala Thr Ser Gly Ser
                 70                  75                  80 tgg tac tcc gac tac gac ggc gcg aca tgg acc cta gcg tcc gat gtt    336
Trp Tyr Ser Asp Tyr Asp Gly Ala Thr Trp Thr Leu Ala Ser Asp Val
             85                  90                  95 gac atc gat cat att gtt cca ctg aga gaa gcc tgg gtt tct ggt gct    384
Asp Ile Asp His Ile Val Pro Leu Arg Glu Ala Trp Val Ser Gly Ala
        100                 105                 110 cgt aat tgg gat tct gcg aag cga caa cag ttt gcc aat ga             425
Arg Asn Trp Asp Ser Ala Lys Arg Gln Gln Phe Ala Asn Asp
    115                 120                 125 gtgagtaaag tggatattca tcagtgcatt cgttttctat gctcaaactc tctag t     481 ctc acg cgt ccg cag ctc ctc gct gtc acc gac agc gtc aac caa ggc    529
Leu Thr Arg Pro Gln Leu Leu Ala Val Thr Asp Ser Val Asn Gln Gly
            130                 135                 140 aag ggc gat cag gat cct gcc gag tgg ctg ccc agc cga act gcc tac    577
Lys Gly Asp Gln Asp Pro Ala Glu Trp Leu Pro Ser Arg Thr Ala Tyr
145                 150                 155 cga tgc aca tac gtg cga gcc tgg act cag gtc aag tac tac tat ggt    625
Arg Cys Thr Tyr Val Arg Ala Trp Thr Gln Val Lys Tyr Tyr Tyr Gly
160                 165                 170                 175 ctg agc atg gac agt gcc gag aag tcg gct gtc agc aat atc ttg aac    673
Leu Ser Met Asp Ser Ala Glu Lys Ser Ala Val Ser Asn Ile Leu Asn
                180                 185                 190 gga tgc tag                                                        682
Gly Cys

<210> SEQ ID NO 8
<211> LENGTH: 208
<212> TYPE: PRT
<213> ORGANISM: Cercospora fusimaculans

<400> SEQUENCE: 8

Met Lys Ser Ala Leu Leu Val Ala Leu Ala Val Gly Ala Ile Ala Ala
-15                 -10                  -5                 -1  1

Pro Ser His Phe Glu Val Val Lys Arg Gly Asn Leu Pro Thr Pro Val
             5                  10                  15

Ser Ala Ala Thr Ala Arg Ser Tyr Leu Ser Gln Ile Pro Thr Glu Ala
         20                  25                  30

Glu Asn Asn Ser Pro Ala Tyr Asn Arg Asp Leu Phe Asn His Trp Ile
     35                  40                  45

Thr Ile Ser Gly Arg Cys Asn Thr Arg Glu Glu Val Leu Lys Arg Asp
 50                  55                  60                  65

Gly Ser Asn Val Val Thr Asp Ser Glu Cys Arg Ala Thr Ser Gly Ser
                 70                  75                  80

Trp Tyr Ser Asp Tyr Asp Gly Ala Thr Trp Thr Leu Ala Ser Asp Val
             85                  90                  95

Asp Ile Asp His Ile Val Pro Leu Arg Glu Ala Trp Val Ser Gly Ala
        100                 105                 110

Arg Asn Trp Asp Ser Ala Lys Arg Gln Gln Phe Ala Asn Asp Leu Thr
    115                 120                 125

Arg Pro Gln Leu Leu Ala Val Thr Asp Ser Val Asn Gln Gly Lys Gly
130                 135                 140                 145
```

```
Asp Gln Asp Pro Ala Glu Trp Leu Pro Ser Arg Thr Ala Tyr Arg Cys
            150                 155                 160

Thr Tyr Val Arg Ala Trp Thr Gln Val Lys Tyr Tyr Gly Leu Ser
        165                 170                 175

Met Asp Ser Ala Glu Lys Ser Ala Val Ser Asn Ile Leu Asn Gly Cys
        180                 185                 190

<210> SEQ ID NO 9
<211> LENGTH: 193
<212> TYPE: PRT
<213> ORGANISM: Cercospora fusimaculans

<400> SEQUENCE: 9

Ala Pro Ser His Phe Glu Val Val Lys Arg Gly Asn Leu Pro Thr Pro
1               5                   10                  15

Val Ser Ala Ala Thr Ala Arg Ser Tyr Leu Ser Gln Ile Pro Thr Glu
            20                  25                  30

Ala Glu Asn Asn Ser Pro Ala Tyr Asn Arg Asp Leu Phe Asn His Trp
        35                  40                  45

Ile Thr Ile Ser Gly Arg Cys Asn Thr Arg Glu Glu Val Leu Lys Arg
50                  55                  60

Asp Gly Ser Asn Val Val Thr Asp Ser Glu Cys Arg Ala Thr Ser Gly
65                  70                  75                  80

Ser Trp Tyr Ser Asp Tyr Asp Gly Ala Thr Trp Thr Leu Ala Ser Asp
                85                  90                  95

Val Asp Ile Asp His Ile Val Pro Leu Arg Glu Ala Trp Val Ser Gly
            100                 105                 110

Ala Arg Asn Trp Asp Ser Ala Lys Arg Gln Gln Phe Ala Asn Asp Leu
        115                 120                 125

Thr Arg Pro Gln Leu Leu Ala Val Thr Asp Ser Val Asn Gln Gly Lys
    130                 135                 140

Gly Asp Gln Asp Pro Ala Glu Trp Leu Pro Ser Arg Thr Ala Tyr Arg
145                 150                 155                 160

Cys Thr Tyr Val Arg Ala Trp Thr Gln Val Lys Tyr Tyr Gly Leu
                165                 170                 175

Ser Met Asp Ser Ala Glu Lys Ser Ala Val Ser Asn Ile Leu Asn Gly
            180                 185                 190

Cys

<210> SEQ ID NO 10
<211> LENGTH: 956
<212> TYPE: DNA
<213> ORGANISM: Deconica coprophila
<220> FEATURE:
<221> NAME/KEY: CDS
<222> LOCATION: (1)..(118)
<220> FEATURE:
<221> NAME/KEY: sig_peptide
<222> LOCATION: (1)..(51)
<220> FEATURE:
<221> NAME/KEY: mat_peptide
<222> LOCATION: (52)..(953)
<220> FEATURE:
<221> NAME/KEY: CDS
<222> LOCATION: (178)..(243)
<220> FEATURE:
<221> NAME/KEY: CDS
<222> LOCATION: (308)..(334)
<220> FEATURE:
<221> NAME/KEY: CDS
<222> LOCATION: (385)..(503)
```

<220> FEATURE:
<221> NAME/KEY: CDS
<222> LOCATION: (559)..(677)
<220> FEATURE:
<221> NAME/KEY: CDS
<222> LOCATION: (737)..(762)
<220> FEATURE:
<221> NAME/KEY: CDS
<222> LOCATION: (817)..(953)

<400> SEQUENCE: 10

```
atg cgc gtc tcg gtc gtc tcc ctc ctt gct ctg gtc tcc gcc gca act      48
Met Arg Val Ser Val Val Ser Leu Leu Ala Leu Val Ser Ala Ala Thr
    -15             -10                 -5 gct tca gtg ttg cct cgt gcg ctc cca acg ccc gtt agt gcc gcc acc      96
Ala Ser Val Leu Pro Arg Ala Leu Pro Thr Pro Val Ser Ala Ala Thr
 -1  1               5                  10                  15 gca aag aca tac ctt gcc agc t gtacgtgctc ctccatttga gcggatctgc      148
Ala Lys Thr Tyr Leu Ala Ser
                20 acactcttat gcttatatt catttttag tg  aag gtt gag gct gag tct aac       200
                                   Lys Val Glu Ala Glu Ser Asn
                                    25                  30 tcc ccc gcg tac aac cgt gac ctc ttc aac cac tgg att act a            243
Ser Pro Ala Tyr Asn Arg Asp Leu Phe Asn His Trp Ile Thr
            35                  40 gtaaaagaa gtcccagctg tcactctctc ccaaccctac tgactcgcgt ctcttatctg     303 ccag tc tct ggc tca tgc aac act cgc gag a gtgagattac cgtcttttgt     354
     Ile Ser Gly Ser Cys Asn Thr Arg Glu
         45                  50 ctattatatt tgccgctaat agatatatag ct gtc ttg aag cgc gac gga act      407
                                   Thr Val Leu Lys Arg Asp Gly Thr
                                        55                  60 agc gtc gtt act gac tct gct tgc gca tcg aca tcc ggc aaa tgg gtc      455
Ser Val Val Thr Asp Ser Ala Cys Ala Ser Thr Ser Gly Lys Trp Val
            65                  70                  75 tct ccc tat gac ggt gtc tcc acc acc ctc gca agt gac ctc gat att      503
Ser Pro Tyr Asp Gly Val Ser Thr Thr Leu Ala Ser Asp Leu Asp Ile
        80                  85                  90 gtacgcagat tgttagattc atatccttaa tctttcatac tgacagctct accag gat     561
                                                                Asp cac gtc gtg cct ctg aag gag gcg tgg gtc tcc ggt gcg cgc aac tgg      609
His Val Val Pro Leu Lys Glu Ala Trp Val Ser Gly Ala Arg Asn Trp
 95                 100                 105                 110 gac aat gcc aag cgt caa gcc ttt gcg aac gac ttg acg cgc ccc caa      657
Asp Asn Ala Lys Arg Gln Ala Phe Ala Asn Asp Leu Thr Arg Pro Gln
            115                 120                 125 ttg att gct gtc act gac tc gtgagtacca tagtacctct tacactcatg          707
Leu Ile Ala Val Thr Asp Ser
            130 agcacatcta aacttctacc ctgctgcag c ctc aac cag gca aag ggc gac aaa    761
                                  Leu Asn Gln Ala Lys Gly Asp Lys
                                          135                 140 g gtgtgtgtag acgtcaggcc ggtaaagggc gctgtctcat caatctattt ttag ac     818
                                                                Asp cct gcc gag tgg atg gtc cct ctc tcc agc tac aag tgc act tac gtc      866
Pro Ala Glu Trp Met Val Pro Leu Ser Ser Tyr Lys Cys Thr Tyr Val
        145                 150                 155 cgt gca tgg atc caa gtc aag tac tac tat ggc ctc agc gtc gac agc      914
Arg Ala Trp Ile Gln Val Lys Tyr Tyr Tyr Gly Leu Ser Val Asp Ser
    160                 165                 170
```

```
gcg gag aag act gcg ctt acg aac tac att aac gcc tgc tag         956
Ala Glu Lys Thr Ala Leu Thr Asn Tyr Ile Asn Ala Cys
175                 180                 185
```

<210> SEQ ID NO 11
<211> LENGTH: 204
<212> TYPE: PRT
<213> ORGANISM: Deconica coprophila

<400> SEQUENCE: 11

```
Met Arg Val Ser Val Ser Leu Leu Ala Leu Val Ser Ala Ala Thr
        -15                 -10                  -5

Ala Ser Val Leu Pro Arg Ala Leu Pro Thr Pro Val Ser Ala Ala Thr
 -1   1               5                  10                  15

Ala Lys Thr Tyr Leu Ala Ser Leu Lys Val Glu Ala Glu Ser Asn Ser
                 20                  25                  30

Pro Ala Tyr Asn Arg Asp Leu Phe Asn His Trp Ile Thr Ile Ser Gly
             35                  40                  45

Ser Cys Asn Thr Arg Glu Thr Val Leu Lys Arg Asp Gly Thr Ser Val
         50                  55                  60

Val Thr Asp Ser Ala Cys Ala Ser Thr Ser Gly Lys Trp Val Ser Pro
 65                  70                  75

Tyr Asp Gly Val Ser Thr Thr Leu Ala Ser Asp Leu Asp Ile Asp His
 80                  85                  90                  95

Val Val Pro Leu Lys Glu Ala Trp Val Ser Gly Ala Arg Asn Trp Asp
                100                 105                 110

Asn Ala Lys Arg Gln Ala Phe Ala Asn Asp Leu Thr Arg Pro Gln Leu
                115                 120                 125

Ile Ala Val Thr Asp Ser Leu Asn Gln Ala Lys Gly Asp Lys Asp Pro
            130                 135                 140

Ala Glu Trp Met Val Pro Leu Ser Ser Tyr Lys Cys Thr Tyr Val Arg
        145                 150                 155

Ala Trp Ile Gln Val Lys Tyr Tyr Gly Leu Ser Val Asp Ser Ala
160                 165                 170                 175

Glu Lys Thr Ala Leu Thr Asn Tyr Ile Asn Ala Cys
                180                 185
```

<210> SEQ ID NO 12
<211> LENGTH: 187
<212> TYPE: PRT
<213> ORGANISM: Deconica coprophila

<400> SEQUENCE: 12

```
Ser Val Leu Pro Arg Ala Leu Pro Thr Pro Val Ser Ala Ala Thr Ala
 1               5                  10                  15

Lys Thr Tyr Leu Ala Ser Leu Lys Val Glu Ala Glu Ser Asn Ser Pro
             20                  25                  30

Ala Tyr Asn Arg Asp Leu Phe Asn His Trp Ile Thr Ile Ser Gly Ser
         35                  40                  45

Cys Asn Thr Arg Glu Thr Val Leu Lys Arg Asp Gly Thr Ser Val Val
 50                  55                  60

Thr Asp Ser Ala Cys Ala Ser Thr Ser Gly Lys Trp Val Ser Pro Tyr
 65                  70                  75                  80

Asp Gly Val Ser Thr Thr Leu Ala Ser Asp Leu Asp Ile Asp His Val
                 85                  90                  95

Val Pro Leu Lys Glu Ala Trp Val Ser Gly Ala Arg Asn Trp Asp Asn
```

```
              100                 105                 110
Ala Lys Arg Gln Ala Phe Ala Asn Asp Leu Thr Arg Pro Gln Leu Ile
            115                 120                 125

Ala Val Thr Asp Ser Leu Asn Gln Ala Lys Gly Asp Lys Asp Pro Ala
        130                 135                 140

Glu Trp Met Val Pro Leu Ser Ser Tyr Lys Cys Thr Tyr Val Arg Ala
145                 150                 155                 160

Trp Ile Gln Val Lys Tyr Tyr Gly Leu Ser Val Asp Ser Ala Glu
                165                 170                 175

Lys Thr Ala Leu Thr Asn Tyr Ile Asn Ala Cys
            180                 185

<210> SEQ ID NO 13
<211> LENGTH: 618
<212> TYPE: DNA
<213> ORGANISM: Mortierella humilis
<220> FEATURE:
<221> NAME/KEY: CDS
<222> LOCATION: (1)..(615)
<220> FEATURE:
<221> NAME/KEY: sig_peptide
<222> LOCATION: (1)..(69)
<220> FEATURE:
<221> NAME/KEY: mat_peptide
<222> LOCATION: (70)..(615)

<400> SEQUENCE: 13 atg aag act cca ttc ctc gta ctg gca acc gca gcc gct ctt cta gct      48
Met Lys Thr Pro Phe Leu Val Leu Ala Thr Ala Ala Ala Leu Leu Ala
                -20                 -15                 -10 acc gcg aca cct gcg ttg gcc gag cta cca acc ccc gtc agc gcc gcc      96
Thr Ala Thr Pro Ala Leu Ala Glu Leu Pro Thr Pro Val Ser Ala Ala
            -5                  -1  1                   5 aca gcc agg acg tac ctg atg tct ctc acc gtc gag tcc gag aac aac     144
Thr Ala Arg Thr Tyr Leu Met Ser Leu Thr Val Glu Ser Glu Asn Asn
 10                  15                  20                  25 gtg ccc cca tac agc cgg agt ctg ttc aag cac tgg gac ata ata tct     192
Val Pro Pro Tyr Ser Arg Ser Leu Phe Lys His Trp Asp Ile Ile Ser
                 30                  35                  40 ggc aaa tgc gac acc cgg gaa acc gtc ctc aaa cgc gat ggc acc aat     240
Gly Lys Cys Asp Thr Arg Glu Thr Val Leu Lys Arg Asp Gly Thr Asn
             45                  50                  55 gtc gtc acc gac tct gcc tgc gcc gcc acc tct ggc cac tgg gtc agc     288
Val Val Thr Asp Ser Ala Cys Ala Ala Thr Ser Gly His Trp Val Ser
         60                  65                  70 cca tat gat ggc gcc gtc tgg gac aac cgc tca aat ctg gac atc gac     336
Pro Tyr Asp Gly Ala Val Trp Asp Asn Arg Ser Asn Leu Asp Ile Asp
 75                  80                  85 cac ctc gtg ccc ctg cgc gag gcg tgg gta tca ggc gcc cgc cta tgg     384
His Leu Val Pro Leu Arg Glu Ala Trp Val Ser Gly Ala Arg Leu Trp
 90                  95                 100                 105 acc aat gcg cag cgg gaa gca ttc gct aac gac ctc acc cga ccc cag     432
Thr Asn Ala Gln Arg Glu Ala Phe Ala Asn Asp Leu Thr Arg Pro Gln
                 110                 115                 120 ttg gtg gcg gtc act gac agg gtc aat cag gcc aag gga gac aaa gac     480
Leu Val Ala Val Thr Asp Arg Val Asn Gln Ala Lys Gly Asp Lys Asp
             125                 130                 135 cct gcc gaa tgg ttg cca cca ctt gcc tca tac cac tgc gtg tac gtt     528
Pro Ala Glu Trp Leu Pro Pro Leu Ala Ser Tyr His Cys Val Tyr Val
         140                 145                 150 cgc gcc tgg gtc cag gtg aag tac gtt tac ggc ctc acc gtc gat tcc     576
Arg Ala Trp Val Gln Val Lys Tyr Val Tyr Gly Leu Thr Val Asp Ser
```

```
Arg Ala Trp Val Gln Val Lys Tyr Val Tyr Gly Leu Thr Val Asp Ser
    155                 160                 165 gcc gag aag gac aag ctc acc agc cta ctc gcg gac tgc tga            618
Ala Glu Lys Asp Lys Leu Thr Ser Leu Leu Ala Asp Cys
170             175                 180
```

<210> SEQ ID NO 14
<211> LENGTH: 205
<212> TYPE: PRT
<213> ORGANISM: Mortierella humilis

<400> SEQUENCE: 14

```
Met Lys Thr Pro Phe Leu Val Leu Ala Thr Ala Ala Leu Leu Ala
            -20                 -15                 -10

Thr Ala Thr Pro Ala Leu Ala Glu Leu Pro Thr Pro Val Ser Ala Ala
            -5              -1  1               5

Thr Ala Arg Thr Tyr Leu Met Ser Leu Thr Val Glu Ser Glu Asn Asn
10                  15                  20                  25

Val Pro Pro Tyr Ser Arg Ser Leu Phe Lys His Trp Asp Ile Ile Ser
                30                  35                  40

Gly Lys Cys Asp Thr Arg Glu Thr Val Leu Lys Arg Asp Gly Thr Asn
            45                  50                  55

Val Val Thr Asp Ser Ala Cys Ala Ala Thr Ser Gly His Trp Val Ser
            60                  65                  70

Pro Tyr Asp Gly Ala Val Trp Asp Asn Arg Ser Asn Leu Asp Ile Asp
        75                  80                  85

His Leu Val Pro Leu Arg Glu Ala Trp Val Ser Gly Ala Arg Leu Trp
90                  95                  100                 105

Thr Asn Ala Gln Arg Glu Ala Phe Ala Asn Asp Leu Thr Arg Pro Gln
                110                 115                 120

Leu Val Ala Val Thr Asp Arg Val Asn Gln Ala Lys Gly Asp Lys Asp
            125                 130                 135

Pro Ala Glu Trp Leu Pro Pro Leu Ala Ser Tyr His Cys Val Tyr Val
            140                 145                 150

Arg Ala Trp Val Gln Val Lys Tyr Val Tyr Gly Leu Thr Val Asp Ser
            155                 160                 165

Ala Glu Lys Asp Lys Leu Thr Ser Leu Leu Ala Asp Cys
170                 175                 180
```

<210> SEQ ID NO 15
<211> LENGTH: 182
<212> TYPE: PRT
<213> ORGANISM: Mortierella humilis

<400> SEQUENCE: 15

```
Glu Leu Pro Thr Pro Val Ser Ala Ala Thr Ala Arg Thr Tyr Leu Met
1               5                   10                  15

Ser Leu Thr Val Glu Ser Glu Asn Asn Val Pro Pro Tyr Ser Arg Ser
            20                  25                  30

Leu Phe Lys His Trp Asp Ile Ile Ser Gly Lys Cys Asp Thr Arg Glu
        35                  40                  45

Thr Val Leu Lys Arg Asp Gly Thr Asn Val Val Thr Asp Ser Ala Cys
    50                  55                  60

Ala Ala Thr Ser Gly His Trp Val Ser Pro Tyr Asp Gly Ala Val Trp
65                  70                  75                  80

Asp Asn Arg Ser Asn Leu Asp Ile Asp His Leu Val Pro Leu Arg Glu
                85                  90                  95
```

```
Ala Trp Val Ser Gly Ala Arg Leu Trp Thr Asn Ala Gln Arg Glu Ala
            100                 105                 110
Phe Ala Asn Asp Leu Thr Arg Pro Gln Leu Val Ala Val Thr Asp Arg
            115                 120                 125
Val Asn Gln Ala Lys Gly Asp Lys Asp Pro Ala Glu Trp Leu Pro Pro
            130                 135                 140
Leu Ala Ser Tyr His Cys Val Tyr Val Arg Ala Trp Val Gln Val Lys
145                 150                 155                 160
Tyr Val Tyr Gly Leu Thr Val Asp Ser Ala Glu Lys Asp Lys Leu Thr
                165                 170                 175
Ser Leu Leu Ala Asp Cys
            180

<210> SEQ ID NO 16
<211> LENGTH: 999
<212> TYPE: DNA
<213> ORGANISM: Physisporinus sanguinolentus
<220> FEATURE:
<221> NAME/KEY: CDS
<222> LOCATION: (1)..(136)
<220> FEATURE:
<221> NAME/KEY: sig_peptide
<222> LOCATION: (1)..(54)
<220> FEATURE:
<221> NAME/KEY: mat_peptide
<222> LOCATION: (55)..(996)
<220> FEATURE:
<221> NAME/KEY: CDS
<222> LOCATION: (209)..(274)
<220> FEATURE:
<221> NAME/KEY: CDS
<222> LOCATION: (363)..(508)
<220> FEATURE:
<221> NAME/KEY: CDS
<222> LOCATION: (587)..(610)
<220> FEATURE:
<221> NAME/KEY: CDS
<222> LOCATION: (679)..(790)
<220> FEATURE:
<221> NAME/KEY: CDS
<222> LOCATION: (851)..(996)

<400> SEQUENCE: 16 atg gtt cgc ctt aca tcg atc ttc ttc cta ggt gtc gtc gta agt gtg      48
Met Val Arg Leu Thr Ser Ile Phe Phe Leu Gly Val Val Val Ser Val
            -15                 -10                 -5 ttg ggt gct ccc ata acc gcc ccg ttg tcc cgg agg gct tta ccc act      96
Leu Gly Ala Pro Ile Thr Ala Pro Leu Ser Arg Arg Ala Leu Pro Thr
    -1  1                   5                   10 ccc atc gct gcg tct aca gcc agg acg tat ctc ggc gaa t gtcagttact    146
Pro Ile Ala Ala Ser Thr Ala Arg Thr Tyr Leu Gly Glu
 15                  20                  25 agttttcggc tttgacgcgc attgaggctg atcatgattg gggatgtccc tcgttttcac   206 ag tg acg gta gca gtg gac tct aac gta cca gct tac gtc cga acc      252
   Leu Thr Val Ala Val Asp Ser Asn Val Pro Ala Tyr Val Arg Thr
            30                  35                  40 gag ttc aag act tgg gat atc a gtatgcatcc atctcccctt ttgtatacag      304
Glu Phe Lys Thr Trp Asp Ile
            45 attccgactt accattgctt aactcaatca tatccggaat tcgaccctcg gtgatcag    362 tc tct ggt act tgt gac aca cga gag aca gtt ctc aaa cga gac gga     409
Ile Ser Gly Thr Cys Asp Thr Arg Glu Thr Val Leu Lys Arg Asp Gly
 50                  55                  60                  65
```

-continued

```
aca aat gtc ata aca gat agt agc tgt aaa gct act tca ggt cat tgg    457
Thr Asn Val Ile Thr Asp Ser Ser Cys Lys Ala Thr Ser Gly His Trp
             70                  75                  80 gta tcc ccg tac gat aac gta cca act gat ctt gcc agt gat ctt gat    505
Val Ser Pro Tyr Asp Asn Val Pro Thr Asp Leu Ala Ser Asp Leu Asp
             85                  90                  95 atc gtaagtcgtt tctcggaggt acttacacct gagagtcttg atgctaaagt         558
Ile tgatgttgat gtgtaattct acacacag gac cac gtt gta cca ctc aaa gag     610
                                Asp His Val Val Pro Leu Lys Glu
                                            100                 105 gtatgtagac ctccgggata ccggtttctg ttgtcagcag atgagctgag cgtcgtttgt  670 atgtatag gca tgg gtt tct gga gca agg gat tgg acg gcc gca caa cgc   720
         Ala Trp Val Ser Gly Ala Arg Asp Trp Thr Ala Ala Gln Arg
                 110                 115                 120 gaa gcc ttc gca aat gat ctc acg cgt cct caa ctc gta gct gtc act    768
Glu Ala Phe Ala Asn Asp Leu Thr Arg Pro Gln Leu Val Ala Val Thr
                125                 130                 135 gat aac ttg aat cag tcg aaa g gtgtgtatta cttcatagtg ttgtcgtgat     820
Asp Asn Leu Asn Gln Ser Lys
            140 tgattagctg aagtcgaaac ctcattccag gc  gat aga gat ccg gct cag tgg   873
                                    Gly Asp Arg Asp Pro Ala Gln Trp
                                                145                 150 atg cct ccc ctt aca tct ttc aga tgt act tat gct cgg gca tgg gtg    921
Met Pro Pro Leu Thr Ser Phe Arg Cys Thr Tyr Ala Arg Ala Trp Val
                155                 160                 165 gaa gtt aag cat tac tat tct tta act gtg gac aca gcc gag aag tct    969
Glu Val Lys His Tyr Tyr Ser Leu Thr Val Asp Thr Ala Glu Lys Ser
                170                 175                 180 gcg ctg gag agc atc ctg gcg ggt tgt tga                            999
Ala Leu Glu Ser Ile Leu Ala Gly Cys
    185                 190
```

<210> SEQ ID NO 17
<211> LENGTH: 210
<212> TYPE: PRT
<213> ORGANISM: Physisporinus sanguinolentus

<400> SEQUENCE: 17

```
Met Val Arg Leu Thr Ser Ile Phe Phe Leu Gly Val Val Ser Val
            -15                 -10                  -5

Leu Gly Ala Pro Ile Thr Ala Pro Leu Ser Arg Arg Ala Leu Pro Thr
    -1  1               5                   10

Pro Ile Ala Ala Ser Thr Ala Arg Thr Tyr Leu Gly Glu Leu Thr Val
15                  20                  25                  30

Ala Val Asp Ser Asn Val Pro Ala Tyr Val Arg Thr Glu Phe Lys Thr
                35                  40                  45

Trp Asp Ile Ile Ser Gly Thr Cys Asp Thr Arg Glu Thr Val Leu Lys
                50                  55                  60

Arg Asp Gly Thr Asn Val Ile Thr Asp Ser Ser Cys Lys Ala Thr Ser
            65                  70                  75

Gly His Trp Val Ser Pro Tyr Asp Asn Val Pro Thr Asp Leu Ala Ser
        80                  85                  90

Asp Leu Asp Ile Asp His Val Val Pro Leu Lys Glu Ala Trp Val Ser
95                  100                 105                 110

Gly Ala Arg Asp Trp Thr Ala Ala Gln Arg Glu Ala Phe Ala Asn Asp
                115                 120                 125
```

-continued

Leu Thr Arg Pro Gln Leu Val Ala Val Thr Asp Asn Leu Asn Gln Ser
            130                 135                 140

Lys Gly Asp Arg Asp Pro Ala Gln Trp Met Pro Pro Leu Thr Ser Phe
            145                 150                 155

Arg Cys Thr Tyr Ala Arg Ala Trp Val Glu Val Lys His Tyr Tyr Ser
        160                 165                 170

Leu Thr Val Asp Thr Ala Glu Lys Ser Ala Leu Glu Ser Ile Leu Ala
175                 180                 185                 190

Gly Cys

<210> SEQ ID NO 18
<211> LENGTH: 192
<212> TYPE: PRT
<213> ORGANISM: Physisporinus sanguinolentus

<400> SEQUENCE: 18

Ala Pro Ile Thr Ala Pro Leu Ser Arg Arg Ala Leu Pro Thr Pro Ile
1               5                   10                  15

Ala Ala Ser Thr Ala Arg Thr Tyr Leu Gly Glu Leu Thr Val Ala Val
            20                  25                  30

Asp Ser Asn Val Pro Ala Tyr Val Arg Thr Glu Phe Lys Thr Trp Asp
        35                  40                  45

Ile Ile Ser Gly Thr Cys Asp Thr Arg Glu Thr Val Leu Lys Arg Asp
    50                  55                  60

Gly Thr Asn Val Ile Thr Asp Ser Ser Cys Lys Ala Thr Ser Gly His
65                  70                  75                  80

Trp Val Ser Pro Tyr Asp Asn Val Pro Thr Asp Leu Ala Ser Asp Leu
                85                  90                  95

Asp Ile Asp His Val Val Pro Leu Lys Glu Ala Trp Val Ser Gly Ala
            100                 105                 110

Arg Asp Trp Thr Ala Ala Gln Arg Glu Ala Phe Ala Asn Asp Leu Thr
        115                 120                 125

Arg Pro Gln Leu Val Ala Val Thr Asp Asn Leu Asn Gln Ser Lys Gly
    130                 135                 140

Asp Arg Asp Pro Ala Gln Trp Met Pro Pro Leu Thr Ser Phe Arg Cys
145                 150                 155                 160

Thr Tyr Ala Arg Ala Trp Val Glu Val Lys His Tyr Tyr Ser Leu Thr
                165                 170                 175

Val Asp Thr Ala Glu Lys Ser Ala Leu Glu Ser Ile Leu Ala Gly Cys
            180                 185                 190

<210> SEQ ID NO 19
<211> LENGTH: 1193
<212> TYPE: DNA
<213> ORGANISM: Stropharia semiglobata
<220> FEATURE:
<221> NAME/KEY: CDS
<222> LOCATION: (1)..(118)
<220> FEATURE:
<221> NAME/KEY: sig_peptide
<222> LOCATION: (1)..(51)
<220> FEATURE:
<221> NAME/KEY: mat_peptide
<222> LOCATION: (52)..(1190)
<220> FEATURE:
<221> NAME/KEY: CDS
<222> LOCATION: (177)..(242)
<220> FEATURE:
<221> NAME/KEY: CDS
<222> LOCATION: (294)..(320)

```
<220> FEATURE:
<221> NAME/KEY: CDS
<222> LOCATION: (377)..(495)
<220> FEATURE:
<221> NAME/KEY: CDS
<222> LOCATION: (549)..(572)
<220> FEATURE:
<221> NAME/KEY: CDS
<222> LOCATION: (629)..(723)
<220> FEATURE:
<221> NAME/KEY: CDS
<222> LOCATION: (784)..(800)
<220> FEATURE:
<221> NAME/KEY: CDS
<222> LOCATION: (990)..(998)
<220> FEATURE:
<221> NAME/KEY: CDS
<222> LOCATION: (1054)..(1190)

<400> SEQUENCE: 19
```

| | | |
|---|---|---|
| atg tat ctc tcc gtt gtc tcc gtt ctg ggc ctt gca tct gtg gct atg<br>Met Tyr Leu Ser Val Val Ser Val Leu Gly Leu Ala Ser Val Ala Met<br>       -15             -10                   -5 | | 48 |
| ggc atg gtt act ccc cgt gcg ctg cca acg cca gtg agc gcc gcg aca<br>Gly Met Val Thr Pro Arg Ala Leu Pro Thr Pro Val Ser Ala Ala Thr<br>-1  1                  5               10               15 | | 96 |
| gcg aag aca tac ctg gct gca t gtaagttgac acacactata tccaatccgc<br>Ala Lys Thr Tyr Leu Ala Ala<br>             20 | | 148 |
| aaagaggttg atgaatttat ttcttcag tg  acc gtg gag gcc gaa tcc aac<br>                                                  Leu Thr Val Glu Ala Glu Ser Asn<br>                                                    25                 30 | | 199 |
| tcc ccc gcc tat aac cgt gat ctt ttc aag cac tgg att acc a<br>Ser Pro Ala Tyr Asn Arg Asp Leu Phe Lys His Trp Ile Thr<br>             35                   40 | | 242 |
| gtctgtataa atcatgtcag taataaacag atactcacaa tattgtttta g tc  tcg<br>                                                                                        Ile Ser<br>                                                                                       45 | | 298 |
| ggg caa tgc aat acc aga gag a gtgggttttg tttaaacgtt tttgtctcca<br>Gly Gln Cys Asn Thr Arg Glu<br>             50 | | 350 |
| tgttctgaac agtttgcttt ctccag cc  gtt ctc aag cgc gac ggt act aat<br>                                                Thr Val Leu Lys Arg Asp Gly Thr Asn<br>                                                  55                         60 | | 402 |
| gtc gta acc gca tcc aac tgc gcg gca agt tct gga aac tgg gtc tct<br>Val Val Thr Ala Ser Asn Cys Ala Ala Ser Ser Gly Asn Trp Val Ser<br>         65                   70                    75 | | 450 |
| ccc tac gac aac att cct acc acc ctc gct agc gac ctt gat att<br>Pro Tyr Asp Asn Ile Pro Thr Thr Leu Ala Ser Asp Leu Asp Ile<br> 80                     85                      90 | | 495 |
| gtacgcgcaa tattactagg cgaagttttt gatagcttat cgcagtgttt tag gac<br>                                                                                              Asp | | 551 |
| cac ctc gta cca ttg aaa gag gtaaagagca tctgcatacg atatatcata<br>His Leu Val Pro Leu Lys Glu<br>95                   100 | | 602 |
| ggtgcaatat actcatttat gcatag gct tgg gtc tca ggc gct cgt aac tgg<br>                                                   Ala Trp Val Ser Gly Ala Arg Asn Trp<br>                                                                  105                         110 | | 655 |
| tcc aac gcc caa cgt gag gcc ttt gcc aac gac ctc acg cgt ccc cag<br>Ser Asn Ala Gln Arg Glu Ala Phe Ala Asn Asp Leu Thr Arg Pro Gln<br>              115                    120                   125 | | 703 |
| ctt gtt gct gtc acc gac tc  gtgcgtcctt taatttccat ataattgact<br>Leu Val Ala Val Thr Asp Ser<br>                   130 | | 753 |

```
attcgtctca tgccgccctt catcacacag g ctc aat cag gcc aag g              800
                                  Leu Asn Gln Ala Lys
                                          135 gtaagtgaca tttcatagct attccccttc cacgtttttt ttggcatctg ccaacccagt    860 ggtacgcccc agatgcgtcc tctgttgtcg gatatgaccc agaccggcat ctcccgcttc    920 attcattcaa tctattatgt tgcccacgaa ctgacggata tcccccttc ccaccatccc     980 cgtgaacag gt  gat aag g gtacgtgaac caatgtgcta cttaacatat            1028
             Gly Asp Lys
                 140 accgcctcct aacgcagagc cacag ac  ccc gcc gag tgg atg ccc cct ctc     1079
                                Asp Pro Ala Glu Trp Met Pro Pro Leu
                                        145                     150 gtc agt tac cag tgc acc tac acc cgt gcc tgg atc cac gtc aag tac    1127
Val Ser Tyr Gln Cys Thr Tyr Thr Arg Ala Trp Ile His Val Lys Tyr
              155                 160                 165 tac tat ggc ctc agc gtc gac tcc gcc gag aag gct gcg ctt acc aaa    1175
Tyr Tyr Gly Leu Ser Val Asp Ser Ala Glu Lys Ala Ala Leu Thr Lys
          170                 175                 180 tac ctc gcc gca tgc taa                                            1193
Tyr Leu Ala Ala Cys
        185

<210> SEQ ID NO 20
<211> LENGTH: 204
<212> TYPE: PRT
<213> ORGANISM: Stropharia semiglobata

<400> SEQUENCE: 20

Met Tyr Leu Ser Val Val Ser Val Leu Gly Leu Ala Ser Val Ala Met
        -15                 -10                  -5

Gly Met Val Thr Pro Arg Ala Leu Pro Thr Pro Val Ser Ala Ala Thr
 -1  1               5                  10                  15

Ala Lys Thr Tyr Leu Ala Ala Leu Thr Val Glu Ala Glu Ser Asn Ser
             20                  25                  30

Pro Ala Tyr Asn Arg Asp Leu Phe Lys His Trp Ile Thr Ile Ser Gly
         35                  40                  45

Gln Cys Asn Thr Arg Glu Thr Val Leu Lys Arg Asp Gly Thr Asn Val
     50                  55                  60

Val Thr Ala Ser Asn Cys Ala Ala Ser Ser Gly Asn Trp Val Ser Pro
 65                  70                  75

Tyr Asp Asn Ile Pro Thr Thr Leu Ala Ser Asp Leu Asp Ile Asp His
 80                  85                  90                  95

Leu Val Pro Leu Lys Glu Ala Trp Val Ser Gly Ala Arg Asn Trp Ser
                100                 105                 110

Asn Ala Gln Arg Glu Ala Phe Ala Asn Asp Leu Thr Arg Pro Gln Leu
            115                 120                 125

Val Ala Val Thr Asp Ser Leu Asn Gln Ala Lys Gly Asp Lys Asp Pro
        130                 135                 140

Ala Glu Trp Met Pro Pro Leu Val Ser Tyr Gln Cys Thr Tyr Thr Arg
    145                 150                 155

Ala Trp Ile His Val Lys Tyr Tyr Tyr Gly Leu Ser Val Asp Ser Ala
160                 165                 170                 175

Glu Lys Ala Ala Leu Thr Lys Tyr Leu Ala Ala Cys
                180                 185
```

```
<210> SEQ ID NO 21
<211> LENGTH: 187
<212> TYPE: PRT
<213> ORGANISM: Stropharia semiglobata

<400> SEQUENCE: 21
```

Met Val Thr Pro Arg Ala Leu Pro Thr Pro Val Ser Ala Ala Thr Ala
1               5                   10                  15

Lys Thr Tyr Leu Ala Ala Leu Thr Val Glu Ala Glu Ser Asn Ser Pro
            20                  25                  30

Ala Tyr Asn Arg Asp Leu Phe Lys His Trp Ile Thr Ile Ser Gly Gln
        35                  40                  45

Cys Asn Thr Arg Glu Thr Val Leu Lys Arg Asp Gly Thr Asn Val Val
50                  55                  60

Thr Ala Ser Asn Cys Ala Ala Ser Ser Gly Asn Trp Val Ser Pro Tyr
65                  70                  75                  80

Asp Asn Ile Pro Thr Thr Leu Ala Ser Asp Leu Asp Ile Asp His Leu
                85                  90                  95

Val Pro Leu Lys Glu Ala Trp Val Ser Gly Ala Arg Asn Trp Ser Asn
            100                 105                 110

Ala Gln Arg Glu Ala Phe Ala Asn Asp Leu Thr Arg Pro Gln Leu Val
        115                 120                 125

Ala Val Thr Asp Ser Leu Asn Gln Ala Lys Gly Asp Lys Asp Pro Ala
130                 135                 140

Glu Trp Met Pro Pro Leu Val Ser Tyr Gln Cys Thr Tyr Thr Arg Ala
145                 150                 155                 160

Trp Ile His Val Lys Tyr Tyr Tyr Gly Leu Ser Val Asp Ser Ala Glu
                165                 170                 175

Lys Ala Ala Leu Thr Lys Tyr Leu Ala Ala Cys
            180                 185

```
<210> SEQ ID NO 22
<211> LENGTH: 747
<212> TYPE: DNA
<213> ORGANISM: Cladosporium cladosporioides
<220> FEATURE:
<221> NAME/KEY: CDS
<222> LOCATION: (1)..(369)
<220> FEATURE:
<221> NAME/KEY: sig_peptide
<222> LOCATION: (1)..(54)
<220> FEATURE:
<221> NAME/KEY: mat_peptide
<222> LOCATION: (55)..(744)
<220> FEATURE:
<221> NAME/KEY: CDS
<222> LOCATION: (424)..(488)
<220> FEATURE:
<221> NAME/KEY: CDS
<222> LOCATION: (543)..(744 )

<400> SEQUENCE: 22
``` atg gct ctc aac act gct gtt gcg gtt ctc ctt gct gcc acc gcg gcc    48
Met Ala Leu Asn Thr Ala Val Ala Val Leu Leu Ala Ala Thr Ala Ala
            -15                 -10                 -5 ttc gct gca ccc att gag cct gcc gta tcg cgc cgt ggc aac ctc cct    96
Phe Ala Ala Pro Ile Glu Pro Ala Val Ser Arg Arg Gly Asn Leu Pro
        -1  1               5                   10 aca cca atc tct gtt gct acc gcg aga acc tac ttg tcg cag ctc acc   144
Thr Pro Ile Ser Val Ala Thr Ala Arg Thr Tyr Leu Ser Gln Leu Thr
15                  20                  25                  30 gtc gag gcc gag agt aac agc ccg gcg tat gac cgc gac cta ttc aac   192

```
                Val Glu Ala Glu Ser Asn Ser Pro Ala Tyr Asp Arg Asp Leu Phe Asn
                                 35                  40                  45 cac tgg atc acg atc agc ggc act tgc aat acc aga gag acc gta ttg          240
His Trp Ile Thr Ile Ser Gly Thr Cys Asn Thr Arg Glu Thr Val Leu
             50                  55                  60 aag cgc gac ggc agc ggt gtc gtg acg agc agt gcc tgc gcc tcg acc          288
Lys Arg Asp Gly Ser Gly Val Val Thr Ser Ser Ala Cys Ala Ser Thr
             65                  70                  75 tct ggc tct tgg tac agc gac tat gat ggc ttg aca ttc acg gtc gcg          336
Ser Gly Ser Trp Tyr Ser Asp Tyr Asp Gly Leu Thr Phe Thr Val Ala
         80                  85                  90 agc gaa ctt gac att gat cat ttg gtc cct ctc gtaagtctat cgcctgcaaa        389
Ser Glu Leu Asp Ile Asp His Leu Val Pro Leu
 95                 100                 105 tgatacagaa aggcagatac tgagacgatc ccag aaa gaa gca tgg gtt tcc ggc        444
                                      Lys Glu Ala Trp Val Ser Gly
                                                          110 gca agg acc tgg acc gac gct cgc cgt gag cag ttt gcc aac ga              488
Ala Arg Thr Trp Thr Asp Ala Arg Arg Glu Gln Phe Ala Asn Asp
             115                 120                 125 gtaagtactt tgcttgtccc tactggctat cgcagcatat actgaaaata atag c ttg        546
                                                             Leu act cgc cct caa ctc ctt gcc gtt agc gcc acc agc aac cgc cag aag          594
Thr Arg Pro Gln Leu Leu Ala Val Ser Ala Thr Ser Asn Arg Gln Lys
         130                 135                 140 ggc gat ggc gac cct gct gag tgg ctg cct gca cgt gag gat tac cag          642
Gly Asp Gly Asp Pro Ala Glu Trp Leu Pro Ala Arg Glu Asp Tyr Gln
145                 150                 155                 160 tgc gaa tat gtg cgc gct tgg atc cag gtg aag cag tac tat ggc ttg          690
Cys Glu Tyr Val Arg Ala Trp Ile Gln Val Lys Gln Tyr Tyr Gly Leu
                 165                 170                 175 agt gtc gat acg ctt gag aag gcg gcg ctt ggg aat gtg ttg aac aat          738
Ser Val Asp Thr Leu Glu Lys Ala Ala Leu Gly Asn Val Leu Asn Asn
             180                 185                 190 gtt tgt tga                                                              747
Val Cys <210> SEQ ID NO 23
<211> LENGTH: 212
<212> TYPE: PRT
<213> ORGANISM: Cladosporium cladosporioides

<400> SEQUENCE: 23

Met Ala Leu Asn Thr Ala Val Ala Val Leu Leu Ala Ala Thr Ala Ala
                -15                 -10                  -5

Phe Ala Ala Pro Ile Glu Pro Ala Val Ser Arg Arg Gly Asn Leu Pro
 -1  1               5                  10

Thr Pro Ile Ser Val Ala Thr Ala Arg Thr Tyr Leu Ser Gln Leu Thr
15                  20                  25                  30

Val Glu Ala Glu Ser Asn Ser Pro Ala Tyr Asp Arg Asp Leu Phe Asn
                 35                  40                  45

His Trp Ile Thr Ile Ser Gly Thr Cys Asn Thr Arg Glu Thr Val Leu
             50                  55                  60

Lys Arg Asp Gly Ser Gly Val Val Thr Ser Ser Ala Cys Ala Ser Thr
             65                  70                  75

Ser Gly Ser Trp Tyr Ser Asp Tyr Asp Gly Leu Thr Phe Thr Val Ala
         80                  85                  90

Ser Glu Leu Asp Ile Asp His Leu Val Pro Leu Lys Glu Ala Trp Val
```

```
                95                  100                 105                 110
Ser Gly Ala Arg Thr Trp Thr Asp Ala Arg Arg Glu Gln Phe Ala Asn
                115                 120                 125

Asp Leu Thr Arg Pro Gln Leu Leu Ala Val Ser Ala Thr Ser Asn Arg
                130                 135                 140

Gln Lys Gly Asp Gly Asp Pro Ala Glu Trp Leu Pro Ala Arg Glu Asp
                145                 150                 155

Tyr Gln Cys Glu Tyr Val Arg Ala Trp Ile Gln Val Lys Gln Tyr Tyr
                160                 165                 170

Gly Leu Ser Val Asp Thr Leu Glu Lys Ala Ala Leu Gly Asn Val Leu
175                 180                 185                 190

Asn Asn Val Cys

<210> SEQ ID NO 24
<211> LENGTH: 194
<212> TYPE: PRT
<213> ORGANISM: Cladosporium cladosporioides

<400> SEQUENCE: 24

Ala Pro Ile Glu Pro Ala Val Ser Arg Arg Gly Asn Leu Pro Thr Pro
1               5                   10                  15

Ile Ser Val Ala Thr Ala Arg Thr Tyr Leu Ser Gln Leu Thr Val Glu
                20                  25                  30

Ala Glu Ser Asn Ser Pro Ala Tyr Asp Arg Asp Leu Phe Asn His Trp
                35                  40                  45

Ile Thr Ile Ser Gly Thr Cys Asn Thr Arg Glu Thr Val Leu Lys Arg
            50                  55                  60

Asp Gly Ser Gly Val Val Thr Ser Ser Ala Cys Ala Ser Thr Ser Gly
65                  70                  75                  80

Ser Trp Tyr Ser Asp Tyr Asp Gly Leu Thr Phe Thr Val Ala Ser Glu
                85                  90                  95

Leu Asp Ile Asp His Leu Val Pro Leu Lys Glu Ala Trp Val Ser Gly
                100                 105                 110

Ala Arg Thr Trp Thr Asp Ala Arg Arg Glu Gln Phe Ala Asn Asp Leu
                115                 120                 125

Thr Arg Pro Gln Leu Leu Ala Val Ser Ala Thr Ser Asn Arg Gln Lys
            130                 135                 140

Gly Asp Gly Asp Pro Ala Glu Trp Leu Pro Ala Arg Glu Asp Tyr Gln
145                 150                 155                 160

Cys Glu Tyr Val Arg Ala Trp Ile Gln Val Lys Gln Tyr Tyr Gly Leu
                165                 170                 175

Ser Val Asp Thr Leu Glu Lys Ala Ala Leu Gly Asn Val Leu Asn Asn
                180                 185                 190

Val Cys

<210> SEQ ID NO 25
<211> LENGTH: 978
<212> TYPE: DNA
<213> ORGANISM: Irpex lacteus
<220> FEATURE:
<221> NAME/KEY: CDS
<222> LOCATION: (1)..(160)
<220> FEATURE:
<221> NAME/KEY: sig_peptide
<222> LOCATION: (1)..(63)
<220> FEATURE:
<221> NAME/KEY: mat_peptide
<222> LOCATION: (64)..(975)
```

```
<220> FEATURE:
<221> NAME/KEY: CDS
<222> LOCATION: (213)..(278)
<220> FEATURE:
<221> NAME/KEY: CDS
<222> LOCATION: (332)..(477)
<220> FEATURE:
<221> NAME/KEY: CDS
<222> LOCATION: (555)..(578)
<220> FEATURE:
<221> NAME/KEY: CDS
<222> LOCATION: (656)..(767)
<220> FEATURE:
<221> NAME/KEY: CDS
<222> LOCATION: (830)..(975)

<400> SEQUENCE: 25
```

| | | | | | | | | | | | | | | | | |
|---|---|---|---|---|---|---|---|---|---|---|---|---|---|---|---|---|
| atg | tcg | cct | tca | aag | ttc | tcc | ctc | gta | gtt | gct | gga | ctc | ctc | ctc | gcg | 48 |
| Met | Ser | Pro | Ser | Lys | Phe | Ser | Leu | Val | Val | Ala | Gly | Leu | Leu | Leu | Ala | |
| | -20 | | | | -15 | | | | | -10 | | | | | | |

| | | | | | | | | | | | | | | | | |
|---|---|---|---|---|---|---|---|---|---|---|---|---|---|---|---|---|
| gca | cag | gtc | aca | gcg | gca | ccc | gtt | cct | ggg | ctc | gca | ggc | aat | gag | gtg | 96 |
| Ala | Gln | Val | Thr | Ala | Ala | Pro | Val | Pro | Gly | Leu | Ala | Gly | Asn | Glu | Val | |
| -5 | | | | | -1 | 1 | | | 5 | | | | | 10 | | |

| | | | | | | | | | | | | | | | | |
|---|---|---|---|---|---|---|---|---|---|---|---|---|---|---|---|---|
| ctg | gcc | aga | cgt | gcg | ctg | cct | acg | ccg | gta | tcg | gtg | gct | acc | gcg | aag | 144 |
| Leu | Ala | Arg | Arg | Ala | Leu | Pro | Thr | Pro | Val | Ser | Val | Ala | Thr | Ala | Lys | |
| | | 15 | | | | | 20 | | | | | 25 | | | | |

| | | | | | | | | | | |
|---|---|---|---|---|---|---|---|---|---|---|
| acc | tac | tta | agc | gaa | c gtgagtaatg tgtcgtggat ggtgtggttt gacttaacca | 200 |
| Thr | Tyr | Leu | Ser | Glu | | |
| | | 30 | | | | |

| | | | | | | | | | | | |
|---|---|---|---|---|---|---|---|---|---|---|---|
| gctcgtctgc ag ta | acg | gtc | gcg | acg | gac | tcc | aac | tcc | ccg | gcg | tac | gca | 250 |
| | Leu | Thr | Val | Ala | Thr | Asp | Ser | Asn | Ser | Pro | Ala | Tyr | Ala |
| | | 35 | | | | 40 | | | | | 45 | |

| | | | | | | | | | |
|---|---|---|---|---|---|---|---|---|---|
| cgg | act | aag | ttc | aag | act | tgg | gat | acc | a gtacgttcac tgagatatac | 298 |
| Arg | Thr | Lys | Phe | Lys | Thr | Trp | Asp | Thr | | |
| | | | 50 | | | | | | | |

| | | | | | | | | |
|---|---|---|---|---|---|---|---|---|
| gcctgcattc gccgatgttt atcgaatgtc cag tt | tct | gga | agc | tgc | gat | aca | 351 |
| | Ile | Ser | Gly | Ser | Cys | Asp | Thr | |
| | | 55 | | | | 60 | | |

| | | | | | | | | | | | | | | | | |
|---|---|---|---|---|---|---|---|---|---|---|---|---|---|---|---|---|
| cga | gaa | acc | gtt | ctc | aag | cgc | gat | ggc | aca | gat | gtc | gtc | acc | gac | agc | 399 |
| Arg | Glu | Thr | Val | Leu | Lys | Arg | Asp | Gly | Thr | Asp | Val | Val | Thr | Asp | Ser | |
| | | | | 65 | | | | | 70 | | | | | 75 | | |

| | | | | | | | | | | | | | | | | |
|---|---|---|---|---|---|---|---|---|---|---|---|---|---|---|---|---|
| agc | tgc | aaa | gcc | acc | tcc | gga | cac | tgg | gtt | tcg | ccg | tac | gac | ggc | gtg | 447 |
| Ser | Cys | Lys | Ala | Thr | Ser | Gly | His | Trp | Val | Ser | Pro | Tyr | Asp | Gly | Val | |
| | | 80 | | | | | 85 | | | | | 90 | | | | |

| | | | | | | | | | | |
|---|---|---|---|---|---|---|---|---|---|---|
| ccc | acc | gac | ctc | gcg | agc | gat | ttg | gac | att | gtaagtcccg gagcttcctg | 497 |
| Pro | Thr | Asp | Leu | Ala | Ser | Asp | Leu | Asp | Ile | |
| | 95 | | | | 100 | | | | | |

| | |
|---|---|
| ccagatagcc tcatgatccg cgagaattcg aagcttgata actgataatc gcgccag | 554 |

| | | | | | | | |
|---|---|---|---|---|---|---|---|
| gat | cac | ctt | gta | cct | ttg | aaa | gag gtgagataat cggcaaacat agctgtccga | 608 |
| Asp | His | Leu | Val | Pro | Leu | Lys | Glu |
| | 105 | | | | 110 | | |

| | | |
|---|---|---|
| caaataccgt gtgtggtttg actcacgggt gtcggtgatt ttgatag | gcc tgg ctc | 664 |
| | Ala Trp Leu | |

| | | | | | | | | | | | | | | | | |
|---|---|---|---|---|---|---|---|---|---|---|---|---|---|---|---|---|
| tcc | gga | gcg | cgg | gac | tgg | act | gac | gcg | cag | agg | gag | gcg | tat | gcg | aac | 712 |
| Ser | Gly | Ala | Arg | Asp | Trp | Thr | Asp | Ala | Gln | Arg | Glu | Ala | Tyr | Ala | Asn | |
| 115 | | | | | 120 | | | | | 125 | | | | | 130 | |

| | | | | | | | | | | | | | | | | |
|---|---|---|---|---|---|---|---|---|---|---|---|---|---|---|---|---|
| gac | ttg | acc | cgg | cca | caa | ctt | gtc | gcc | gtc | acg | gat | aac | ttg | aac | gag | 760 |
| Asp | Leu | Thr | Arg | Pro | Gln | Leu | Val | Ala | Val | Thr | Asp | Asn | Leu | Asn | Glu | |
| | | | | 135 | | | | | 140 | | | | | 145 | | |

| | | |
|---|---|---|
| tcc | aaa | g gtgcgtttgt acatcccgat gttggtccac gtattcgaaa ttgagcggca | 817 |
| Ser | Lys | |

| | | | | | | | | | | | | | |
|---|---|---|---|---|---|---|---|---|---|---|---|---|---|
| ctgctacacc ag gt | gac | aag | gac | atc | gca | cac | tgg | cag | ccc | ccg | ctg | gcg | 867 |

```
            Gly Asp Lys Asp Ile Ala His Trp Gln Pro Pro Leu Ala
                150                 155                 160 tcg ttc cag tgc acg tac gcg cgc gcc tgg gtg cag gtg aag cat tat      915
Ser Phe Gln Cys Thr Tyr Ala Arg Ala Trp Val Gln Val Lys His Tyr
        165                 170                 175 tat tct ttg acg atc gac acg gac gag aag agt gcg ttg act acg att      963
Tyr Ser Leu Thr Ile Asp Thr Asp Glu Lys Ser Ala Leu Thr Thr Ile
            180                 185                 190 ctg aac ggg tgt tga                                                  978
Leu Asn Gly Cys
        195
```

<210> SEQ ID NO 26
<211> LENGTH: 218
<212> TYPE: PRT
<213> ORGANISM: Irpex lacteus

<400> SEQUENCE: 26

```
Met Ser Pro Ser Lys Phe Ser Leu Val Val Ala Gly Leu Leu Leu Ala
        -20                 -15                 -10

Ala Gln Val Thr Ala Ala Pro Val Pro Gly Leu Ala Gly Asn Glu Val
-5               -1  1               5                   10

Leu Ala Arg Arg Ala Leu Pro Thr Pro Val Ser Val Ala Thr Ala Lys
                15                  20                  25

Thr Tyr Leu Ser Glu Leu Thr Val Ala Thr Asp Ser Asn Ser Pro Ala
        30                  35                  40

Tyr Ala Arg Thr Lys Phe Lys Thr Trp Asp Thr Ile Ser Gly Ser Cys
    45                  50                  55

Asp Thr Arg Glu Thr Val Leu Lys Arg Asp Gly Thr Asp Val Val Thr
60                  65                  70                  75

Asp Ser Ser Cys Lys Ala Thr Ser Gly His Trp Val Ser Pro Tyr Asp
                80                  85                  90

Gly Val Pro Thr Asp Leu Ala Ser Asp Leu Asp Ile Asp His Leu Val
            95                  100                 105

Pro Leu Lys Glu Ala Trp Leu Ser Gly Ala Arg Asp Trp Thr Asp Ala
        110                 115                 120

Gln Arg Glu Ala Tyr Ala Asn Asp Leu Thr Arg Pro Gln Leu Val Ala
    125                 130                 135

Val Thr Asp Asn Leu Asn Glu Ser Lys Gly Asp Lys Asp Ile Ala His
140                 145                 150                 155

Trp Gln Pro Pro Leu Ala Ser Phe Gln Cys Thr Tyr Ala Arg Ala Trp
                160                 165                 170

Val Gln Val Lys His Tyr Tyr Ser Leu Thr Ile Asp Thr Asp Glu Lys
            175                 180                 185

Ser Ala Leu Thr Thr Ile Leu Asn Gly Cys
        190                 195
```

<210> SEQ ID NO 27
<211> LENGTH: 197
<212> TYPE: PRT
<213> ORGANISM: Irpex lacteus

<400> SEQUENCE: 27

```
Ala Pro Val Pro Gly Leu Ala Gly Asn Glu Val Leu Ala Arg Arg Ala
1               5                   10                  15

Leu Pro Thr Pro Val Ser Val Ala Thr Ala Lys Thr Tyr Leu Ser Glu
            20                  25                  30
```

```
Leu Thr Val Ala Thr Asp Ser Asn Ser Pro Ala Tyr Ala Arg Thr Lys
             35                  40                  45

Phe Lys Thr Trp Asp Thr Ile Ser Gly Ser Cys Asp Thr Arg Glu Thr
 50                  55                  60

Val Leu Lys Arg Asp Gly Thr Asp Val Val Thr Asp Ser Ser Cys Lys
 65                  70                  75                  80

Ala Thr Ser Gly His Trp Val Ser Pro Tyr Asp Gly Val Pro Thr Asp
                 85                  90                  95

Leu Ala Ser Asp Leu Asp Ile Asp His Leu Val Pro Leu Lys Glu Ala
                100                 105                 110

Trp Leu Ser Gly Ala Arg Asp Trp Thr Asp Ala Gln Arg Glu Ala Tyr
                115                 120                 125

Ala Asn Asp Leu Thr Arg Pro Gln Leu Val Ala Val Thr Asp Asn Leu
                130                 135                 140

Asn Glu Ser Lys Gly Asp Lys Asp Ile Ala His Trp Gln Pro Pro Leu
145                 150                 155                 160

Ala Ser Phe Gln Cys Thr Tyr Ala Arg Ala Trp Val Gln Val Lys His
                165                 170                 175

Tyr Tyr Ser Leu Thr Ile Asp Thr Asp Glu Lys Ser Ala Leu Thr Thr
                180                 185                 190

Ile Leu Asn Gly Cys
        195

<210> SEQ ID NO 28
<211> LENGTH: 927
<212> TYPE: DNA
<213> ORGANISM: Phlebia subochracea
<220> FEATURE:
<221> NAME/KEY: CDS
<222> LOCATION: (1)..(124)
<220> FEATURE:
<221> NAME/KEY: sig_peptide
<222> LOCATION: (1)..(54)
<220> FEATURE:
<221> NAME/KEY: mat_peptide
<222> LOCATION: (55)..(924)
<220> FEATURE:
<221> NAME/KEY: CDS
<222> LOCATION: (180)..(245)
<220> FEATURE:
<221> NAME/KEY: CDS
<222> LOCATION: (296)..(441)
<220> FEATURE:
<221> NAME/KEY: CDS
<222> LOCATION: (506)..(529)
<220> FEATURE:
<221> NAME/KEY: CDS
<222> LOCATION: (587)..(698)
<220> FEATURE:
<221> NAME/KEY: CDS
<222> LOCATION: (779)..(924)

<400> SEQUENCE: 28 atg ctg tcc tct ttt cct ctg gtc ttc ctc gcg ttg gtc aca gga gcg      48
Met Leu Ser Ser Phe Pro Leu Val Phe Leu Ala Leu Val Thr Gly Ala
        -15                 -10                  -5 ctt gct tct cct ctc gag agc cgc gca ctg cct acg cca gtc tct gtt      96
Leu Ala Ser Pro Leu Glu Ser Arg Ala Leu Pro Thr Pro Val Ser Val
  -1  1                   5                  10 tcc act gca cag tct tat ttg agc cag t gtacgtcaca tatgctgctc         144
Ser Thr Ala Gln Ser Tyr Leu Ser Gln
 15                  20 ttgaccacgg tgctgatact atcatttctt aacag tg  gtt gtg gcc gtg gac      196
                                         Leu Val Val Ala Val Asp
```

-continued

```
tcc aat tct ccc gca tat gat cga gat ttg ttc aag aca tgg gat acc a    245
Ser Asn Ser Pro Ala Tyr Asp Arg Asp Leu Phe Lys Thr Trp Asp Thr
 30              35                  40                  45 gtacgtcgcg tactgttcat cttgaataaa atgttagcta atctctgcag tc tct       300
                                                           Ile Ser ggc act tgc gac act cgt gag acg gtc ttg aaa cgt gac ggc acc aat    348
Gly Thr Cys Asp Thr Arg Glu Thr Val Leu Lys Arg Asp Gly Thr Asn
         50                  55                  60 gtc gtc aca gac agc agt tgc aag gcc acc tct ggg aac tgg gta tct    396
Val Val Thr Asp Ser Ser Cys Lys Ala Thr Ser Gly Asn Trp Val Ser
 65                  70                  75 ccc tac gac gga gtg gcc acc acc ctt gct agc gac ctt gat atc        441
Pro Tyr Asp Gly Val Ala Thr Thr Leu Ala Ser Asp Leu Asp Ile
 80                  85                  90 gtgcgtgttc tttggccttg attggccttc gcctcaagtt tatttggact gtgatgcttt  501 acag gac cac ctc gtg cca ctc aaa gag gtaaaccatc gccagcgtcg         549
     Asp His Leu Val Pro Leu Lys Glu
         95                  100 tgggccgctg aatgcatatt tacatcataa ctcgcag gca tgg ctg tca ggc gcc   604
                                          Ala Trp Leu Ser Gly Ala
                                                           105 cgt aac tgg acc ccc gct cag cgt gag gct ttt gcc aac gac cta acg    652
Arg Asn Trp Thr Pro Ala Gln Arg Glu Ala Phe Ala Asn Asp Leu Thr
        110                 115                 120 cgt ccc cag ctc gtc gca gtt acc gac aac ctc aac gag tcc aaa g      698
Arg Pro Gln Leu Val Ala Val Thr Asp Asn Leu Asn Glu Ser Lys
125                 130                 135 gcaagtccgc ggatcacacc gtatccgctt gtgcctgatt cacattgcg gactgacgtc   758 aatcttcctc gcatgcacag gc gat aag gat atc gcg cag tgg ctg ccg ccg   810
                         Gly Asp Lys Asp Ile Ala Gln Trp Leu Pro Pro
                             140                 145                 150 ctc aag tcc ttc cag tgc acc tac gcg cgc gct tgg gtc caa gtg aag    858
Leu Lys Ser Phe Gln Cys Thr Tyr Ala Arg Ala Trp Val Gln Val Lys
        155                 160                 165 tac tac tac tcg ctg acc atc gac tcg gcg gag aag acc gcg ctg cag    906
Tyr Tyr Tyr Ser Leu Thr Ile Asp Ser Ala Glu Lys Thr Ala Leu Gln
        170                 175                 180 aac ctc ctt gca ggc tgc tag                                        927
Asn Leu Leu Ala Gly Cys
        185

<210> SEQ ID NO 29
<211> LENGTH: 206
<212> TYPE: PRT
<213> ORGANISM: Phlebia subochracea

<400> SEQUENCE: 29

Met Leu Ser Ser Phe Pro Leu Val Phe Leu Ala Leu Val Thr Gly Ala
            -15                 -10                  -5

Leu Ala Ser Pro Leu Glu Ser Arg Ala Leu Pro Thr Pro Val Ser Val
 -1  1               5                  10

Ser Thr Ala Gln Ser Tyr Leu Ser Gln Leu Val Val Ala Val Asp Ser
 15                  20                  25                  30

Asn Ser Pro Ala Tyr Asp Arg Asp Leu Phe Lys Thr Trp Asp Thr Ile
                     35                  40                  45

Ser Gly Thr Cys Asp Thr Arg Glu Thr Val Leu Lys Arg Asp Gly Thr
         50                  55                  60
```

-continued

Asn Val Val Thr Asp Ser Ser Cys Lys Ala Thr Ser Gly Asn Trp Val
            65                  70                  75

Ser Pro Tyr Asp Gly Val Ala Thr Thr Leu Ala Ser Asp Leu Asp Ile
 80                  85                  90

Asp His Leu Val Pro Leu Lys Glu Ala Trp Leu Ser Gly Ala Arg Asn
 95                 100                 105                 110

Trp Thr Pro Ala Gln Arg Glu Ala Phe Ala Asn Asp Leu Thr Arg Pro
                115                 120                 125

Gln Leu Val Ala Val Thr Asp Asn Leu Asn Glu Ser Lys Gly Asp Lys
            130                 135                 140

Asp Ile Ala Gln Trp Leu Pro Pro Leu Lys Ser Phe Gln Cys Thr Tyr
            145                 150                 155

Ala Arg Ala Trp Val Gln Val Lys Tyr Tyr Ser Leu Thr Ile Asp
            160                 165                 170

Ser Ala Glu Lys Thr Ala Leu Gln Asn Leu Leu Ala Gly Cys
175                 180                 185

<210> SEQ ID NO 30
<211> LENGTH: 188
<212> TYPE: PRT
<213> ORGANISM: Phlebia subochracea

<400> SEQUENCE: 30

Ser Pro Leu Glu Ser Arg Ala Leu Pro Thr Pro Val Ser Val Ser Thr
 1               5                  10                  15

Ala Gln Ser Tyr Leu Ser Gln Leu Val Val Ala Val Asp Ser Asn Ser
            20                  25                  30

Pro Ala Tyr Asp Arg Asp Leu Phe Lys Thr Trp Asp Thr Ile Ser Gly
            35                  40                  45

Thr Cys Asp Thr Arg Glu Thr Val Leu Lys Arg Asp Gly Thr Asn Val
 50                  55                  60

Val Thr Asp Ser Ser Cys Lys Ala Thr Ser Gly Asn Trp Val Ser Pro
65                  70                  75                  80

Tyr Asp Gly Val Ala Thr Thr Leu Ala Ser Asp Leu Asp Ile Asp His
                85                  90                  95

Leu Val Pro Leu Lys Glu Ala Trp Leu Ser Gly Ala Arg Asn Trp Thr
            100                 105                 110

Pro Ala Gln Arg Glu Ala Phe Ala Asn Asp Leu Thr Arg Pro Gln Leu
        115                 120                 125

Val Ala Val Thr Asp Asn Leu Asn Glu Ser Lys Gly Asp Lys Asp Ile
    130                 135                 140

Ala Gln Trp Leu Pro Pro Leu Lys Ser Phe Gln Cys Thr Tyr Ala Arg
145                 150                 155                 160

Ala Trp Val Gln Val Lys Tyr Tyr Ser Leu Thr Ile Asp Ser Ala
                165                 170                 175

Glu Lys Thr Ala Leu Gln Asn Leu Leu Ala Gly Cys
            180                 185

<210> SEQ ID NO 31
<211> LENGTH: 986
<212> TYPE: DNA
<213> ORGANISM: Rhizoctonia solani
<220> FEATURE:
<221> NAME/KEY: CDS
<222> LOCATION: (1)..(167)
<220> FEATURE:
<221> NAME/KEY: sig_peptide

```
<222> LOCATION: (1)..(45)
<220> FEATURE:
<221> NAME/KEY: mat_peptide
<222> LOCATION: (46)..(983)
<220> FEATURE:
<221> NAME/KEY: CDS
<222> LOCATION: (224)..(282)
<220> FEATURE:
<221> NAME/KEY: CDS
<222> LOCATION: (332)..(403)
<220> FEATURE:
<221> NAME/KEY: CDS
<222> LOCATION: (454)..(614)
<220> FEATURE:
<221> NAME/KEY: CDS
<222> LOCATION: (665)..(731)
<220> FEATURE:
<221> NAME/KEY: CDS
<222> LOCATION: (783)..(828)
<220> FEATURE:
<221> NAME/KEY: CDS
<222> LOCATION: (887)..(983)

<400> SEQUENCE: 31 atg cac ttc aag tat ctt ctg gcg ttc gca tct ctg gca acc gcg tct      48
Met His Phe Lys Tyr Leu Leu Ala Phe Ala Ser Leu Ala Thr Ala Ser
-15             -10                 -5                  -1  1 ccg ctc agt ccc agc tct ggc att ggc cgc aga gca ctt ccg aca cca      96
Pro Leu Ser Pro Ser Ser Gly Ile Gly Arg Arg Ala Leu Pro Thr Pro
                5                   10                  15 gct gac gta gcc aca gtc aaa cag tac ctc gcc gaa ttg acc gtt gca     144
Ala Asp Val Ala Thr Val Lys Gln Tyr Leu Ala Glu Leu Thr Val Ala
            20                  25                  30 gaa cca gtg aag gaa cca cct ta  gtaaaaacct tctactttct cctacccgcg    197
Glu Pro Val Lys Glu Pro Pro Tyr
        35                  40 ctcaaaactg attcgaactt gaacag t gat cgc aaa aga ttt cca cac tgg      248
                               Asp Arg Lys Arg Phe Pro His Trp
                                                    45 ata tcc acc ggg ggt aaa tgt gat aca cga gag a gtaagtactc              292
Ile Ser Thr Gly Gly Lys Cys Asp Thr Arg Glu
50                  55                  60 tcatgctcag cttgggcgat gaggctaagc gtatactag tt  gtg tta tat cgg      345
                                              Ile Val Leu Tyr Arg
                                                              65 gac gga caa gac gtg act agg gat aag gaa tgc aga gct gtg tcg ggg     393
Asp Gly Gln Asp Val Thr Arg Asp Lys Glu Cys Arg Ala Val Ser Gly
                70                  75                  80 acc tgg ttt t gtacgtatgc gcccacccct caaagaaatg agtcttacat           443
Thr Trp Phe ctcatactag cc  gaa tac gac gga gca act tgg acc gac gca cta gac     491
                Ser Glu Tyr Asp Gly Ala Thr Trp Thr Asp Ala Leu Asp
                        85                  90                  95 tta gac atc gat cac gta att ccc ctc aaa gaa gga tgg gtg tct ggg     539
Leu Asp Ile Asp His Val Ile Pro Leu Lys Glu Gly Trp Val Ser Gly
            100                 105                 110 gcc tgg aac tgg aca acg gaa agg aga aaa atg ttt gcg aac gat ttg     587
Ala Trp Asn Trp Thr Thr Glu Arg Arg Lys Met Phe Ala Asn Asp Leu
        115                 120                 125 gtt agg ccg caa ttg att gct gtt acg gtaagtgcgt tcttccagga           634
Val Arg Pro Gln Leu Ile Ala Val Thr
130                 135 ctgaagcgag agataatcga acgtgtgtag gat aac gtg aat caa gca aaa gga    688
                                    Asp Asn Val Asn Gln Ala Lys Gly
                                                140                 145
```

```
gac aag gat cct gcg ctt tgg atg cct ccg ctt cag tca tat c        731
Asp Lys Asp Pro Ala Leu Trp Met Pro Pro Leu Gln Ser Tyr
        150                 155                 160 gtatggacta ccactaattg ctcaggcacc ggctaaccag gtacctctta g at  tgc  787
                                                            His Cys act tac att cgc gcg tgg atc gag gtt aaa cac ttc tac ga           828
Thr Tyr Ile Arg Ala Trp Ile Glu Val Lys His Phe Tyr Glu
        165                 170                 175 gtaagttttc atagcacata acctattgat agttaagtgt tgacgaattg actttcag g 887 ctg aac gtg aat cag gcg gaa aag gat gca ttg acg aat tat ctc ggt  935
Leu Asn Val Asn Gln Ala Glu Lys Asp Ala Leu Thr Asn Tyr Leu Gly
            180                 185                 190 aaa tgt gaa gaa gtt tca ttt gcg gtt gat gag ctg gtc ttg gga caa  983
Lys Cys Glu Glu Val Ser Phe Ala Val Asp Glu Leu Val Leu Gly Gln
        195                 200                 205 tga                                                              986
```

<210> SEQ ID NO 32
<211> LENGTH: 223
<212> TYPE: PRT
<213> ORGANISM: Rhizoctonia solani

<400> SEQUENCE: 32

```
Met His Phe Lys Tyr Leu Leu Ala Phe Ala Ser Leu Ala Thr Ala Ser
-15             -10                 -5                  -1  1

Pro Leu Ser Pro Ser Ser Gly Ile Gly Arg Arg Ala Leu Pro Thr Pro
            5                   10                  15

Ala Asp Val Ala Thr Val Lys Gln Tyr Leu Ala Glu Leu Thr Val Ala
        20                  25                  30

Glu Pro Val Lys Glu Pro Pro Tyr Asp Arg Lys Arg Phe Pro His Trp
    35                  40                  45

Ile Ser Thr Gly Gly Lys Cys Asp Thr Arg Glu Ile Val Leu Tyr Arg
50                  55                  60                  65

Asp Gly Gln Asp Val Thr Arg Asp Lys Glu Cys Arg Ala Val Ser Gly
            70                  75                  80

Thr Trp Phe Ser Glu Tyr Asp Gly Ala Thr Trp Thr Asp Ala Leu Asp
        85                  90                  95

Leu Asp Ile Asp His Val Ile Pro Leu Lys Glu Gly Trp Val Ser Gly
    100                 105                 110

Ala Trp Asn Trp Thr Thr Glu Arg Arg Lys Met Phe Ala Asn Asp Leu
115                 120                 125

Val Arg Pro Gln Leu Ile Ala Val Thr Asp Asn Val Asn Gln Ala Lys
130                 135                 140                 145

Gly Asp Lys Asp Pro Ala Leu Trp Met Pro Pro Leu Gln Ser Tyr His
            150                 155                 160

Cys Thr Tyr Ile Arg Ala Trp Ile Glu Val Lys His Phe Tyr Glu Leu
        165                 170                 175

Asn Val Asn Gln Ala Glu Lys Asp Ala Leu Thr Asn Tyr Leu Gly Lys
    180                 185                 190

Cys Glu Glu Val Ser Phe Ala Val Asp Glu Leu Val Leu Gly Gln
195                 200                 205
```

<210> SEQ ID NO 33
<211> LENGTH: 208
<212> TYPE: PRT
<213> ORGANISM: Rhizoctonia solani

<400> SEQUENCE: 33

```
Ser Pro Leu Ser Pro Ser Ser Gly Ile Gly Arg Arg Ala Leu Pro Thr
1               5                   10                  15
Pro Ala Asp Val Ala Thr Val Lys Gln Tyr Leu Ala Glu Leu Thr Val
            20                  25                  30
Ala Glu Pro Val Lys Glu Pro Pro Tyr Asp Arg Lys Arg Phe Pro His
        35                  40                  45
Trp Ile Ser Thr Gly Gly Lys Cys Asp Thr Arg Glu Ile Val Leu Tyr
    50                  55                  60
Arg Asp Gly Gln Asp Val Thr Arg Asp Lys Glu Cys Arg Ala Val Ser
65                  70                  75                  80
Gly Thr Trp Phe Ser Glu Tyr Asp Gly Ala Thr Trp Thr Asp Ala Leu
                85                  90                  95
Asp Leu Asp Ile Asp His Val Ile Pro Leu Lys Glu Gly Trp Val Ser
            100                 105                 110
Gly Ala Trp Asn Trp Thr Thr Glu Arg Arg Lys Met Phe Ala Asn Asp
        115                 120                 125
Leu Val Arg Pro Gln Leu Ile Ala Val Thr Asp Asn Val Asn Gln Ala
130                 135                 140
Lys Gly Asp Lys Asp Pro Ala Leu Trp Met Pro Pro Leu Gln Ser Tyr
145                 150                 155                 160
His Cys Thr Tyr Ile Arg Ala Trp Ile Glu Val Lys His Phe Tyr Glu
                165                 170                 175
Leu Asn Val Asn Gln Ala Glu Lys Asp Ala Leu Thr Asn Tyr Leu Gly
            180                 185                 190
Lys Cys Glu Glu Val Ser Phe Ala Val Asp Glu Leu Val Leu Gly Gln
        195                 200                 205
```

```
<210> SEQ ID NO 34
<211> LENGTH: 996
<212> TYPE: DNA
<213> ORGANISM: Rhizoctonia solani
<220> FEATURE:
<221> NAME/KEY: CDS
<222> LOCATION: (1)..(167)
<220> FEATURE:
<221> NAME/KEY: sig_peptide
<222> LOCATION: (1)..(45)
<220> FEATURE:
<221> NAME/KEY: mat_peptide
<222> LOCATION: (46)..(993)
<220> FEATURE:
<221> NAME/KEY: CDS
<222> LOCATION: (222)..(280)
<220> FEATURE:
<221> NAME/KEY: CDS
<222> LOCATION: (332)..(403)
<220> FEATURE:
<221> NAME/KEY: CDS
<222> LOCATION: (457)..(617)
<220> FEATURE:
<221> NAME/KEY: CDS
<222> LOCATION: (667)..(733)
<220> FEATURE:
<221> NAME/KEY: CDS
<222> LOCATION: (787)..(832)
<220> FEATURE:
<221> NAME/KEY: CDS
<222> LOCATION: (891)..(993)
```

<400> SEQUENCE: 34

```
atg tat ttc aag tat ctc ctt gca ttc gcc act cta gta tct gcc tcc    48
Met Tyr Phe Lys Tyr Leu Leu Ala Phe Ala Thr Leu Val Ser Ala Ser
```

```
              -15                 -10                 -5                  -1  1
ccg ctc aac ttc ggt cct gac atc gga cgt cgg gct ctt cca gcc ccg                    96
Pro Leu Asn Phe Gly Pro Asp Ile Gly Arg Arg Ala Leu Pro Ala Pro
              5                   10                                  15 gtg gat gta gcc aca gct aaa cag tac ctc aac gaa ctg gtc gtt gcg                   144
Val Asp Val Ala Thr Ala Lys Gln Tyr Leu Asn Glu Leu Val Val Ala
                  20                  25                  30 gag ccg gtg aac gat cct cct ta gtaagctcca tttccttccc ttgtacgttc                   197
Glu Pro Val Asn Asp Pro Pro Tyr
              35                  40 cgtagcttat ttgaacttgg gcag t aaa cgc act gca ttc ccg cac tgg ata                   249
                               Lys Arg Thr Ala Phe Pro His Trp Ile
                                            45                  50 tcc aca ggc ggt aaa tgt gac aca cga gag a gtaaatcccg ttcatgatta                   300
Ser Thr Gly Gly Lys Cys Asp Thr Arg Glu
                  55                  60 tagtgcgcgg ccttgctgag tgtgtgacta g tt gtg ttg tat cgg gac ggg                      351
                                     Ile Val Leu Tyr Arg Asp Gly
                                                         65 caa aac gtg act aga gat tca gaa tgc agg gcg gtg tcg ggg act tgg                   399
Gln Asn Val Thr Arg Asp Ser Glu Cys Arg Ala Val Ser Gly Thr Trp
              70                  75                  80 ttc t gtacgtatat gcccccacct tttgaggagt cctggtttta ttcttcaccc tag                   456
Phe cc gaa tac gac gga ggg aca tgg acc aat gcg ctg gat ctg gac att                    503
   Ser Glu Tyr Asp Gly Gly Thr Trp Thr Asn Ala Leu Asp Leu Asp Ile
   85                  90                  95                  100 gat cac gta gtt ccc ctc aaa gaa gga tgg ata tcc ggg gcc tgg aat                   551
Asp His Val Val Pro Leu Lys Glu Gly Trp Ile Ser Gly Ala Trp Asn
                  105                 110                 115 tgg aca aca gaa agg agg aag atg ttt gcg aat gat tta gtt agg ccg                   599
Trp Thr Thr Glu Arg Arg Lys Met Phe Ala Asn Asp Leu Val Arg Pro
              120                 125                 130 caa ctg att gct gtc acg gtgagcgtgt cccgctgggc taaaactggg                          647
Gln Leu Ile Ala Val Thr
              135 actaacagaa tgtgagcag gat aga gta aat caa gcc aaa ggg gac aag gat                   699
                      Asp Arg Val Asn Gln Ala Lys Gly Asp Lys Asp
                                  140                 145 cct gca cag tgg atg ccc ccc ctc caa tca tat c gtgagtcact                          743
Pro Ala Gln Trp Met Pro Pro Leu Gln Ser Tyr
150                 155                 160 atcactaaat acataaactt tgcccaactg aatactttgg tag at tgc act tac                    797
                                                    His Cys Thr Tyr att tgc gcg tgg atc gag gtc aaa cac ttc tac ga gtacgttctc                         842
Ile Cys Ala Trp Ile Glu Val Lys His Phe Tyr Glu
165                 170                 175 tattgtatat tacttaccgg gggcaaaaac tgacgggttt tctactag a tta cgt                    897
                                                         Leu Arg gtt aat acg gcg gaa aaa gcc gca ttg acg aac tat atc agt aaa tgc                   945
Val Asn Thr Ala Glu Lys Ala Ala Leu Thr Asn Tyr Ile Ser Lys Cys
              180                 185                 190 gac gtt ccc tct ttc gcg ggg gag gaa ttg gtc cta gga cac aat ttg                   993
Asp Val Pro Ser Phe Ala Gly Glu Glu Leu Val Leu Gly His Asn Leu
195                 200                 205                 210 taa                                                                               996

<210> SEQ ID NO 35
```

<211> LENGTH: 225
<212> TYPE: PRT
<213> ORGANISM: Rhizoctonia solani

<400> SEQUENCE: 35

```
Met Tyr Phe Lys Tyr Leu Leu Ala Phe Ala Thr Leu Val Ser Ala Ser
-15                 -10                 -5                  -1  1

Pro Leu Asn Phe Gly Pro Asp Ile Gly Arg Arg Ala Leu Pro Ala Pro
             5                  10                  15

Val Asp Val Ala Thr Ala Lys Gln Tyr Leu Asn Glu Leu Val Val Ala
            20                  25                  30

Glu Pro Val Asn Asp Pro Pro Tyr Lys Arg Thr Ala Phe Pro His Trp
        35                  40                  45

Ile Ser Thr Gly Gly Lys Cys Asp Thr Arg Glu Ile Val Leu Tyr Arg
50                  55                  60                  65

Asp Gly Gln Asn Val Thr Arg Asp Ser Glu Cys Arg Ala Val Ser Gly
                70                  75                  80

Thr Trp Phe Ser Glu Tyr Asp Gly Gly Thr Trp Thr Asn Ala Leu Asp
            85                  90                  95

Leu Asp Ile Asp His Val Val Pro Leu Lys Glu Gly Trp Ile Ser Gly
            100                 105                 110

Ala Trp Asn Trp Thr Thr Glu Arg Arg Lys Met Phe Ala Asn Asp Leu
        115                 120                 125

Val Arg Pro Gln Leu Ile Ala Val Thr Asp Arg Val Asn Gln Ala Lys
130                 135                 140                 145

Gly Asp Lys Asp Pro Ala Gln Trp Met Pro Pro Leu Gln Ser Tyr His
                150                 155                 160

Cys Thr Tyr Ile Cys Ala Trp Ile Glu Val Lys His Phe Tyr Glu Leu
            165                 170                 175

Arg Val Asn Thr Ala Glu Lys Ala Ala Leu Thr Asn Tyr Ile Ser Lys
            180                 185                 190

Cys Asp Val Pro Ser Phe Ala Gly Glu Glu Leu Val Leu Gly His Asn
        195                 200                 205

Leu
210
```

<210> SEQ ID NO 36
<211> LENGTH: 210
<212> TYPE: PRT
<213> ORGANISM: Rhizoctonia solani

<400> SEQUENCE: 36

```
Ser Pro Leu Asn Phe Gly Pro Asp Ile Gly Arg Arg Ala Leu Pro Ala
1               5                   10                  15

Pro Val Asp Val Ala Thr Ala Lys Gln Tyr Leu Asn Glu Leu Val Val
                20                  25                  30

Ala Glu Pro Val Asn Asp Pro Pro Tyr Lys Arg Thr Ala Phe Pro His
            35                  40                  45

Trp Ile Ser Thr Gly Gly Lys Cys Asp Thr Arg Glu Ile Val Leu Tyr
    50                  55                  60

Arg Asp Gly Gln Asn Val Thr Arg Asp Ser Glu Cys Arg Ala Val Ser
65                  70                  75                  80

Gly Thr Trp Phe Ser Glu Tyr Asp Gly Gly Thr Trp Thr Asn Ala Leu
                85                  90                  95

Asp Leu Asp Ile Asp His Val Val Pro Leu Lys Glu Gly Trp Ile Ser
            100                 105                 110
```

```
Gly Ala Trp Asn Trp Thr Thr Glu Arg Arg Lys Met Phe Ala Asn Asp
        115                 120                 125

Leu Val Arg Pro Gln Leu Ile Ala Val Thr Asp Arg Val Asn Gln Ala
    130                 135                 140

Lys Gly Asp Lys Asp Pro Ala Gln Trp Met Pro Pro Leu Gln Ser Tyr
145                 150                 155                 160

His Cys Thr Tyr Ile Cys Ala Trp Ile Glu Val Lys His Phe Tyr Glu
                165                 170                 175

Leu Arg Val Asn Thr Ala Glu Lys Ala Ala Leu Thr Asn Tyr Ile Ser
            180                 185                 190

Lys Cys Asp Val Pro Ser Phe Ala Gly Glu Leu Val Leu Gly His
        195                 200                 205

Asn Leu
    210

<210> SEQ ID NO 37
<211> LENGTH: 956
<212> TYPE: DNA
<213> ORGANISM: Rhizoctonia solani
<220> FEATURE:
<221> NAME/KEY: CDS
<222> LOCATION: (1)..(164)
<220> FEATURE:
<221> NAME/KEY: sig_peptide
<222> LOCATION: (1)..(51)
<220> FEATURE:
<221> NAME/KEY: mat_peptide
<222> LOCATION: (52)..(953)
<220> FEATURE:
<221> NAME/KEY: CDS
<222> LOCATION: (219)..(277)
<220> FEATURE:
<221> NAME/KEY: CDS
<222> LOCATION: (335)..(406)
<220> FEATURE:
<221> NAME/KEY: CDS
<222> LOCATION: (460)..(620)
<220> FEATURE:
<221> NAME/KEY: CDS
<222> LOCATION: (674)..(740)
<220> FEATURE:
<221> NAME/KEY: CDS
<222> LOCATION: (801)..(846)
<220> FEATURE:
<221> NAME/KEY: CDS
<222> LOCATION: (899)..(953)

<400> SEQUENCE: 37 atg ttg ttc aaa tat gtg gct ctt gca ttc ttt aca agc ctc gtc gcg      48
Met Leu Phe Lys Tyr Val Ala Leu Ala Phe Phe Thr Ser Leu Val Ala
        -15                 -10                 -5 ggt gct cct ctt gac tgg gag aac aag cga gcg ctc cca acg cct gtc      96
Gly Ala Pro Leu Asp Trp Glu Asn Lys Arg Ala Leu Pro Thr Pro Val
-1  1               5                   10                  15 agc gtt gct act gcg aag act tac ctt gcg gct ttg act gtg gag gca     144
Ser Val Ala Thr Ala Lys Thr Tyr Leu Ala Ala Leu Thr Val Glu Ala
                20                  25                  30 gaa tcc aac tcg ccg gct ta  gtgggtctcg ttatcatgaa gttatcatcc        194
Glu Ser Asn Ser Pro Ala Tyr
                35 gagattaacc tgattcactc tcag t gac cgt gat ctg ttc cct cat tgg atc    246
                             Asp Arg Asp Leu Phe Pro His Trp Ile
                                 40                  45 acc att tct gga aca tgc aat acc cgt gaa a gtatgtagcg atttagttaa     297
Thr Ile Ser Gly Thr Cys Asn Thr Arg Glu
```

```
            50                  55
ggcggtaggc aatatctcac cgaggcgatt tatgtag ct  gtt ttg aaa cgt gat      351
                                             Thr Val Leu Lys Arg Asp
                                                              60 ggc act aac gtt gtc acc gat tct gct tgt gcc tca acc tcc ggc acc      399
Gly Thr Asn Val Val Thr Asp Ser Ala Cys Ala Ser Thr Ser Gly Thr
 65                  70                  75 tgg aag t gtaagtgtga attattaaat gcccttccta acttactcaa gtggatgaaa     456
Trp Lys
 80 tag cc  gtt tat gac ggt gct acc tgg acc gcc gct tcc gat ctt gac      503
        Ser Val Tyr Asp Gly Ala Thr Trp Thr Ala Ala Ser Asp Leu Asp
                         85                  90                  95 att gac cac gtt gtt cca ctc aag gag gcc tgg gtc tct gga gct cgc      551
Ile Asp His Val Val Pro Leu Lys Glu Ala Trp Val Ser Gly Ala Arg
                100                 105                 110 agc tgg aca act gcc caa cga caa tcc ttt gcc aat gat ttg act cgt      599
Ser Trp Thr Thr Ala Gln Arg Gln Ser Phe Ala Asn Asp Leu Thr Arg
            115                 120                 125 cct cag ctt att gcc gtt acc gtgagtgaag gggagttgaa aaataacttg         650
Pro Gln Leu Ile Ala Val Thr
        130                 135 ggtagattat aacaatattt tag gac aac gtc aat caa tcc aag ggt gat aag    703
                          Asp Asn Val Asn Gln Ser Lys Gly Asp Lys
                                              140                 145 gac ccg gca gaa tgg atg ccc cct ctg tcc tct tac t gtcagtattt         750
Asp Pro Ala Glu Trp Met Pro Pro Leu Ser Ser Tyr
                150                 155 ttggttcaaa ttaacttcca ttttgctcat gaataactca ctgtttgtag ac  tgc       805
                                                         Tyr Cys acc tac gtt cgt gct tgg atc acc gtc aaa tac tac tac ga               846
Thr Tyr Val Arg Ala Trp Ile Thr Val Lys Tyr Tyr Tyr Asp
160                 165                 170 gtaagtcatt agatgtcaaa agttttaccc tggacttaca caattgttcc ag t ctc      902
                                                         Leu tcg gtg gac tct gct gaa aag tcg gca ctg aca tcc tac ctc aac aac      950
Ser Val Asp Ser Ala Glu Lys Ser Ala Leu Thr Ser Tyr Leu Asn Asn
    175                 180                 185                 190 tgt taa                                                              956
Cys

<210> SEQ ID NO 38
<211> LENGTH: 208
<212> TYPE: PRT
<213> ORGANISM: Rhizoctonia solani

<400> SEQUENCE: 38

Met Leu Phe Lys Tyr Val Ala Leu Ala Phe Phe Thr Ser Leu Val Ala
        -15                 -10                  -5

Gly Ala Pro Leu Asp Trp Glu Asn Lys Arg Ala Leu Pro Thr Pro Val
 -1  1               5                  10                  15

Ser Val Ala Thr Ala Lys Thr Tyr Leu Ala Ala Leu Thr Val Glu Ala
                20                  25                  30

Glu Ser Asn Ser Pro Ala Tyr Asp Arg Asp Leu Phe Pro His Trp Ile
            35                  40                  45

Thr Ile Ser Gly Thr Cys Asn Thr Arg Glu Thr Val Leu Lys Arg Asp
         50                  55                  60

Gly Thr Asn Val Val Thr Asp Ser Ala Cys Ala Ser Thr Ser Gly Thr
```

```
                65                  70                  75
Trp Lys Ser Val Tyr Asp Gly Ala Thr Trp Thr Ala Ala Ser Asp Leu
 80                  85                  90                  95

Asp Ile Asp His Val Val Pro Leu Lys Glu Ala Trp Val Ser Gly Ala
                100                 105                 110

Arg Ser Trp Thr Thr Ala Gln Arg Gln Ser Phe Ala Asn Asp Leu Thr
            115                 120                 125

Arg Pro Gln Leu Ile Ala Val Thr Asp Asn Val Asn Gln Ser Lys Gly
        130                 135                 140

Asp Lys Asp Pro Ala Glu Trp Met Pro Pro Leu Ser Ser Tyr Tyr Cys
    145                 150                 155

Thr Tyr Val Arg Ala Trp Ile Thr Val Lys Tyr Tyr Asp Leu Ser
160                 165                 170                 175

Val Asp Ser Ala Glu Lys Ser Ala Leu Thr Ser Tyr Leu Asn Asn Cys
                180                 185                 190
```

<210> SEQ ID NO 39
<211> LENGTH: 191
<212> TYPE: PRT
<213> ORGANISM: Rhizoctonia solani

<400> SEQUENCE: 39

```
Ala Pro Leu Asp Trp Glu Asn Lys Arg Ala Leu Pro Thr Pro Val Ser
 1               5                  10                  15

Val Ala Thr Ala Lys Thr Tyr Leu Ala Ala Leu Thr Val Glu Ala Glu
                20                  25                  30

Ser Asn Ser Pro Ala Tyr Asp Arg Asp Leu Phe Pro His Trp Ile Thr
            35                  40                  45

Ile Ser Gly Thr Cys Asn Thr Arg Glu Thr Val Leu Lys Arg Asp Gly
        50                  55                  60

Thr Asn Val Val Thr Asp Ser Ala Cys Ala Ser Thr Ser Gly Thr Trp
 65                  70                  75                  80

Lys Ser Val Tyr Asp Gly Ala Thr Trp Thr Ala Ala Ser Asp Leu Asp
                85                  90                  95

Ile Asp His Val Val Pro Leu Lys Glu Ala Trp Val Ser Gly Ala Arg
                100                 105                 110

Ser Trp Thr Thr Ala Gln Arg Gln Ser Phe Ala Asn Asp Leu Thr Arg
            115                 120                 125

Pro Gln Leu Ile Ala Val Thr Asp Asn Val Asn Gln Ser Lys Gly Asp
        130                 135                 140

Lys Asp Pro Ala Glu Trp Met Pro Pro Leu Ser Ser Tyr Tyr Cys Thr
145                 150                 155                 160

Tyr Val Arg Ala Trp Ile Thr Val Lys Tyr Tyr Tyr Asp Leu Ser Val
                165                 170                 175

Asp Ser Ala Glu Lys Ser Ala Leu Thr Ser Tyr Leu Asn Asn Cys
            180                 185                 190
```

<210> SEQ ID NO 40
<211> LENGTH: 998
<212> TYPE: DNA
<213> ORGANISM: Rhizoctonia solani
<220> FEATURE:
<221> NAME/KEY: CDS
<222> LOCATION: (1)..(167)
<220> FEATURE:
<221> NAME/KEY: sig_peptide
<222> LOCATION: (1)..(63)
<220> FEATURE:

```
<221> NAME/KEY: mat_peptide
<222> LOCATION: (64)..(995)
<220> FEATURE:
<221> NAME/KEY: CDS
<222> LOCATION: (224)..(282)
<220> FEATURE:
<221> NAME/KEY: CDS
<222> LOCATION: (332)..(403)
<220> FEATURE:
<221> NAME/KEY: CDS
<222> LOCATION: (454)..(614)
<220> FEATURE:
<221> NAME/KEY: CDS
<222> LOCATION: (668)..(734)
<220> FEATURE:
<221> NAME/KEY: CDS
<222> LOCATION: (786)..(831)
<220> FEATURE:
<221> NAME/KEY: CDS
<222> LOCATION: (887)..(995)

<400> SEQUENCE: 40
```

| | | | | | | | | | | | | | | | | |
|---|---|---|---|---|---|---|---|---|---|---|---|---|---|---|---|---|
| atg | cac | ctc | agc | tac | ctc | ctt | gca | ctt | gcc | tct | ctt | ata | acc | gct | tcg | 48 |
| Met | His | Leu | Ser | Tyr | Leu | Leu | Ala | Leu | Ala | Ser | Leu | Ile | Thr | Ala | Ser | |
| | -20 | | | | -15 | | | | | -10 | | | | | | |

| | | | | | | | | | | | | | | | | |
|---|---|---|---|---|---|---|---|---|---|---|---|---|---|---|---|---|
| cca | cta | ggc | tta | agt | tct | gga | att | agg | cgt | cga | gaa | ctt | ccg | tct | cca | 96 |
| Pro | Leu | Gly | Leu | Ser | Ser | Gly | Ile | Arg | Arg | Arg | Glu | Leu | Pro | Ser | Pro | |
| -5 | | | | | -1  1 | | | | 5 | | | | | 10 | | |

| | | | | | | | | | | | | | | | | |
|---|---|---|---|---|---|---|---|---|---|---|---|---|---|---|---|---|
| gtg | gag | gtg | gat | gta | gct | aaa | caa | tac | ctc | gct | aaa | ttg | gtt | gtt | gct | 144 |
| Val | Glu | Val | Asp | Val | Ala | Lys | Gln | Tyr | Leu | Ala | Lys | Leu | Val | Val | Ala | |
| | | 15 | | | | | 20 | | | | | 25 | | | | |

| | | | | | | | |
|---|---|---|---|---|---|---|---|
| gag | cca | gtg | ctc | aac | cct | cct | ta   gtaaatttca ccctacactc cccatttgta | 197 |
| Glu | Pro | Val | Leu | Asn | Pro | Pro | Tyr | |
| | 30 | | | | | 35 | | |

| | | | | | | | | | |
|---|---|---|---|---|---|---|---|---|---|
| gctcattaat atttaacatt tcacag t | gac | cgt | aaa | aaa | ttc | cca | cat | tgg | 248 |
| | Asp | Arg | Lys | Lys | Phe | Pro | His | Trp | |
| | | | | 40 | | | | | |

| | | | | | | | | | |
|---|---|---|---|---|---|---|---|---|---|
| ata | tct | act | ggt | ggt | aaa | tgc | gat | aca | cga | gag c gtgagtcctt | 292 |
| Ile | Ser | Thr | Gly | Gly | Lys | Cys | Asp | Thr | Arg | Glu | |
| | | 45 | | | | | 50 | | | | |

| | | | | | | | | |
|---|---|---|---|---|---|---|---|---|
| gtacagctct acaccgcaat gaactaatca tgcaaccag tt | gtg | ctg | tat | cgt | 345 |
| | Leu | Val | Leu | Tyr | Arg | |
| | | | | 55 | | |

| | | | | | | | | | | | | | | | | |
|---|---|---|---|---|---|---|---|---|---|---|---|---|---|---|---|---|
| gac | ggg | cag | aat | gta | acc | cgg | gac | tcg | cag | tgt | aga | gcc | gta | gca | ggg | 393 |
| Asp | Gly | Gln | Asn | Val | Thr | Arg | Asp | Ser | Gln | Cys | Arg | Ala | Val | Ala | Gly | |
| 60 | | | | | 65 | | | | | 70 | | | | | 75 | |

| | | | | | |
|---|---|---|---|---|---|
| acc | tgg | ttt | t | gtgagtgacc aagtatttcg ttgaaatatt gacgttgaaa | 443 |
| Thr | Trp | Phe | | | |

| | | | | | | | | | | | | | |
|---|---|---|---|---|---|---|---|---|---|---|---|---|---|
| tctttggtag ct | gag | tac | gac | ggt | gca | acc | tgg | aca | gat | gcg | ctg | gac | 491 |
| | Ser | Glu | Tyr | Asp | Gly | Ala | Thr | Trp | Thr | Asp | Ala | Leu | Asp | |
| | | 80 | | | | | 85 | | | | | 90 | | |

| | | | | | | | | | | | | | | | | |
|---|---|---|---|---|---|---|---|---|---|---|---|---|---|---|---|---|
| cta | gac | att | gac | cac | gtc | gta | ccc | ttg | aaa | gaa | gga | tgg | ata | tca | ggc | 539 |
| Leu | Asp | Ile | Asp | His | Val | Val | Pro | Leu | Lys | Glu | Gly | Trp | Ile | Ser | Gly | |
| | | 95 | | | | | 100 | | | | | 105 | | | | |

| | | | | | | | | | | | | | | | | |
|---|---|---|---|---|---|---|---|---|---|---|---|---|---|---|---|---|
| gct | tgg | aat | tgg | acg | acc | gaa | aga | aga | aag | atg | ttt | gca | aac | gat | cta | 587 |
| Ala | Trp | Asn | Trp | Thr | Thr | Glu | Arg | Arg | Lys | Met | Phe | Ala | Asn | Asp | Leu | |
| | | | 110 | | | | | 115 | | | | | 120 | | | |

| | | | | | | | | |
|---|---|---|---|---|---|---|---|---|
| gtt | aga | ccc | caa | ttg | att | gca | gtg | act | gtgagtgcag ctttcttgga | 634 |
| Val | Arg | Pro | Gln | Leu | Ile | Ala | Val | Thr | |
| | | 125 | | | | | 130 | | |

| | | | | | | | |
|---|---|---|---|---|---|---|---|
| atggggcgcg aacgcaccaa caaaagtgag cag | gat | aat | gtc | aac | caa | gcg | aag | 688 |
| | Asp | Asn | Val | Asn | Gln | Ala | Lys | |
| | | | | 135 | | | | |

| | | | | | | | | | | | |
|---|---|---|---|---|---|---|---|---|---|---|---|
| gga | gat | aag | gat | cct | gct | act | tgg | atg | ccc | cct | ctt | caa | tcc | tat | c | 734 |

```
                    Gly Asp Lys Asp Pro Ala Thr Trp Met Pro Pro Leu Gln Ser Tyr
                    140                 145                 150 gtaggttttc cctgctaatt ctttaggcct ttgctaatcg gataacgaca g  at  tgt        790
                                                          His Cys
                                                              155 act tat att cgt gca tgg atc gag gtc aaa cac ttc tac ga                   831
Thr Tyr Ile Arg Ala Trp Ile Glu Val Lys His Phe Tyr Glu
            160                 165                 170 gtatgcaaat catcaaacga ggttaattag agaataacta acaattaccc tttag g           887 ctg gcc att cat cca gcg gaa aaa acc gca tta aca aat tac ctt agc          935
Leu Ala Ile His Pro Ala Glu Lys Thr Ala Leu Thr Asn Tyr Leu Ser
                175                 180                 185 aaa tgc gag acg cct act ttt gta agc gag gag tta gtt ctg gcg ccc          983
Lys Cys Glu Thr Pro Thr Phe Val Ser Glu Glu Leu Val Leu Ala Pro
            190                 195                 200 gat atg cag aag taa                                                      998
Asp Met Gln Lys
        205

<210> SEQ ID NO 41
<211> LENGTH: 227
<212> TYPE: PRT
<213> ORGANISM: Rhizoctonia solani

<400> SEQUENCE: 41

Met His Leu Ser Tyr Leu Leu Ala Leu Ala Ser Leu Ile Thr Ala Ser
    -20                 -15                 -10

Pro Leu Gly Leu Ser Ser Gly Ile Arg Arg Arg Glu Leu Pro Ser Pro
-5              -1  1               5                   10

Val Glu Val Asp Val Ala Lys Gln Tyr Leu Ala Lys Leu Val Val Ala
            15                  20                  25

Glu Pro Val Leu Asn Pro Pro Tyr Asp Arg Lys Lys Phe Pro His Trp
            30                  35                  40

Ile Ser Thr Gly Gly Lys Cys Asp Thr Arg Glu Leu Val Leu Tyr Arg
    45                  50                  55

Asp Gly Gln Asn Val Thr Arg Asp Ser Gln Cys Arg Ala Val Ala Gly
60                  65                  70                  75

Thr Trp Phe Ser Glu Tyr Asp Gly Ala Thr Trp Thr Asp Ala Leu Asp
            80                  85                  90

Leu Asp Ile Asp His Val Val Pro Leu Lys Glu Gly Trp Ile Ser Gly
            95                  100                 105

Ala Trp Asn Trp Thr Thr Glu Arg Arg Lys Met Phe Ala Asn Asp Leu
    110                 115                 120

Val Arg Pro Gln Leu Ile Ala Val Thr Asp Asn Val Asn Gln Ala Lys
    125                 130                 135

Gly Asp Lys Asp Pro Ala Thr Trp Met Pro Pro Leu Gln Ser Tyr His
140                 145                 150                 155

Cys Thr Tyr Ile Arg Ala Trp Ile Glu Val Lys His Phe Tyr Glu Leu
            160                 165                 170

Ala Ile His Pro Ala Glu Lys Thr Ala Leu Thr Asn Tyr Leu Ser Lys
            175                 180                 185

Cys Glu Thr Pro Thr Phe Val Ser Glu Glu Leu Val Leu Ala Pro Asp
            190                 195                 200

Met Gln Lys
    205
```

<210> SEQ ID NO 42
<211> LENGTH: 206
<212> TYPE: PRT
<213> ORGANISM: Rhizoctonia solani

<400> SEQUENCE: 42

Ser Gly Ile Arg Arg Arg Glu Leu Pro Ser Pro Val Glu Val Asp Val
1               5                   10                  15

Ala Lys Gln Tyr Leu Ala Lys Leu Val Val Ala Glu Pro Val Leu Asn
            20                  25                  30

Pro Pro Tyr Asp Arg Lys Lys Phe Pro His Trp Ile Ser Thr Gly Gly
        35                  40                  45

Lys Cys Asp Thr Arg Glu Leu Val Leu Tyr Arg Asp Gly Gln Asn Val
50                  55                  60

Thr Arg Asp Ser Gln Cys Arg Ala Val Ala Gly Thr Trp Phe Ser Glu
65                  70                  75                  80

Tyr Asp Gly Ala Thr Trp Thr Asp Ala Leu Asp Leu Asp Ile Asp His
                85                  90                  95

Val Val Pro Leu Lys Glu Gly Trp Ile Ser Gly Ala Trp Asn Trp Thr
            100                 105                 110

Thr Glu Arg Arg Lys Met Phe Ala Asn Asp Leu Val Arg Pro Gln Leu
        115                 120                 125

Ile Ala Val Thr Asp Asn Val Asn Gln Ala Lys Gly Asp Lys Asp Pro
130                 135                 140

Ala Thr Trp Met Pro Pro Leu Gln Ser Tyr His Cys Thr Tyr Ile Arg
145                 150                 155                 160

Ala Trp Ile Glu Val Lys His Phe Tyr Glu Leu Ala Ile His Pro Ala
                165                 170                 175

Glu Lys Thr Ala Leu Thr Asn Tyr Leu Ser Lys Cys Gly Thr Pro Thr
            180                 185                 190

Phe Val Ser Glu Glu Leu Val Leu Ala Pro Asp Met Gln Lys
        195                 200                 205

<210> SEQ ID NO 43
<211> LENGTH: 988
<212> TYPE: DNA
<213> ORGANISM: Rhizoctonia solani
<220> FEATURE:
<221> NAME/KEY: CDS
<222> LOCATION: (1)..(167)
<220> FEATURE:
<221> NAME/KEY: sig_peptide
<222> LOCATION: (1)..(45)
<220> FEATURE:
<221> NAME/KEY: mat_peptide
<222> LOCATION: (46)..(985)
<220> FEATURE:
<221> NAME/KEY: CDS
<222> LOCATION: (222)..(280)
<220> FEATURE:
<221> NAME/KEY: CDS
<222> LOCATION: (332)..(403)
<220> FEATURE:
<221> NAME/KEY: CDS
<222> LOCATION: (455)..(615)
<220> FEATURE:
<221> NAME/KEY: CDS
<222> LOCATION: (666)..(732)
<220> FEATURE:
<221> NAME/KEY: CDS
<222> LOCATION: (782)..(827)
<220> FEATURE:
<221> NAME/KEY: CDS
<222> LOCATION: (883)..(985)

```
<400> SEQUENCE: 43 atg cat ttt cgt ttt ctc ttt gcc ttt gcc tct ctg att aca gct tct        48
Met His Phe Arg Phe Leu Phe Ala Phe Ala Ser Leu Ile Thr Ala Ser
-15             -10                 -5                  -1  1 cct atc acc ttc aat act ggt atc gaa ctc aga gca ctt cca acg cca        96
Pro Ile Thr Phe Asn Thr Gly Ile Glu Leu Arg Ala Leu Pro Thr Pro
            5                   10                  15 gcg gat gca gcc aca gtc aaa caa tac ctc gct gaa ttg gcc gtt gcc       144
Ala Asp Ala Ala Thr Val Lys Gln Tyr Leu Ala Glu Leu Ala Val Ala
        20                  25                  30 gag cct gtt act caa cca cct ta gtgaatattc tcattgttcc atgcgcgttt       197
Glu Pro Val Thr Gln Pro Pro Tyr
    35                  40 catggctaac ttccatccga aaag t aaa cgc act gaa ttc cca cac tgg ata       249
                              Lys Arg Thr Glu Phe Pro His Trp Ile
                                          45                  50 agt acc ggc ggt aaa tgt gac aca cga gaa c gtgagtcttg ctcgtgtcca       300
Ser Thr Gly Gly Lys Cys Asp Thr Arg Glu
            55                  60 tttggaaggt tggtattaag cgcgtgatta g tt gtg ttg tat agg gac ggt          351
                                    Leu Val Leu Tyr Arg Asp Gly
                                                        65 caa aat gtg aca aga gac tcc gag tgc aga gcc gtt tca gga acc tgg       399
Gln Asn Val Thr Arg Asp Ser Glu Cys Arg Ala Val Ser Gly Thr Trp
        70                  75                  80 ttc t gtacgtacct attttccgct ctatcagcct taatctgatc atatgtatta g        454
Phe cg gaa tat gac gcc aaa aca tgg aac gat cct cag cgc ctc gat ata        501
   Ser Glu Tyr Asp Ala Lys Thr Trp Asn Asp Pro Gln Arg Leu Asp Ile
85                  90                  95                  100 gac cac gtc gtc cct ctc aag gaa gga tgg gga gcc gga gca tgg aac       549
Asp His Val Val Pro Leu Lys Glu Gly Trp Gly Ala Gly Ala Trp Asn
                105                 110                 115 tgg act cgc gaa aag aga aga atg ttt gcg aac gat tta gtt agg ccg       597
Trp Thr Arg Glu Lys Arg Arg Met Phe Ala Asn Asp Leu Val Arg Pro
            120                 125                 130 caa cta att gcc gtt acc gtaagtgaga tttttggcgt gaggttaggg              645
Gln Leu Ile Ala Val Thr
            135 tgatattgat agctgggtag gat acc gtg aac caa gca aaa ggg gat aaa gat     698
                      Asp Thr Val Asn Gln Ala Lys Gly Asp Lys Asp
                                  140                 145 cct gcg ctc tgg atg cca cca ctt ccg tcc tac c gtaagacgct              742
Pro Ala Leu Trp Met Pro Pro Leu Pro Ser Tyr
150                 155                 160 ataaccaaac ttgtacttca actaattggt tatcggcag at tgc act tac att         795
                                            His Cys Thr Tyr Ile
                                                        165 cgc gcg tgg atc gag gtc aaa cac ttt tac ga gtgagtcatt tataatgtgc     847
Arg Ala Trp Ile Glu Val Lys His Phe Tyr Glu
            170                 175 tctcaaccca tgggagttga ccagtcggta cccag g ctg agt gtg aac gag gcg     901
                                       Leu Ser Val Asn Glu Ala
                                                    180 gag aaa acc gca ttg acg aac tat ctc agt aaa tgc gag aag gtt gct      949
Glu Lys Thr Ala Leu Thr Asn Tyr Leu Ser Lys Cys Glu Lys Val Ala
            185                 190                 195 ttc gcc agc gac gag cta gtc ctt ggg aat gac ttg taa                   988
Phe Ala Ser Asp Glu Leu Val Leu Gly Asn Asp Leu
```

200          205          210

<210> SEQ ID NO 44
<211> LENGTH: 225
<212> TYPE: PRT
<213> ORGANISM: Rhizoctonia solani

<400> SEQUENCE: 44

Met His Phe Arg Phe Leu Phe Ala Phe Ala Ser Leu Ile Thr Ala Ser
-15                 -10                 -5                  -1  1

Pro Ile Thr Phe Asn Thr Gly Ile Glu Leu Arg Ala Leu Pro Thr Pro
                5                   10                  15

Ala Asp Ala Ala Thr Val Lys Gln Tyr Leu Ala Glu Leu Ala Val Ala
            20                  25                  30

Glu Pro Val Thr Gln Pro Pro Tyr Lys Arg Thr Glu Phe Pro His Trp
        35                  40                  45

Ile Ser Thr Gly Gly Lys Cys Asp Thr Arg Glu Leu Val Leu Tyr Arg
50                  55                  60                  65

Asp Gly Gln Asn Val Thr Arg Asp Ser Glu Cys Arg Ala Val Ser Gly
                70                  75                  80

Thr Trp Phe Ser Glu Tyr Asp Ala Lys Thr Trp Asn Asp Pro Gln Arg
            85                  90                  95

Leu Asp Ile Asp His Val Val Pro Leu Lys Glu Gly Trp Gly Ala Gly
        100                 105                 110

Ala Trp Asn Trp Thr Arg Glu Lys Arg Arg Met Phe Ala Asn Asp Leu
    115                 120                 125

Val Arg Pro Gln Leu Ile Ala Val Thr Asp Thr Val Asn Gln Ala Lys
130                 135                 140                 145

Gly Asp Lys Asp Pro Ala Leu Trp Met Pro Pro Leu Pro Ser Tyr His
                150                 155                 160

Cys Thr Tyr Ile Arg Ala Trp Ile Glu Val Lys His Phe Tyr Glu Leu
            165                 170                 175

Ser Val Asn Glu Ala Glu Lys Thr Ala Leu Thr Asn Tyr Leu Ser Lys
        180                 185                 190

Cys Glu Lys Val Ala Phe Ala Ser Asp Glu Leu Val Leu Gly Asn Asp
    195                 200                 205

Leu
210

<210> SEQ ID NO 45
<211> LENGTH: 210
<212> TYPE: PRT
<213> ORGANISM: Rhizoctonia solani

<400> SEQUENCE: 45

Ser Pro Ile Thr Phe Asn Thr Gly Ile Glu Leu Arg Ala Leu Pro Thr
1               5                   10                  15

Pro Ala Asp Ala Ala Thr Val Lys Gln Tyr Leu Ala Glu Leu Ala Val
            20                  25                  30

Ala Glu Pro Val Thr Gln Pro Pro Tyr Lys Arg Thr Glu Phe Pro His
        35                  40                  45

Trp Ile Ser Thr Gly Gly Lys Cys Asp Thr Arg Glu Leu Val Leu Tyr
    50                  55                  60

Arg Asp Gly Gln Asn Val Thr Arg Asp Ser Glu Cys Arg Ala Val Ser
65                  70                  75                  80

Gly Thr Trp Phe Ser Glu Tyr Asp Ala Lys Thr Trp Asn Asp Pro Gln

```
                  85                  90                  95
Arg Leu Asp Ile Asp His Val Val Pro Leu Lys Glu Gly Trp Gly Ala
            100                 105                 110

Gly Ala Trp Asn Trp Thr Arg Glu Lys Arg Met Phe Ala Asn Asp
        115                 120                 125

Leu Val Arg Pro Gln Leu Ile Ala Val Thr Asp Thr Val Asn Gln Ala
130                 135                 140

Lys Gly Asp Lys Asp Pro Ala Leu Trp Met Pro Pro Leu Pro Ser Tyr
145                 150                 155                 160

His Cys Thr Tyr Ile Arg Ala Trp Ile Glu Val Lys His Phe Tyr Glu
            165                 170                 175

Leu Ser Val Asn Glu Ala Glu Lys Thr Ala Leu Thr Asn Tyr Leu Ser
            180                 185                 190

Lys Cys Glu Lys Val Ala Phe Ala Ser Asp Leu Val Leu Gly Asn
            195                 200                 205

Asp Leu
    210

<210> SEQ ID NO 46
<211> LENGTH: 955
<212> TYPE: DNA
<213> ORGANISM: Rhizoctonia solani
<220> FEATURE:
<221> NAME/KEY: CDS
<222> LOCATION: (1)..(170)
<220> FEATURE:
<221> NAME/KEY: sig_peptide
<222> LOCATION: (1)..(54)
<220> FEATURE:
<221> NAME/KEY: mat_peptide
<222> LOCATION: (55)..(952)
<220> FEATURE:
<221> NAME/KEY: CDS
<222> LOCATION: (222)..(280)
<220> FEATURE:
<221> NAME/KEY: CDS
<222> LOCATION: (335)..(409)
<220> FEATURE:
<221> NAME/KEY: CDS
<222> LOCATION: (464)..(624)
<220> FEATURE:
<221> NAME/KEY: CDS
<222> LOCATION: (682)..(748)
<220> FEATURE:
<221> NAME/KEY: CDS
<222> LOCATION: (798)..(843)
<220> FEATURE:
<221> NAME/KEY: CDS
<222> LOCATION: (898)..(952)

<400> SEQUENCE: 46 atg tac ttg ata tcc tgg acc cta cta ctc gct ctg gtc gcc cta acc      48
Met Tyr Leu Ile Ser Trp Thr Leu Leu Leu Ala Leu Val Ala Leu Thr
            -15                 -10                 -5 act gcc tcc cca ctc aac ttt gac ctc gag agt cgc cag ctc ccg act      96
Thr Ala Ser Pro Leu Asn Phe Asp Leu Glu Ser Arg Gln Leu Pro Thr
   -1  1               5                  10 ccg gtt agc ata gcg acg gca aag gaa tac ctt gat gga cta gaa gtg     144
Pro Val Ser Ile Ala Thr Ala Lys Glu Tyr Leu Asp Gly Leu Glu Val
15                  20                  25                  30 gcc ttc cca gtg act gag ccc tcc ta gtaaatactc aagtatccag             190
Ala Phe Pro Val Thr Glu Pro Ser Tyr
                35 tacacgcccc agctgattca gaattgaaca g t gat cgc aaa gcc ttc cgg cac     243
                                    Asp Arg Lys Ala Phe Arg His
```

```
                                      40                  45
tgg ata cct atc gac ggt aaa tgc gat aca cga gaa a gtgaacatct      290
Trp Ile Pro Ile Asp Gly Lys Cys Asp Thr Arg Glu
             50                  55 tacatttcaa tcattatatg tgacaagact aattgtccga ccag ct  gta ttg aaa  345
                                              Thr Val Leu Lys
                                                       60 cgg gac gca aag gcg gaa ata gta gta gac tca gaa tgc aaa gcc acg  393
Arg Asp Ala Lys Ala Glu Ile Val Val Asp Ser Glu Cys Lys Ala Thr
         65                  70                  75 acg ggt gat tgg atc t gtacgcacat tcctcttttg caaatcacct agtcacttac 449
Thr Gly Asp Trp Ile
         80 tagttccccg ccag ct  ggc tat gat agc aaa tcg ata atg aat gca cac  498
                    Ser Gly Tyr Asp Ser Lys Ser Ile Met Asn Ala His
                                 85                  90                  95 gaa ctg gac atc gat cac cta gtt cca ctc aaa gaa gca tgg gga gcc  546
Glu Leu Asp Ile Asp His Leu Val Pro Leu Lys Glu Ala Trp Gly Ala
                 100                 105                 110 gga gct tgg aat tgg acg gct gaa agg aga aaa gag ttt gca aac gat  594
Gly Ala Trp Asn Trp Thr Ala Glu Arg Arg Lys Glu Phe Ala Asn Asp
             115                 120                 125 ttg act cgg ccc cag ttg ctc gcc gtt tcc gtaagtttgt ttctttttctt   644
Leu Thr Arg Pro Gln Leu Leu Ala Val Ser
         130                 135 cctcaagttg gaatcgtgaa agctaaagca catgtag gca acg tca aat cgg atg  699
                                         Ala Thr Ser Asn Arg Met
                                                             140 aaa ggg gat agg gac cct tcc aag tgg atg ccc tcg aat ccg tcg ttt c  748
Lys Gly Asp Arg Asp Pro Ser Lys Trp Met Pro Ser Asn Pro Ser Phe
     145                 150                 155 gtatgtcttt attagttgaa aactggctct gcttgctgat ccgagatag at  tgt acc 805
                                                         His Cys Thr
                                                             160 tat atc cgc tca tgg atc cag gta aaa cag tat tac ga  gtaagcttct  853
Tyr Ile Arg Ser Trp Ile Gln Val Lys Gln Tyr Tyr Glu
     165                 170                 175 gtactgttca tacgcagact cgggttgacc aagtgtatgt ttag a tta act gtg  907
                                                    Leu Thr Val gac caa gct gag aaa gaa gca cta aca aga tat atc aac gag tgt tga  955
Asp Gln Ala Glu Lys Glu Ala Leu Thr Arg Tyr Ile Asn Glu Cys
         180                 185                 190

<210> SEQ ID NO 47
<211> LENGTH: 211
<212> TYPE: PRT
<213> ORGANISM: Rhizoctonia solani

<400> SEQUENCE: 47

Met Tyr Leu Ile Ser Trp Thr Leu Leu Leu Ala Leu Val Ala Leu Thr
             -15                 -10                  -5

Thr Ala Ser Pro Leu Asn Phe Asp Leu Glu Ser Arg Gln Leu Pro Thr
 -1   1               5                  10

Pro Val Ser Ile Ala Thr Ala Lys Glu Tyr Leu Asp Gly Leu Glu Val
 15                  20                  25                  30

Ala Phe Pro Val Thr Glu Pro Ser Tyr Asp Arg Lys Ala Phe Arg His
                 35                  40                  45

Trp Ile Pro Ile Asp Gly Lys Cys Asp Thr Arg Glu Thr Val Leu Lys
             50                  55                  60
```

```
Arg Asp Ala Lys Ala Glu Ile Val Val Asp Ser Glu Cys Lys Ala Thr
            65                  70                  75

Thr Gly Asp Trp Ile Ser Gly Tyr Asp Ser Lys Ser Ile Met Asn Ala
        80                  85                  90

His Glu Leu Asp Ile Asp His Leu Val Pro Leu Lys Glu Ala Trp Gly
 95                 100                 105                 110

Ala Gly Ala Trp Asn Trp Thr Ala Glu Arg Arg Lys Glu Phe Ala Asn
                115                 120                 125

Asp Leu Thr Arg Pro Gln Leu Leu Ala Val Ser Ala Thr Ser Asn Arg
                130                 135                 140

Met Lys Gly Asp Arg Asp Pro Ser Lys Trp Met Pro Ser Asn Pro Ser
                145                 150                 155

Phe His Cys Thr Tyr Ile Arg Ser Trp Ile Gln Val Lys Gln Tyr Tyr
                160                 165                 170

Glu Leu Thr Val Asp Gln Ala Glu Lys Glu Ala Leu Thr Arg Tyr Ile
175                 180                 185                 190

Asn Glu Cys

<210> SEQ ID NO 48
<211> LENGTH: 193
<212> TYPE: PRT
<213> ORGANISM: Rhizoctonia solani

<400> SEQUENCE: 48

Ser Pro Leu Asn Phe Asp Leu Glu Ser Arg Gln Leu Pro Thr Pro Val
 1               5                  10                  15

Ser Ile Ala Thr Ala Lys Glu Tyr Leu Asp Gly Leu Glu Val Ala Phe
                20                  25                  30

Pro Val Thr Glu Pro Ser Tyr Asp Arg Lys Ala Phe Arg His Trp Ile
                35                  40                  45

Pro Ile Asp Gly Lys Cys Asp Thr Arg Glu Thr Val Leu Lys Arg Asp
            50                  55                  60

Ala Lys Ala Glu Ile Val Val Asp Ser Glu Cys Lys Ala Thr Thr Gly
65                  70                  75                  80

Asp Trp Ile Ser Gly Tyr Asp Ser Lys Ser Ile Met Asn Ala His Glu
                85                  90                  95

Leu Asp Ile Asp His Leu Val Pro Leu Lys Glu Ala Trp Gly Ala Gly
                100                 105                 110

Ala Trp Asn Trp Thr Ala Glu Arg Arg Lys Glu Phe Ala Asn Asp Leu
            115                 120                 125

Thr Arg Pro Gln Leu Leu Ala Val Ser Ala Thr Ser Asn Arg Met Lys
    130                 135                 140

Gly Asp Arg Asp Pro Ser Lys Trp Met Pro Ser Asn Pro Ser Phe His
145                 150                 155                 160

Cys Thr Tyr Ile Arg Ser Trp Ile Gln Val Lys Gln Tyr Tyr Glu Leu
                165                 170                 175

Thr Val Asp Gln Ala Glu Lys Glu Ala Leu Thr Arg Tyr Ile Asn Glu
                180                 185                 190

Cys

<210> SEQ ID NO 49
<211> LENGTH: 1002
<212> TYPE: DNA
<213> ORGANISM: Rhizoctonia solani
<220> FEATURE:
```

```
<221> NAME/KEY: CDS
<222> LOCATION: (1)..(167)
<220> FEATURE:
<221> NAME/KEY: sig_peptide
<222> LOCATION: (1)..(45)
<220> FEATURE:
<221> NAME/KEY: mat_peptide
<222> LOCATION: (46)..(999)
<220> FEATURE:
<221> NAME/KEY: CDS
<222> LOCATION: (220)..(278)
<220> FEATURE:
<221> NAME/KEY: CDS
<222> LOCATION: (330)..(401)
<220> FEATURE:
<221> NAME/KEY: CDS
<222> LOCATION: (457)..(617)
<220> FEATURE:
<221> NAME/KEY: CDS
<222> LOCATION: (672)..(738)
<220> FEATURE:
<221> NAME/KEY: CDS
<222> LOCATION: (790)..(835)
<220> FEATURE:
<221> NAME/KEY: CDS
<222> LOCATION: (897)..(999)

<400> SEQUENCE: 49
```

```
atg tac ctc aac tat ctc ttc gca ctt gct act ctc gca gcc gct tcg      48
Met Tyr Leu Asn Tyr Leu Phe Ala Leu Ala Thr Leu Ala Ala Ala Ser
-15             -10                 -5                  -1  1 ccg ctc ggt ttg gac tct gga gtt ggg cgt cgt gca ctt ccg tcc cca      96
Pro Leu Gly Leu Asp Ser Gly Val Gly Arg Arg Ala Leu Pro Ser Pro
                5                   10                  15 gta gac aca gcc gtg gct aaa cag tac ctc gct gaa ttg gtt gtt gct     144
Val Asp Thr Ala Val Ala Lys Gln Tyr Leu Ala Glu Leu Val Val Ala
            20                  25                  30 cag cca gtg ctc agt cct cct ta  gttagttcta tctctctcct tatcttctct    197
Gln Pro Val Leu Ser Pro Pro Tyr
        35                  40 aagctaattc aatactcgac ag t gac cgc aaa aaa ttc ccg cac tgg ata       247
                         Asp Arg Lys Lys Phe Pro His Trp Ile
                                      45                  50 tct act ggt ggc aaa tgt gac aca cgg gag c gtgagttctt aggaggttca     298
Ser Thr Gly Gly Lys Cys Asp Thr Arg Glu
                55                  60 cgttacgtgc atggactgac catatgatta g tg  gtg ctg tat cgt gac gga      349
                                     Leu Val Leu Tyr Arg Asp Gly
                                                          65 caa aac gta act aga gac tca gag tgc aga gcc gta gct ggc act tgg     397
Gln Asn Val Thr Arg Asp Ser Glu Cys Arg Ala Val Ala Gly Thr Trp
            70                  75                  80 ttc t gtgagtaagc gccttccgct tctcagatgc aaaccttgac agtttctcgg        451
Phe gttag ct  gaa tat gac ggt aaa agt tgg acc aat gcg ctg gac ctt gac   500
          Ser Glu Tyr Asp Gly Lys Ser Trp Thr Asn Ala Leu Asp Leu Asp
              85                  90                  95 ata gat cac gtc gtg cct cta aaa gaa gga tgg gta tcc gga gcc tgg     548
Ile Asp His Val Val Pro Leu Lys Glu Gly Trp Val Ser Gly Ala Trp
100                 105                 110                 115 aac tgg acg acc gag agg aga agg atg ttc gca aat gat ctg gtt agg     596
Asn Trp Thr Thr Glu Arg Arg Arg Met Phe Ala Asn Asp Leu Val Arg
                120                 125                 130 ccg cag ttg att gct gtc acc gtgagtgtaa taatgttggg caagaatagc        647
Pro Gln Leu Ile Ala Val Thr
            135
```

```
aaaatgctga aaagaagcga gtag gac aga gtc aac cag gcg aaa gga gat         698
                          Asp Arg Val Asn Gln Ala Lys Gly Asp
                          140                 145 aag gat cct gcg act tgg atg cct cct ctt ata tcg tat c gtgagttatt        748
Lys Asp Pro Ala Thr Trp Met Pro Pro Leu Ile Ser Tyr
        150                 155                 160 actgccaatc tcccagcctt ttgctaaccg gataatggta g at tgc act tat att        803
                                             His Cys Thr Tyr Ile
                                                             165 cgt gca tgg att gaa gtc aag cac ttt tac ga gtacgtccat tgttgaataa        855
Arg Ala Trp Ile Glu Val Lys His Phe Tyr Glu
            170                 175 ctgcttccta agaatcgaga gctgatggaa gatttcttca g a ctg gcc gtt cac         909
                                               Leu Ala Val His
                                                           180 cca gcg gag aaa gac gcg ttg gtg aat tat ctc agc aag tgc gaa tcg         957
Pro Ala Glu Lys Asp Ala Leu Val Asn Tyr Leu Ser Lys Cys Glu Ser
                185                 190                 195 ccc gct ttt gca agt gat gaa tta gtt atg gga cct gat atg taa            1002
Pro Ala Phe Ala Ser Asp Glu Leu Val Met Gly Pro Asp Met
                200                 205                 210

<210> SEQ ID NO 50
<211> LENGTH: 225
<212> TYPE: PRT
<213> ORGANISM: Rhizoctonia solani

<400> SEQUENCE: 50

Met Tyr Leu Asn Tyr Leu Phe Ala Leu Ala Thr Leu Ala Ala Ala Ser
-15                 -10                 -5                  -1  1

Pro Leu Gly Leu Asp Ser Gly Val Gly Arg Arg Ala Leu Pro Ser Pro
                5                   10                  15

Val Asp Thr Ala Val Ala Lys Gln Tyr Leu Ala Glu Leu Val Val Ala
            20                  25                  30

Gln Pro Val Leu Ser Pro Pro Tyr Asp Arg Lys Lys Phe Pro His Trp
        35                  40                  45

Ile Ser Thr Gly Gly Lys Cys Asp Thr Arg Glu Leu Val Leu Tyr Arg
50                  55                  60                  65

Asp Gly Gln Asn Val Thr Arg Asp Ser Glu Cys Arg Ala Val Ala Gly
                70                  75                  80

Thr Trp Phe Ser Glu Tyr Asp Gly Lys Ser Trp Thr Asn Ala Leu Asp
            85                  90                  95

Leu Asp Ile Asp His Val Val Pro Leu Lys Glu Gly Trp Val Ser Gly
            100                 105                 110

Ala Trp Asn Trp Thr Thr Glu Arg Arg Arg Met Phe Ala Asn Asp Leu
        115                 120                 125

Val Arg Pro Gln Leu Ile Ala Val Thr Asp Arg Val Asn Gln Ala Lys
130                 135                 140                 145

Gly Asp Lys Asp Pro Ala Thr Trp Met Pro Pro Leu Ile Ser Tyr His
                150                 155                 160

Cys Thr Tyr Ile Arg Ala Trp Ile Glu Val Lys His Phe Tyr Glu Leu
            165                 170                 175

Ala Val His Pro Ala Glu Lys Asp Ala Leu Val Asn Tyr Leu Ser Lys
        180                 185                 190

Cys Glu Ser Pro Ala Phe Ala Ser Asp Glu Leu Val Met Gly Pro Asp
    195                 200                 205
```

Met
210

<210> SEQ ID NO 51
<211> LENGTH: 210
<212> TYPE: PRT
<213> ORGANISM: Rhizoctonia solani

<400> SEQUENCE: 51

| | | | | | | | | | | | | | | | |
|---|---|---|---|---|---|---|---|---|---|---|---|---|---|---|---|
| Ser | Pro | Leu | Gly | Leu | Asp | Ser | Gly | Val | Gly | Arg | Arg | Ala | Leu | Pro | Ser |
| 1 | | | | 5 | | | | | 10 | | | | | 15 | |
| Pro | Val | Asp | Thr | Ala | Val | Ala | Lys | Gln | Tyr | Leu | Ala | Glu | Leu | Val | Val |
| | | | 20 | | | | | 25 | | | | | 30 | | |
| Ala | Gln | Pro | Val | Leu | Ser | Pro | Pro | Tyr | Asp | Arg | Lys | Lys | Phe | Pro | His |
| | | 35 | | | | | 40 | | | | | 45 | | | |
| Trp | Ile | Ser | Thr | Gly | Gly | Lys | Cys | Asp | Thr | Arg | Glu | Leu | Val | Leu | Tyr |
| | 50 | | | | | 55 | | | | | 60 | | | | |
| Arg | Asp | Gly | Gln | Asn | Val | Thr | Arg | Asp | Ser | Glu | Cys | Arg | Ala | Val | Ala |
| 65 | | | | | 70 | | | | | 75 | | | | | 80 |
| Gly | Thr | Trp | Phe | Ser | Glu | Tyr | Asp | Gly | Lys | Ser | Trp | Thr | Asn | Ala | Leu |
| | | | | 85 | | | | | 90 | | | | | 95 | |
| Asp | Leu | Asp | Ile | Asp | His | Val | Val | Pro | Leu | Lys | Glu | Gly | Trp | Val | Ser |
| | | | 100 | | | | | 105 | | | | | 110 | | |
| Gly | Ala | Trp | Asn | Trp | Thr | Thr | Glu | Arg | Arg | Arg | Met | Phe | Ala | Asn | Asp |
| | | | 115 | | | | | 120 | | | | | 125 | | |
| Leu | Val | Arg | Pro | Gln | Leu | Ile | Ala | Val | Thr | Asp | Arg | Val | Asn | Gln | Ala |
| | | 130 | | | | | 135 | | | | | 140 | | | |
| Lys | Gly | Asp | Lys | Asp | Pro | Ala | Thr | Trp | Met | Pro | Pro | Leu | Ile | Ser | Tyr |
| 145 | | | | | 150 | | | | | 155 | | | | | 160 |
| His | Cys | Thr | Tyr | Ile | Arg | Ala | Trp | Ile | Glu | Val | Lys | His | Phe | Tyr | Glu |
| | | | | 165 | | | | | 170 | | | | | 175 | |
| Leu | Ala | Val | His | Pro | Ala | Glu | Lys | Asp | Ala | Leu | Val | Asn | Tyr | Leu | Ser |
| | | | 180 | | | | | 185 | | | | | 190 | | |
| Lys | Cys | Glu | Ser | Pro | Ala | Phe | Ala | Ser | Asp | Glu | Leu | Val | Met | Gly | Pro |
| | | | 195 | | | | | 200 | | | | | 205 | | |
| Asp | Met | | | | | | | | | | | | | | |
| | 210 | | | | | | | | | | | | | | |

<210> SEQ ID NO 52
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X=E (Glu), D (Asp), H (His)
<220> FEATURE:
<221> NAME/KEY: MISC_FEATURE
<222> LOCATION: (3)..(3)
<223> OTHER INFORMATION: X=I (Ile, V (Val), L (Leu), F (Phe), M (Met)
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X=P (Pro), A (Ala), S (Ser)

<400> SEQUENCE: 52

```
Xaa His Xaa Xaa Xaa
1               5

<210> SEQ ID NO 53
<211> LENGTH: 5
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X=F (Phe), L (Leu), Y (Tyr), I (Ile)
<220> FEATURE:
<221> NAME/KEY: MISC_FEATURE
<222> LOCATION: (3)..(3)
<223> OTHER INFORMATION: X=N (Asn), R (Arg)
<220> FEATURE:
<221> NAME/KEY: MISC_FEATURE
<222> LOCATION: (5)..(5)
<223> OTHER INFORMATION: X=L (Leu), I (Ile), P (Pro), V (Val)

<400> SEQUENCE: 53

Xaa Ala Xaa Asp Xaa
1               5

<210> SEQ ID NO 54
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: X=D (Asp), N (Asn)
<220> FEATURE:
<221> NAME/KEY: MISC_FEATURE
<222> LOCATION: (4)..(4)
<223> OTHER INFORMATION: X=A (Ala), R (Arg)

<400> SEQUENCE: 54

Cys Xaa Thr Xaa
1

<210> SEQ ID NO 55
<211> LENGTH: 4
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: X=D (Asp), Q (Gln)
<220> FEATURE:
<221> NAME/KEY: MISC_FEATURE
<222> LOCATION: (2)..(2)
<223> OTHER INFORMATION: X=I (Ile), V (Val)

<400> SEQUENCE: 55

Xaa Xaa Asp His
1

<210> SEQ ID NO 56
<211> LENGTH: 6
<212> TYPE: PRT
<213> ORGANISM: Artificial
<220> FEATURE:
<223> OTHER INFORMATION: Motif
<220> FEATURE:
<221> NAME/KEY: MISC_FEATURE
```

```
<222> LOCATION: (3)..(3)
<223> OTHER INFORMATION: X=K (Lys), R (Arg)
<220> FEATURE:
<221> NAME/KEY: MISC_FEATURE
<222> LOCATION: (5)..(5)
<223> OTHER INFORMATION: X=A (Ala), G (Gly)

<400> SEQUENCE: 56

Pro Leu Xaa Glu Xaa Trp
1               5

<210> SEQ ID NO 57
<211> LENGTH: 8
<212> TYPE: PRT
<213> ORGANISM: Artificial
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: X=T (Thr), K (Lys)
<220> FEATURE:
<221> NAME/KEY: MISC_FEATURE
<222> LOCATION: (4)..(4)
<223> OTHER INFORMATION: X=V (Val), I (Ile)
<220> FEATURE:
<221> NAME/KEY: MISC_FEATURE
<222> LOCATION: (5)..(5)
<223> OTHER INFORMATION: X=R (Arg), C (Cys)
<220> FEATURE:
<221> NAME/KEY: MISC_FEATURE
<222> LOCATION: (6)..(6)
<223> OTHER INFORMATION: X=A (Ala), S (ser)

<400> SEQUENCE: 57

Cys Xaa Tyr Xaa Xaa Xaa Trp Ile
1               5
```

POLYPEPTIDES HAVING DNASE ACTIVITY

CROSS-REFERENCE TO RELATED APPLICATIONS

This application is a 35 U.S.C. 371 national application of international application no. PCT/EP2018/057472 filed Mar. 23, 2018 which claims priority or the benefit under 35 U.S.C. 119 of European application nos. EP 17164331.5 filed Mar. 31, 2017 and EP 17180194.7 filed Jul. 7, 2017, the contents of which are fully incorporated herein by reference.

REFERENCE TO A SEQUENCE LISTING

This application contains a Sequence Listing in computer readable form, which is incorporated herein by reference. The contents of the electronic sequence listing created on Mar. 23, 2018, named 20180323-14.10-14499-WO-PCT SQ listing.txt and 141,880 bytes in size, is hereby incorporated by reference in its entirety.

BACKGROUND OF THE INVENTION

Field of the Invention

The present invention relates to polypeptides having DNase activity and polynucleotides encoding the polypeptides. The invention also relates to nucleic acid constructs, vectors, and host cells comprising the polynucleotides as well as methods of producing and using the polypeptides.

Description of the Related Art

Enzymes have been used in detergents for decades. Usually a cocktail of various enzymes is added to detergent compositions. The enzyme cocktail often comprises various enzymes, wherein each enzyme targets it specific substrate e.g. amylases are active towards starch stains, proteases on protein stains and so forth. Textiles and surfaces such as laundry and dishes becomes soiled with many different types of soiling. The soiling may be composed of proteins, grease, starch etc. One type of soiling comes from organic matter such as biofilm. The presence of biofilm provides several disadvantages. Biofilm comprises an extracellular polymeric matrix, composed of polysaccharides, extracellular DNA (eDNA), and proteins. The extracellular polymeric matrix may be sticky or gluing, which when present on textile, gives rise to redeposition or backstaining of soil resulting in a greying of the textile. Another drawback is that malodor may be trapped within the organic structure. Organic matter such as biofilm is therefore not desirable in textiles and surfaces associated with cleaning such as washing machines etc. As organic soiling is a complex mixture of polysaccharides, proteins, DNA etc. there is a need for enzymes which effectively prevent, remove or reduce components of such soiling e.g. DNA on items such of fabrics.

SUMMARY OF THE INVENTION

One embodiment of the invention relates to a polypeptide of the KEAW or the RAWI clade, wherein the polypeptide has DNase activity, and wherein the polypeptide is selected from the group consisting of:
(a) a polypeptide having at least 80% sequence identity to the polypeptide of SEQ ID NO: 3;
(b) a polypeptide having at least 80% sequence identity to the polypeptide of SEQ ID NO: 6;
(c) a polypeptide having at least 80% sequence identity to the polypeptide of SEQ ID NO: 9;
(d) a polypeptide having at least 80% sequence identity to the polypeptide of SEQ ID NO: 12;
(e) a polypeptide having at least 80% sequence identity to the polypeptide of SEQ ID NO: 15;
(f) a polypeptide having at least 80% sequence identity to the polypeptide of SEQ ID NO: 18;
(g) a polypeptide having at least 80% sequence identity to the polypeptide of SEQ ID NO: 21;
(h) a polypeptide having at least 80% sequence identity to the polypeptide of SEQ ID NO: 24;
(i) a polypeptide having at least 80% sequence identity to the polypeptide of SEQ ID NO: 27;
(j) a polypeptide having at least 80% sequence identity to the polypeptide of SEQ ID NO: 30;
(k) a polypeptide having at least 80% sequence identity to the polypeptide of SEQ ID NO: 33;
(l) a polypeptide having at least 80% sequence identity to the polypeptide of SEQ ID NO: 36;
(m) a polypeptide having at least 80% sequence identity to the polypeptide of SEQ ID NO: 39;
(n) a polypeptide having at least 80% sequence identity to the polypeptide of SEQ ID NO: 42;
(o) a polypeptide having at least 80% sequence identity to the polypeptide of SEQ ID NO: 45;
(p) a polypeptide having at least 80% sequence identity to the polypeptide of SEQ ID NO: 48;
(q) a polypeptide having at least 80% sequence identity to the polypeptide of SEQ ID NO: 51;
(r) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48 and SEQ ID NO: 51, wherein the variant has DNase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(s) a polypeptide comprising the polypeptide of (a) to (q) and a N-terminal and/or C-terminal His-tag and/or HQ-tag;
(t) a polypeptide comprising the polypeptide of (a) to (q) and a N-terminal and/or C-terminal extension of between 1 and 10 amino acids; and
(u) a fragment of the polypeptide of (a) to (q) having DNase activity and having at least 90% of the length of the mature polypeptide
(v) a polypeptide comprising one or both the motif(s) PL[KR]E[AG]W (SEQ ID NO:56) or C[TK]Y[VI][RC][AS]WI (SEQ ID NO: 57).

The invention further relates to a composition e.g. a cleaning or detergent composition, an automatic dish wash (ADW) composition or a laundry composition, comprising a polypeptide according to the invention.

The invention further relates to use of a polypeptide according to the invention for deep cleaning of an item, such as textile e.g. fabric. The invention further relates to the use of a DNase according to the invention,
(i) for preventing, reducing or removing stickiness of the item;
(ii) for pretreating stains on the item;

(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removing malodor from the item,
wherein the item is a textile.

The invention also relates to a method for laundering an item comprising the steps of:
a. Exposing an item to a wash liquor comprising a polypeptide according to the invention or a cleaning composition comprising a polypeptide according to the invention;
b. Completing at least one wash cycle; and
c. Optionally rinsing the item,
wherein the item is a textile.

A further aspect of the invention relates to use of a polypeptide of the invention for cleaning of a textile item in the presence of sulfite.

The invention further relates to a polynucleotide encoding the polypeptide of the invention, and a nucleic acid construct or expression vector comprising a polynucleotide encoding a polypeptide of the invention, which is operably linked to one or more control sequences that direct the production of the polypeptide in an expression host. The invention further relates to a recombinant host cell comprising a polynucleotide encoding a polypeptide of the invention, which is operably linked to one or more control sequences that direct the production of the polypeptide, wherein the method may further comprise cultivating a cell, which in its wild-type form produces the polypeptide, under conditions conducive for production of the polypeptide and optionally recovering the polypeptide. The invention also relates to a method of producing a polypeptide having DNase activity, comprising cultivating a recombinant host cell comprising a polynucleotide encoding the polypeptide under conditions conducive for production of the polypeptide.

OVERVIEW OF SEQUENCES

SEQ ID NO: 1 DNA encoding full length polypeptide from *Pholiota squarrosa*
SEQ ID NO: 2 polypeptide derived from SEQ ID NO: 1
SEQ ID NO: 3 mature polypeptide obtained from *Pholiota squarrosa*
SEQ ID NO: 4 DNA encoding full length polypeptide from *Marasmius oreades*
SEQ ID NO: 5 polypeptide derived from SEQ ID NO: 4
SEQ ID NO: 6 mature polypeptide obtained from *Marasmius oreades*
SEQ ID NO: 7 DNA encoding full length polypeptide from *Cercospora*
SEQ ID NO: 8 polypeptide derived from SEQ ID NO: 7
SEQ ID NO: 9 mature polypeptide obtained from *Cercospora fusimaculans*
SEQ ID NO: 10 DNA encoding full length polypeptide from *Deconica coprophila*
SEQ ID NO: 11 polypeptide derived from SEQ ID NO: 10
SEQ ID NO: 12 mature polypeptide obtained from *Deconica coprophila*
SEQ ID NO: 13 DNA encoding full length polypeptide from *Mortierella humilis*
SEQ ID NO: 14 polypeptide derived from SEQ ID NO: 13
SEQ ID NO: 15 mature polypeptide obtained from *Mortierella humilis*
SEQ ID NO: 16 DNA encoding full length polypeptide from *Physisporinus sanguinolentus*
SEQ ID NO: 17 polypeptide derived from SEQ ID NO: 16
SEQ ID NO: 18 mature polypeptide obtained from *Physisporinus sanguinolentus*
SEQ ID NO: 19 DNA encoding full length polypeptide from *Stropharia semiglobata*
SEQ ID NO: 20 polypeptide derived from SEQ ID NO: 19
SEQ ID NO: 21 mature polypeptide obtained from *Stropharia semiglobata*
SEQ ID NO: 22 DNA encoding full length polypeptide from *Cladosporium cladosporioides*
SEQ ID NO: 23 polypeptide derived from SEQ ID NO: 22
SEQ ID NO: 24 mature polypeptide obtained from *Cladosporium cladosporioides*
SEQ ID NO: 25 DNA encoding full length polypeptide from *Irpex lacteus*
SEQ ID NO: 26 polypeptide derived from SEQ ID NO: 25
SEQ ID NO: 27 mature polypeptide obtained from *Irpex lacteus*
SEQ ID NO: 28 DNA encoding full length polypeptide from *Phlebia subochracea*
SEQ ID NO: 29 polypeptide derived from SEQ ID NO: 28
SEQ ID NO: 30 mature polypeptide obtained from *Phlebia subochracea*
SEQ ID NO: 31 DNA encoding full length polypeptide from *Rhizoctonia solani*
SEQ ID NO: 32 polypeptide derived from SEQ ID NO: 31
SEQ ID NO: 33 mature polypeptide obtained from *Rhizoctonia solani*
SEQ ID NO: 34 DNA encoding full length polypeptide from *Rhizoctonia solani* 1135
SEQ ID NO: 35 polypeptide derived from SEQ ID NO: 34
SEQ ID NO: 36 mature polypeptide obtained from *Rhizoctonia solani* 1135
SEQ ID NO: 37 DNA encoding full length polypeptide from *Rhizoctonia solani* 1135
SEQ ID NO: 38 polypeptide derived from SEQ ID NO: 37
SEQ ID NO: 39 mature polypeptide obtained from *Rhizoctonia solani* 1135
SEQ ID NO: 40 DNA encoding full length polypeptide from *Rhizoctonia solani* AG-1 IA
SEQ ID NO: 41 polypeptide derived from SEQ ID NO: 40
SEQ ID NO: 42 mature polypeptide obtained from *Rhizoctonia solani* AG-1 IA
SEQ ID NO: 43 DNA encoding full length polypeptide from *Rhizoctonia solani* AG2-2IIIB
SEQ ID NO: 44 polypeptide derived from SEQ ID NO: 43
SEQ ID NO: 45 mature polypeptide obtained from *Rhizoctonia solani* AG2-2IIIB
SEQ ID NO: 46 DNA encoding full length polypeptide from *Rhizoctonia solani* 123E
SEQ ID NO: 47 polypeptide derived from SEQ ID NO: 46
SEQ ID NO: 48 mature polypeptide obtained from *Rhizoctonia solani* 123E
SEQ ID NO: 49 DNA encoding full length polypeptide from *Rhizoctonia solani* AG-1 IB
SEQ ID NO: 50 polypeptide derived from SEQ ID NO: 49
SEQ ID NO: 51 mature polypeptide obtained from *Rhizoctonia solani* AG-1 IB
SEQ ID NOs: 52-57 are motifs disclosed herein.

Definitions

The term "DNase" means a polypeptide with DNase activity that catalyzes the hydrolytic cleavage of phosphodiester linkages in the DNA backbone, thus degrading DNA.

The term "DNases" and the expression "a polypeptide with DNase activity" are used interchangeably throughout the application. For purposes of the present invention, DNase activity is determined according to the procedure described in the Assay I or Assay II. In one aspect, the polypeptides of the present invention have at least 20%, e.g., at least 40%, at least 50%, at least 60%, at least 70%, at least 80%, at least 90%, at least 95%, or at least 100% of the DNase activity of the mature polypeptide shown in SEQ ID NO: 3, 6, 9, 12, 15, 18, 21, 24, 27, 30, 33, 36, 39, 42, 45, 48 or 51.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "biofilm" means organic matter produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Organic matter such as biofilms may form on living or non-living surfaces. The microbial cells growing and producing biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry biofilm producing bacteria can be found among the following species including *Acinetobacter* sp., *Aeromicrobium* sp., *Brevundimonas* sp., *Microbacterium* sp., *Micrococcus luteus, Pseudomonas* sp., *Staphylococcus epidermidis,* and *Stenotrophomonas* sp. On hard surfaces biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis, Staphylococcus aureus* and *Stenotrophomonas* sp.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "eDNA" means in the present context extracellular DNA.

The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a mature polypeptide of the present invention. Each control sequence may be native (i.e., from the same gene) or (foreign i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The term "deep cleaning" means disruption, reduction or removal of organic components such as polysaccharides, proteins, DNA, soil or other components present in organic matter such as biofilm.

The term "detergent adjunct ingredient" is different to the DNases of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

The term "detergent composition" refers to compositions that find use in the removal of undesired compounds from items to be cleaned, such as textiles. The terms "detergent compositions" and "cleaning compositions" are used interchangeably in the present application. The detergent composition may be used to e.g. clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression. A control sequence may be foreign or heterologous to the expression vector.

A "His-tag" refers to a polyhistidine tag typically comprising at least 6 histidine residues, that may be added to the N- or C-terminal. His-tags are known in the art for use in e.g. protein purification, but may also be used for improving solubility at low pH values. Similarly, an "HQ-tag", i.e. a histidine-glutamine tag, may also be used for the purpose of purification as is known in the art.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

By the term "malodor" is meant an odor which is not desired on clean items. The cleaned item should smell fresh and clean without malodors adhered to the item. One example of malodor is compounds with an unpleasant smell, which may be produced by microorganisms and trapped within a biofilm or stick to the "glue" of a biofilm. Other examples of unpleasant smells are sweat or body odor adhered to an item, which has been in contact with human or animal. Other examples of malodor are odor from spices, which sticks to items for example curry or other exotic spices which smells strongly.

The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 188 of SEQ ID NO: 2. Amino acids −19 to −1 of SEQ ID NO: 2 is the signal peptide.

In one aspect, the mature polypeptide is amino acids 1 to 182 of SEQ ID NO: 5. Amino acids −17 to −1 of SEQ ID NO: 5 is the signal peptide.

In one aspect, the mature polypeptide is amino acids 1 to 193 of SEQ ID NO: 8. Amino acids −15 to −1 of SEQ ID NO: 8 is the signal peptide.

In one aspect, the mature polypeptide is amino acids 1 to 187 of SEQ ID NO: 11. Amino acids −17 to −1 of SEQ ID NO: 11 is the signal peptide.

In one aspect, the mature polypeptide is amino acids 1 to 182 of SEQ ID NO: 14. Amino acids −23 to −1 of SEQ ID NO: 14 is the signal peptide.

In one aspect, the mature polypeptide is amino acids 1 to 192 of SEQ ID NO: 17. Amino acids −18 to −1 of SEQ ID NO: 17 is the signal peptide.

In one aspect, the mature polypeptide is amino acids 1 to 187 of SEQ ID NO: 20. Amino acids −17 to −1 of SEQ ID NO: 20 is the signal peptide.

In one aspect, the mature polypeptide is amino acids 1 to 194 of SEQ ID NO: 23. Amino acids −18 to −1 of SEQ ID NO: 23 is the signal peptide.

In one aspect, the mature polypeptide is amino acids 1 to 197 of SEQ ID NO: 26. Amino acids −21 to −1 of SEQ ID NO: 26 is the signal peptide.

In one aspect, the mature polypeptide is amino acids 1 to 188 of SEQ ID NO: 29. Amino acids −18 to −1 of SEQ ID NO: 29 is the signal peptide.

In one aspect, the mature polypeptide is amino acids 1 to 208 of SEQ ID NO: 32. Amino acids −15 to −1 of SEQ ID NO: 32 is the signal peptide.

In one aspect, the mature polypeptide is amino acids 1 to 210 of SEQ ID NO: 35. Amino acids −15 to −1 of SEQ ID NO: 35 is the signal peptide.

In one aspect, the mature polypeptide is amino acids 1 to 191 of SEQ ID NO: 38. Amino acids −17 to −1 of SEQ ID NO: 38 is the signal peptide.

In one aspect, the mature polypeptide is amino acids 1 to 206 of SEQ ID NO: 41. Amino acids −21 to −1 of SEQ ID NO: 41 is the signal peptide.

In one aspect, the mature polypeptide is amino acids 1 to 210 of SEQ ID NO: 44. Amino acids −15 to −1 of SEQ ID NO: 44 is the signal peptide.

In one aspect, the mature polypeptide is amino acids 1 to 193 of SEQ ID NO: 47. Amino acids −18 to −1 of SEQ ID NO: 47 is the signal peptide.

In one aspect, the mature polypeptide is amino acids 1 to 210 of SEQ ID NO: 50. Amino acids −15 to −1 of SEQ ID NO: 50 is the signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

The term "mature polypeptide coding sequence" means a polynucleotide that encodes a mature polypeptide having DNase activity.

In one aspect, the mature polypeptide coding sequence is nucleotides 58 to 1088 of SEQ ID NO: 1 and nucleotides 1 to 57 of SEQ ID NO: 1 encode a signal peptide.

In one aspect, the mature polypeptide coding sequence is nucleotides 52 to 1147 of SEQ ID NO: 4 and nucleotides 1 to 51 of SEQ ID NO: 4 encode a signal peptide.

In one aspect, the mature polypeptide coding sequence is nucleotides 46 to 679 of SEQ ID NO: 7 and nucleotides 1 to 45 of SEQ ID NO: 7 encode a signal peptide.

In one aspect, the mature polypeptide coding sequence is nucleotides 52 to 953 of SEQ ID NO: 10 and nucleotides 1 to 51 of SEQ ID NO: 10 encode a signal peptide.

In one aspect, the mature polypeptide coding sequence is nucleotides 70 to 615 of SEQ ID NO: 13 and nucleotides 1 to 69 of SEQ ID NO: 13 encode a signal peptide.

In one aspect, the mature polypeptide coding sequence is nucleotides 55 to 996 of SEQ ID NO: 16 and nucleotides 1 to 54 of SEQ ID NO: 16 encode a signal peptide.

In one aspect, the mature polypeptide coding sequence is nucleotides 52 to 1190 of SEQ ID NO: 19 and nucleotides 1 to 51 of SEQ ID NO: 19 encode a signal peptide.

In one aspect, the mature polypeptide coding sequence is nucleotides 55 to 744 of SEQ ID NO: 22 and nucleotides 1 to 54 of SEQ ID NO: 22 encode a signal peptide.

In one aspect, the mature polypeptide coding sequence is nucleotides 64 to 975 of SEQ ID NO: 25 and nucleotides 1 to 63 of SEQ ID NO: 25 encode a signal peptide.

In one aspect, the mature polypeptide coding sequence is nucleotides 55 to 924 of SEQ ID NO: 28 and nucleotides 1 to 54 of SEQ ID NO: 28 encode a signal peptide.

In one aspect, the mature polypeptide coding sequence is nucleotides 46 to 983 of SEQ ID NO: 31 and nucleotides 1 to 45 of SEQ ID NO: 31 encode a signal peptide.

In one aspect, the mature polypeptide coding sequence is nucleotides 46 to 993 of SEQ ID NO: 34 and nucleotides 1 to 45 of SEQ ID NO: 34 encode a signal peptide.

In one aspect, the mature polypeptide coding sequence is nucleotides 52 to 953 of SEQ ID NO: 37 and nucleotides 1 to 51 of SEQ ID NO: 37 encode a signal peptide.

In one aspect, the mature polypeptide coding sequence is nucleotides 64 to 995 of SEQ ID NO: 40 and nucleotides 1 to 63 of SEQ ID NO: 40 encode a signal peptide.

In one aspect, the mature polypeptide coding sequence is nucleotides 46 to 985 of SEQ ID NO: 43 and nucleotides 1 to 45 of SEQ ID NO: 43 encode a signal peptide.

In one aspect, the mature polypeptide coding sequence is nucleotides 55 to 952 of SEQ ID NO: 46 and nucleotides 1 to 54 of SEQ ID NO: 46 encode a signal peptide.

In one aspect, the mature polypeptide coding sequence is nucleotides 46 to 999 of SEQ ID NO: 49 and nucleotides 1 to 45 of SEQ ID NO: 49 encode a signal peptide.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, and which comprises one or more control sequences that may be heterologous.

The term "operably linked" means a configuration in which a control sequence is placed at an appropriate position relative to the coding sequence of a polynucleotide such that the control sequence directs expression of the coding sequence.

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

The term "variant" means a polypeptide having DNase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position Nomenclature For purposes of the present invention, the nomenclature [E/Q] means that the amino acid at this position may be a glutamic acid (Glu, E) or a glutamine (Gln, Q). Likewise, the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

The present invention relates to novel polypeptides having deoxyribonuclease (DNase) activity which can be used for preventing, reducing or removing biofilm soiling on items such as textiles and/or fabric. A polypeptide having DNase activity or a deoxyribonuclease (DNase) is any enzyme that catalyzes the hydrolytic cleavage of phosphodiester linkages in the DNA backbone, thus degrading DNA. The two terms polypeptide having DNase activity and DNase are used interchangeably.

Polypeptides Having DNase Activity

The present invention relates to polypeptides having DNase activity i.e. DNases. Examples of polypeptides having DNase activity are polypeptides comprising the PFAM domain DUF1524 (pfam.xfam.org/), "The Pfam protein families database: towards a more sustainable future", R. D. Finn, et. al. Nucleic Acids Research (2016) Database Issue 44: D279-D285". The DUF1524 domain contains a conserved HXXP sequence motif commonly found in nucleases (M. A. Machnicka, et. al. Phylogenomics and sequence-structure-function relationships in the GmrSD family of Type IV restriction enzymes, BMC Bioinformatics, 2015, 16, 336). DUF means domain of unknown function, and the polypeptide families comprising, e.g., DUF have been collected together in the Pfam database. The Pfam data base provides sequence alignments and hidden Markov models that define the collected protein domains. A protein domain is a conserved part of a given protein sequence. Each domain forms a compact three-dimensional structure and often can be independently stable and folded. Many proteins consist of several structural domains. One domain may appear in a variety of different proteins.

One particular DUF may be identified using the prefix DUF followed by a number, e.g., 1524. The DUF1524 is a family of proteins all comprising the HXXP motif, where H is the amino acid histidine, P is the amino acid proline and X is any amino acid. In one embodiment of the invention the polypeptides having DNase activity comprise the DUF1524 domain. Thus, according to one embodiment the invention relates to polypeptides having DNase activity, wherein the polypeptides comprise the DUF1524 domain. The invention also relates to the use of such DNases e.g. for cleaning of textiles and/or fabric. The invention further relates to compositions comprising polypeptides having DNase activity, and which comprise a DUF1524 domain e.g. HXXP. Such compositions may be but are not limited to liquid or powder laundry compositions, tablets, unit dose, spray or soap bars. Polypeptides comprising the DUF1524 domain comprise several motifs, of which one example is [E/D/H]H[I/V/L/F/M]X[P/A/S] (SEQ ID NO: 52), situated in positions corresponding to positions 101 to 105 in R. solani (SEQ ID NO 45). H102 is a catalytic residue involved in the catalytic activity of DUF1524, and part of the HXXP motif.

As already described the polypeptides of the invention having DNase activity may comprise the structural domains of DUF1524. A further domain, preferably shared by the DNases of the invention, was identified. This domain is termed NUC1 and polypeptides of this domain are in addition to having DNase activity, characterized by comprising certain motifs e.g. one or more of the motifs [F/L/Y/I]A[N/R]D[L/I/P/V](SEQ ID NO: 53), corresponding to position 125 to 129 in SEQ ID NO 45 or C[D/N]T[A/R] (SEQ ID NO: 54), corresponding to (position 56 to 59 in SEQ ID NO 45). From the NUC1 domain a sub-domain has been identified by the inventors and this domain is termed the NUC1_A domain. In addition to comprising any of the domains above the polypeptides having DNase activity belonging to the NUC1_A domain may share the common motif [D/Q][IN]DH (SEQ ID NO 55). In one embodiment the invention relates to polypeptides comprising the motif [D/Q][IN]DH (SEQ ID NO: 55), wherein the polypeptides have DNase activity. In one embodiment the invention relates to polypeptides comprising the motif [D/Q][I/V]DH (SEQ ID NO:55). In some embodiments of the invention the DNases of the invention belong to a specific subgroup or clade comprising the motif PL[KR]E[AG]W (SEQ ID NO 56), and/or C[TK]Y[VI][RC][AS]WI (SEQ ID NO 57). In one aspect, the polypeptide of the invention having DNase activity belongs to the KEAW clade and comprises the motif PL[KR]E[AG]W (SEQ ID NO 56), corresponding to position 100 to 105 of SEQ ID NO 45, where P (corresponding to position 100 of SEQ ID NO 45), an alignment of the polypeptides of the invention comprised in the clade is shown in FIG. 1. A phylogenetic tree of the KEAW clade is shown in FIG. 2. The KEAW clade is defined in the present context as a subgroup of NUC1_A DNases which is structurally and optionally also functionally more related than other NUC1_A DNases i.e. it is a subgroup of closely related DNases. In one aspect, the invention relates to a polypeptide having DNase activity, wherein the polypeptide belongs to the KEAW clade and comprises the motif PL [KR]E[AG]W (SEQ ID NO 56). In one aspect, the invention relates to a polypeptide having DNase activity, wherein the polypeptide belongs to the KEAW clade and comprises the motif PL [KR]E[AG]W (SEQ ID NO 56), wherein the polypeptide is selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51 and polypeptides having at least 80% sequence identity hereto.

Figure 3:
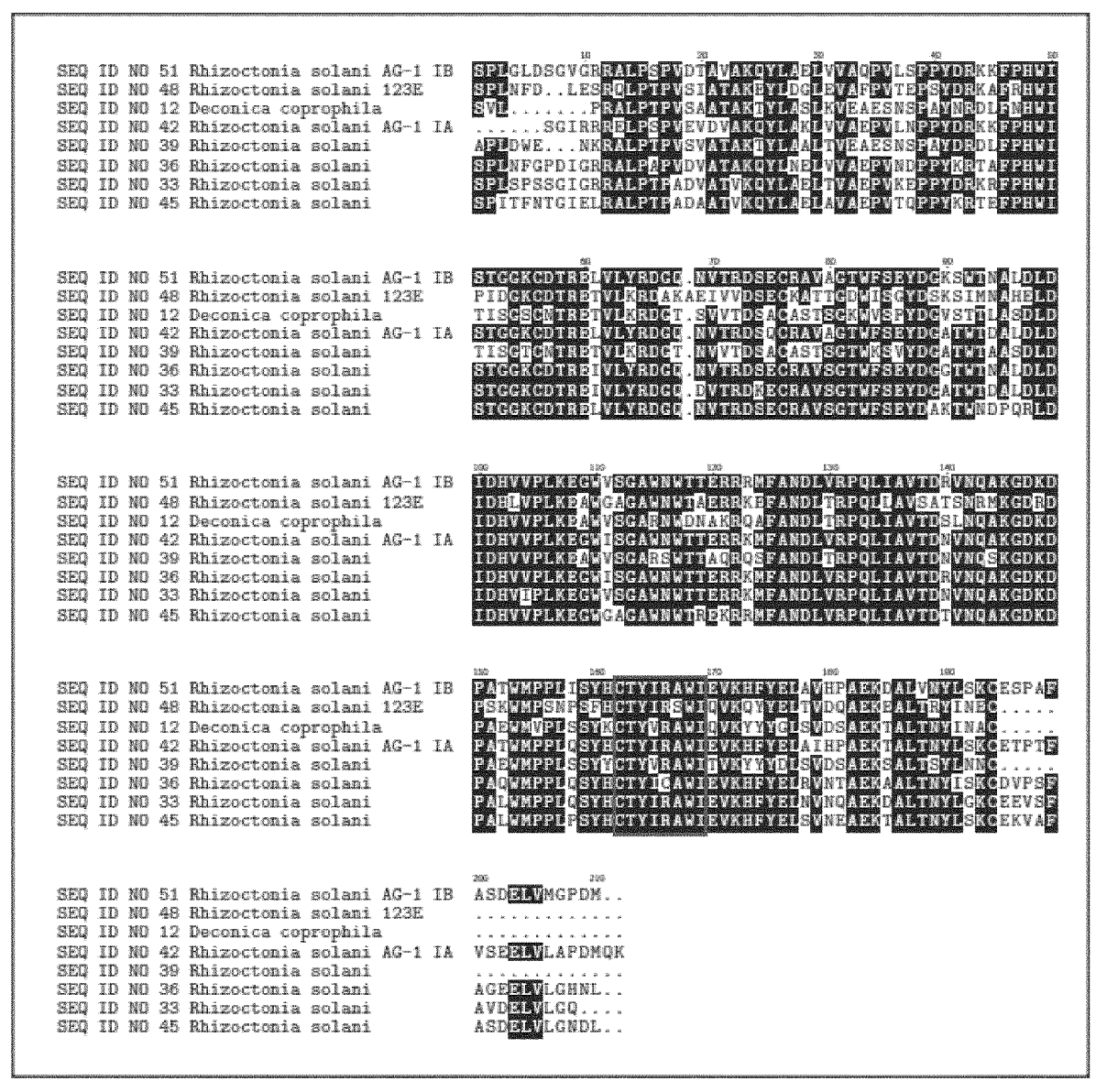
Figure 4:
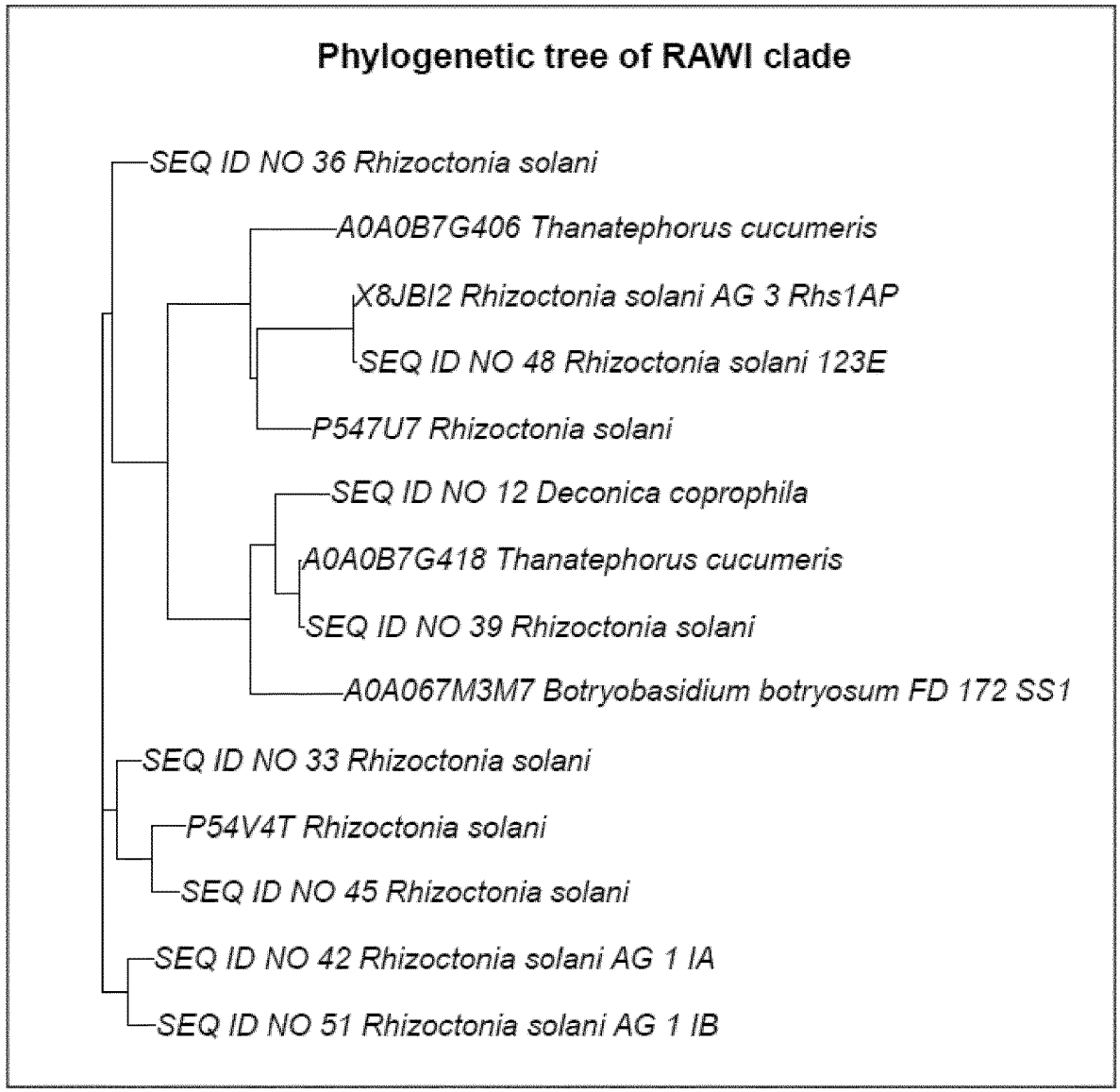

In one aspect, the polypeptide of the invention having DNase activity belongs to the RAWI clade and comprises the motif C[TK]Y[VI][RC][AS]WI (SEQ ID NO: 57), corresponding to position 162 to 168 in SEQ ID NO 45. An alignment of the polypeptides of the invention comprised in the clade is shown in FIG. 3. A phylogenetic tree of the RAWI clade is shown in FIG. 4. The RAWI clade is defined in the present context as a subgroup of NUC1_A DNases which is structurally and optionally also functionally more related than other NUC1_A DNases i.e. it is a subgroup of closely related DNases. In one aspect, the invention relates to a polypeptide having DNase activity, wherein the polypeptide belongs to the RAWI clade and comprises the motif C[TK]Y[VI][RC][AS]WI (SEQ ID NO: 57). In one aspect, the invention relates to a polypeptide having DNase activity, wherein the polypeptide belongs to the RAWI clade and comprises the motif C[TK]Y[VI][RC][AS]WI (SEQ ID NO: 57), wherein the polypeptide is selected from the group consisting of SEQ ID NO: 12, SEQ ID NO: 33, SEQ ID NO: 36, SEQ ID NO: 39, SEQ ID NO: 42, SEQ ID NO: 45, SEQ ID NO: 48, SEQ ID NO: 51 and polypeptides having at least 80% sequence identity hereto.

In one aspect of the invention the DNase is a polypeptide comprising one of more of the motifs selected from the group consisting of [E/D/H]H[I/V/L/F/M]X[P/A/S] (SEQ ID NO 52), [F/L/Y/I]A[N/R]D[L/I/P/V] (SEQ ID NO: 53), C[D/N]T[A/R] (SEQ ID NO: 54), [D/Q][I/V]DH (SEQ ID NO 55), PL[KR]E[AG]W (SEQ ID NO 56), and C[TK]Y[VI][RC][AS]WI (SEQ ID NO 57). Preferably, the DNases of the invention comprises one or both motif(s) PL[KR]E[AG]W (SEQ ID NO 56) or C[TK]Y[VI][RC][AS]WI (SEQ ID NO 57). One embodiment of the invention relates to a polypeptide having DNase activity, wherein the polypeptide comprises any of the motifs [E/D/H]H[I/V/L/F/M]X[P/A/S] (SEQ ID NO 52), [F/L/Y/I]A[N/R]D[L/I/P/V] (SEQ ID NO: 53), C[D/N]T[A/R] (SEQ ID NO: 54), [D/Q][I/V]DH (SEQ ID NO 55), PL[KR]E[AG]W (SEQ ID NO 56), and C[TK]Y[VI][RC][AS]WI (SEQ ID NO 57) and wherein the polypeptide is selected from the group consisting of:
 i) a polypeptide comprising or consisting of SEQ ID NO 3 or a polypeptide having at least 80% sequence identity hereto;
 ii) a polypeptide comprising or consisting of SEQ ID NO 6 or a polypeptide having at least 80% sequence identity hereto;
 iii) a polypeptide comprising or consisting of SEQ ID NO 9 or a polypeptide having at least 80% sequence identity hereto;
 iv) a polypeptide comprising or consisting of SEQ ID NO 12 or a polypeptide having at least 80% sequence identity hereto;
 v) a polypeptide comprising or consisting of SEQ ID NO 15 or a polypeptide having at least 80% sequence identity hereto;
 vi) a polypeptide comprising or consisting of SEQ ID NO 18 or a polypeptide having at least 80% sequence identity hereto;
 vii) a polypeptide comprising or consisting of SEQ ID NO 21 or a polypeptide having at least 80% sequence identity hereto;
 viii) a polypeptide comprising or consisting of SEQ ID NO 24 or a polypeptide having at least 80% sequence identity hereto;
 ix) a polypeptide comprising or consisting of SEQ ID NO 27 or a polypeptide having at least 80% sequence identity hereto;
 x) a polypeptide comprising or consisting of SEQ ID NO 30 or a polypeptide having at least 80% sequence identity hereto;

xi) a polypeptide comprising or consisting of SEQ ID NO 33 or a polypeptide having at least 80% sequence identity hereto;

xii) a polypeptide comprising or consisting of SEQ ID NO 36 or a polypeptide having at least 80% sequence identity hereto;

xiii) a polypeptide comprising or consisting of SEQ ID NO 39 or a polypeptide having at least 80% sequence identity hereto;

xiv) a polypeptide comprising or consisting of SEQ ID NO 42 or a polypeptide having at least 80% sequence identity hereto;

xv) a polypeptide comprising or consisting of SEQ ID NO 45 or a polypeptide having at least 80% sequence identity hereto;

xvi) a polypeptide comprising or consisting of SEQ ID NO 48 or a polypeptide having at least 80% sequence identity hereto; and xvii) a polypeptide comprising or consisting of SEQ ID NO 51 or a polypeptide having at least 80% sequence identity hereto.

In one embodiment, the DNase polypeptide comprises the motif C[TK]Y[VI][RC][AS]WI (SEQ ID NO: 56) and/or the motif PL[KR]E[AG]W (SEQ ID NO: 55), and preferably is selected from the group selected from polypeptides comprising the amino acid sequences shown in SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO:27, SEQ ID NO: 30, SEQ ID NO: 33, SEQ ID NO: 36, SEQ ID NO: 39, SEQ ID NO: 42, SEQ ID NO: 45, SEQ ID NO: 48 and SEQ ID NO: 51 or polypeptides having at least 80% sequence identity hereto. In one embodiment, the DNase polypeptide is obtained or is obtainable from the taxonomic order Cantharellales. In one embodiment, the DNase polypeptide is obtained or is obtainable from the taxonomic order Cantharellales, preferably the taxonomic genus *Rhizoctonia*. In one embodiment, the DNase polypeptide is obtained or is obtainable from the taxonomic genus *Rhizoctonia* and is selected from the group selected from SEQ ID NO: 33, SEQ ID NO: 36, SEQ ID NO: 39, SEQ ID NO: 42, SEQ ID NO: 45, SEQ ID NO: 48 and SEQ ID NO: 51 or a polypeptide having at least 80% sequence identity hereto.

The motifs and domains are defined cross-kingdom, meaning that the domains and motifs comprise both fungal and bacterial DNases. It is well known that DNases deriving from organisms belonging to different taxonomic groups may nevertheless share common structural elements, which can be identified by comparing the primary structures e.g. amino acid sequences and grouping the DNases according to sequence homology. However, common structural elements may also be identified by comparing the three-dimensional (3D) structure of various DNases. Both approaches have been applied in the present invention.

The structural approach identified DNases which derive from organisms from divergent taxonomic groups but share structural elements common for the identified group. Structural domains and sub-domains are groups of DNases from divergent taxa that share structural elements. A clade is a grouping that includes a common ancestor and all the descendants (living and extinct) of that ancestor (evolution. berkeley.edu/evolibrary/article/0_0_0/evo_06) a Glade has a shared phylogeny. In the examples is described building of phylogenetic trees, such trees have branches which represent clades, see FIGS. 1 and 2.

One embodiment of the invention relates a polypeptide of the KEAW or the RAWI clade, wherein the polypeptide has DNase activity, and wherein the polypeptide is selected from the group consisting of:

(a) a polypeptide having at least 80% sequence identity to the polypeptide of SEQ ID NO: 3;

(b) a polypeptide having at least 80% sequence identity to the polypeptide of SEQ ID NO: 6;

(c) a polypeptide having at least 80% sequence identity to the polypeptide of SEQ ID NO: 9;

(d) a polypeptide having at least 80% sequence identity to the polypeptide of SEQ ID NO: 12;

(e) a polypeptide having at least 80% sequence identity to the polypeptide of SEQ ID NO: 15;

(f) a polypeptide having at least 80% sequence identity to the polypeptide of SEQ ID NO: 18;

(g) a polypeptide having at least 80% sequence identity to the polypeptide of SEQ ID NO: 21;

(h) a polypeptide having at least 80% sequence identity to the polypeptide of SEQ ID NO: 24;

(i) a polypeptide having at least 80% sequence identity to the polypeptide of SEQ ID NO: 27;

(j) a polypeptide having at least 80% sequence identity to the polypeptide of SEQ ID NO: 30;

(k) a polypeptide having at least 80% sequence identity to the polypeptide of SEQ ID NO: 33;

(l) a polypeptide having at least 80% sequence identity to the polypeptide of SEQ ID NO: 36;

(m) a polypeptide having at least 80% sequence identity to the polypeptide of SEQ ID NO: 39;

(n) a polypeptide having at least 80% sequence identity to the polypeptide of SEQ ID NO: 42;

(o) a polypeptide having at least 80% sequence identity to the polypeptide of SEQ ID NO: 45;

(p) a polypeptide having at least 80% sequence identity to the polypeptide of SEQ ID NO: 48;

(q) a polypeptide having at least 80% sequence identity to the polypeptide of SEQ ID NO: 51;

(r) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48 and SEQ ID NO: 51, wherein the variant has DNase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;

(s) a polypeptide comprising the polypeptide of (a) to (q) and a N-terminal and/or C-terminal His-tag and/or HQ-tag;

(t) a polypeptide comprising the polypeptide of (a) to (q) and a N-terminal and/or C-terminal extension of between 1 and 10 amino acids; and (u) a fragment of the polypeptide of (a) to (q) having DNase activity and having at least 90% of the length of the mature polypeptide (v) a polypeptide comprising one or both the motif(s) PL[KR]E[AG]W (SEQ ID NO:56) or C[TK]Y[VI] [RC][AS]WI (SEQ ID NO: 57).

The DNases of the present invention are useful in cleaning compositions and are effective in deep cleaning of surfaces such as fabrics. The DNases of the present invention are effective in reducing or removing DNA soiling from e.g. organic matter. One example of organic matter is biofilm which is an extracellular matrix produced by various microorganisms. The extracellular polymeric matrix is composed of polysaccharides, extracellular DNA and proteins. Organic matter like biofilm may be sticky or gluing, which when present on textile may give rise to redeposition or backstaining of soil resulting in a greying of the textile. Another drawback of organic matter is malodor as various malodor related molecules are often associated with organic matter e.g. biofilm.

One aspect of the invention relates to a method for laundering an item comprising the steps of:
a. Exposing an item to a wash liquor comprising a polypeptide or a cleaning composition comprising a polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48 and SEQ ID NO: 51 or polypeptides having at least 80% sequence identity hereto, wherein the polypeptide has DNase activity;
b. Completing at least one wash cycle; and
c. Optionally rinsing the item,
wherein the item is a textile.

The DNases of the invention are therefore useful for prevention, reduction or removal of malodor and for prevention, reduction of redeposition and improving whiteness.

One embodiment of the invention relates to the use of polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48 and SEQ ID NO: 51 or polypeptides having at least 80% sequence identity hereto for deep cleaning of an item, wherein the item is a textile. One embodiment of the invention relates to the use of polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48 and SEQ ID NO: 51 or polypeptides having at least 80% sequence identity hereto;
(i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item, wherein the item is a textile.

The textile may e.g. be cotton or polyester or a mixture hereof.

One embodiment of the invention relates to a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the polypeptide shown in SEQ ID NO: 3, SEQ ID NO: 6, SEQ ID NO: 9, SEQ ID NO: 12, SEQ ID NO: 15, SEQ ID NO: 18, SEQ ID NO: 21, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 44, SEQ ID NO: 48 or SEQ ID NO: 51.

In one embodiment, the present invention relates to polypeptides having a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 2 or the mature polypeptide shown in SEQ ID NO 3, e.g. at least 80% or at least 90% of the DNase activity of the mature polypeptide.

In a particular embodiment, the invention relates to polypeptides having a sequence identity to the mature polypeptide of SEQ ID NO: 5 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 5 or the mature polypeptide shown in SEQ ID NO 6, e.g. at least 80% or at least 90% of the DNase activity of the mature polypeptide.

In a particular embodiment, the invention relates to polypeptides having a sequence identity to the mature polypeptide of SEQ ID NO: 8 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 8 or the mature polypeptide shown in SEQ ID NO 9, e.g. at least 80% or at least 90% of the DNase activity of the mature polypeptide.

In a particular embodiment, the invention relates to polypeptides having a sequence identity to the mature polypeptide of SEQ ID NO: 11 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 11 or the mature polypeptide shown in SEQ ID NO 12, e.g. at least 80% or at least 90% of the DNase activity of the mature polypeptide.

In a particular embodiment, the invention relates to polypeptides having a sequence identity to the mature polypeptide of SEQ ID NO: 14 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 14 or the mature polypeptide shown in SEQ ID NO 15, e.g. at least 80% or at least 90% of the DNase activity of the mature polypeptide.

In a particular embodiment, the invention relates to polypeptides having a sequence identity to the mature polypeptide of SEQ ID NO: 17 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 17 or the mature polypeptide shown in SEQ ID NO 18, e.g. at least 80% or at least 90% of the DNase activity of the mature polypeptide.

In a particular embodiment, the invention relates to polypeptides having a sequence identity to the mature polypeptide of SEQ ID NO: 20 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 20 or the mature polypeptide shown in SEQ ID NO 21, e.g. at least 80% or at least 90% of the DNase activity of the mature polypeptide.

In a particular embodiment, the invention relates to polypeptides having a sequence identity to the mature polypeptide of SEQ ID NO: 23 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 23 or the mature polypeptide shown in SEQ ID NO 24, e.g. at least 80% or at least 90% of the DNase activity of the mature polypeptide.

In a particular embodiment, the invention relates to polypeptides having a sequence identity to the mature polypeptide of SEQ ID NO: 26 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 26 or the mature polypeptide shown in SEQ ID NO 27, e.g. at least 80% or at least 90% of the DNase activity of the mature polypeptide.

In a particular embodiment, the invention relates to polypeptides having a sequence identity to the mature polypeptide of SEQ ID NO: 29 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 29 or the mature polypeptide shown in SEQ ID NO 30, e.g. at least 80% or at least 90% of the DNase activity of the mature polypeptide.

In a particular embodiment, the invention relates to polypeptides having a sequence identity to the mature polypeptide of SEQ ID NO: 32 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 32 or the mature polypeptide shown in SEQ ID NO 33, e.g. at least 80% or at least 90% of the DNase activity of the mature polypeptide.

In a particular embodiment, the invention relates to polypeptides having a sequence identity to the mature polypeptide of SEQ ID NO: 35 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 35 or the mature polypeptide shown in SEQ ID NO 36, e.g. at least 80% or at least 90% of the DNase activity of the mature polypeptide.

In a particular embodiment, the invention relates to polypeptides having a sequence identity to the mature polypeptide of SEQ ID NO: 38 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 38 or the mature polypeptide shown in SEQ ID NO 39, e.g. at least 80% or at least 90% of the DNase activity of the mature polypeptide.

In a particular embodiment, the invention relates to polypeptides having a sequence identity to the mature polypeptide of SEQ ID NO: 41 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 41 or the mature polypeptide shown in SEQ ID NO 42, e.g. at least 80% or at least 90% of the DNase activity of the mature polypeptide.

In a particular embodiment, the invention relates to polypeptides having a sequence identity to the mature polypeptide of SEQ ID NO: 44 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 44 or the mature polypeptide shown in SEQ ID NO 45, e.g. at least 80% or at least 90% of the DNase activity of the mature polypeptide.

In a particular embodiment, the invention relates to polypeptides having a sequence identity to the mature polypeptide of SEQ ID NO: 47 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 47 or the mature polypeptide shown in SEQ ID NO 48, e.g. at least 80% or at least 90% of the DNase activity of the mature polypeptide.

In a particular embodiment, the invention relates to polypeptides having a sequence identity to the mature polypeptide of SEQ ID NO: 50 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the DNase activity of the mature polypeptide of SEQ ID NO: 50 or the mature polypeptide shown in SEQ ID NO 51 One embodiment of the invention relates to a polypeptide selected from the group consisting of polypeptides:

(a) comprising or consisting of SEQ ID NO: 3 or the mature polypeptide of SEQ ID NO: 2;
(b) comprising or consisting of SEQ ID NO: 6 or the mature polypeptide of SEQ ID NO: 5;
(c) comprising or consisting of SEQ ID NO: 9 or the mature polypeptide of SEQ ID NO: 8;
(d) comprising or consisting of SEQ ID NO: 12 or the mature polypeptide of SEQ ID NO: 11;
(e) comprising or consisting of SEQ ID NO: 15 or the mature polypeptide of SEQ ID NO: 14;
(f) comprising or consisting of SEQ ID NO: 18 or the mature polypeptide of SEQ ID NO: 17;
(g) comprising or consisting of SEQ ID NO: 21 or the mature polypeptide of SEQ ID NO: 20;
(h) comprising or consisting of SEQ ID NO: 24 or the mature polypeptide of SEQ ID NO: 23;
(i) comprising or consisting of SEQ ID NO: 27 or the mature polypeptide of SEQ ID NO: 26;
(j) comprising or consisting of SEQ ID NO: 30 or the mature polypeptide of SEQ ID NO: 29;
(k) comprising or consisting of SEQ ID NO: 33 or the mature polypeptide of SEQ ID NO: 32;
(l) comprising or consisting of SEQ ID NO: 36 or the mature polypeptide of SEQ ID NO: 35;
(m) comprising or consisting of SEQ ID NO: 39 or the mature polypeptide of SEQ ID NO: 38;

(n) comprising or consisting of SEQ ID NO: 42 or the mature polypeptide of SEQ ID NO: 41;
(o) comprising or consisting of SEQ ID NO: 45 or the mature polypeptide of SEQ ID NO: 44;
(p) comprising or consisting of SEQ ID NO: 48 or the mature polypeptide of SEQ ID NO: 47; and
(q) comprising or consisting of SEQ ID NO: 51 or the mature polypeptide of SEQ ID NO: 50;

In some embodiments, the polypeptide has been isolated. A polypeptide of the present invention preferably comprises or consists of the amino acid sequence shown in SEQ ID NO: 3 or an allelic variant thereof; or is a fragment thereof having DNase activity. In another aspect, the polypeptide comprises or consists of the mature polypeptide of SEQ ID NO: 2. In another aspect, the polypeptide comprises or consists of amino acids 1 to 188 of SEQ ID NO: 2.

In one embodiment, the polypeptide preferably comprises or consists of the amino acid sequence shown in SEQ ID NO: 3; comprises the amino acid sequence shown in SEQ ID NO: 3 and a N-terminal and/or C-terminal His-tag and/or HQ-tag; comprises the amino acid sequence of SEQ ID NO: 3 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 3.

In some embodiments, the polypeptide has been isolated. A polypeptide of the present invention preferably comprises or consists of the amino acid sequence shown in SEQ ID NO: 6 or an allelic variant thereof; or is a fragment thereof having DNase activity. In another aspect, the polypeptide comprises or consists of the mature polypeptide of SEQ ID NO: 5. In another aspect, the polypeptide comprises or consists of amino acids 1 to 182 of SEQ ID NO: 5.

In one embodiment, the polypeptide preferably comprises or consists of the amino acid sequence shown in SEQ ID NO: 6; comprises the amino acid sequence shown in SEQ ID NO: 6 and a N-terminal and/or C-terminal His-tag and/or HQ-tag; comprises the amino acid sequence of SEQ ID NO: 6 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 6.

In some embodiments, the polypeptide has been isolated. A polypeptide of the present invention preferably comprises or consists of the amino acid sequence shown in SEQ ID NO: 9 or an allelic variant thereof; or is a fragment thereof having DNase activity. In another aspect, the polypeptide comprises or consists of the mature polypeptide of SEQ ID NO: 8. In another aspect, the polypeptide comprises or consists of amino acids 1 to 193 of SEQ ID NO: 8.

In one embodiment, the polypeptide preferably comprises or consists of the amino acid sequence shown in SEQ ID NO: 9; comprises the amino acid sequence shown in SEQ ID NO: 9 and a N-terminal and/or C-terminal His-tag and/or HQ-tag; comprises the amino acid sequence of SEQ ID NO: 9 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 9.

In some embodiments, the polypeptide has been isolated. A polypeptide of the present invention preferably comprises or consists of the amino acid sequence shown in SEQ ID NO: 12 or an allelic variant thereof; or is a fragment thereof having DNase activity. In another aspect, the polypeptide comprises or consists of the mature polypeptide of SEQ ID NO: 11. In another aspect, the polypeptide comprises or consists of amino acids 1 to 187 of SEQ ID NO: 11.

In one embodiment, the polypeptide preferably comprises or consists of the amino acid sequence shown in SEQ ID NO: 12; comprises the amino acid sequence shown in SEQ ID NO: 12 and a N-terminal and/or C-terminal His-tag and/or HQ-tag; comprises the amino acid sequence of SEQ ID NO: 12 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 12.

In some embodiments, the polypeptide has been isolated. A polypeptide of the present invention preferably comprises or consists of the amino acid sequence shown in SEQ ID NO: 15 or an allelic variant thereof; or is a fragment thereof having DNase activity. In another aspect, the polypeptide comprises or consists of the mature polypeptide of SEQ ID NO: 14. In another aspect, the polypeptide comprises or consists of amino acids 1 to 182 of SEQ ID NO: 14.

In one embodiment, the polypeptide preferably comprises or consists of the amino acid sequence shown in SEQ ID NO: 15; comprises the amino acid sequence shown in SEQ ID NO: 15 and a N-terminal and/or C-terminal His-tag and/or HQ-tag; comprises the amino acid sequence of SEQ ID NO: 15 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 15.

In some embodiments, the polypeptide has been isolated. A polypeptide of the present invention preferably comprises or consists of the amino acid sequence shown in SEQ ID NO: 15 or an allelic variant thereof; or is a fragment thereof having DNase activity. In another aspect, the polypeptide comprises or consists of the mature polypeptide of SEQ ID NO: 17. In another aspect, the polypeptide comprises or consists of amino acids 1 to 192 of SEQ ID NO: 17.

In one embodiment, the polypeptide preferably comprises or consists of the amino acid sequence shown in SEQ ID NO: 18; comprises the amino acid sequence shown in SEQ ID NO: 18 and a N-terminal and/or C-terminal His-tag and/or HQ-tag; comprises the amino acid sequence of SEQ ID NO: 18 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 18.

In some embodiments, the polypeptide has been isolated. A polypeptide of the present invention preferably comprises or consists of the amino acid sequence shown in SEQ ID NO: 21 or an allelic variant thereof; or is a fragment thereof having DNase activity. In another aspect, the polypeptide comprises or consists of the mature polypeptide of SEQ ID NO: 20. In another aspect, the polypeptide comprises or consists of amino acids 1 to 187 of SEQ ID NO: 20.

In one embodiment, the polypeptide preferably comprises or consists of the amino acid sequence shown in SEQ ID NO: 21; comprises the amino acid sequence shown in SEQ ID NO: 21 and a N-terminal and/or C-terminal His-tag and/or HQ-tag; comprises the amino acid sequence of SEQ ID NO: 21 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 21.

In some embodiments, the polypeptide has been isolated. A polypeptide of the present invention preferably comprises or consists of the amino acid sequence shown in SEQ ID NO: 24 or an allelic variant thereof; or is a fragment thereof having DNase activity. In another aspect, the polypeptide comprises or consists of the mature polypeptide of SEQ ID NO: 23. In another aspect, the polypeptide comprises or consists of amino acids 1 to 191 of SEQ ID NO: 23.

In one embodiment, the polypeptide preferably comprises or consists of the amino acid sequence shown in SEQ ID NO: 24; comprises the amino acid sequence shown in SEQ ID NO: 24 and a N-terminal and/or C-terminal His-tag and/or HQ-tag; comprises the amino acid sequence of SEQ ID NO: 24 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 24.

In some embodiments, the polypeptide has been isolated. A polypeptide of the present invention preferably comprises or consists of the amino acid sequence shown in SEQ ID NO: 27 or an allelic variant thereof; or is a fragment thereof having DNase activity. In another aspect, the polypeptide comprises or consists of the mature polypeptide of SEQ ID NO: 26. In another aspect, the polypeptide comprises or consists of amino acids 1 to 197 of SEQ ID NO: 26.

In one embodiment, the polypeptide preferably comprises or consists of the amino acid sequence shown in SEQ ID NO: 27; comprises the amino acid sequence shown in SEQ ID NO: 27 and a N-terminal and/or C-terminal His-tag and/or HQ-tag; comprises the amino acid sequence of SEQ ID NO: 27 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 27.

In some embodiments, the polypeptide has been isolated. A polypeptide of the present invention preferably comprises or consists of the amino acid sequence shown in SEQ ID NO: 30 or an allelic variant thereof; or is a fragment thereof having DNase activity. In another aspect, the polypeptide comprises or consists of the mature polypeptide of SEQ ID NO: 29. In another aspect, the polypeptide comprises or consists of amino acids 1 to 188 of SEQ ID NO: 29.

In one embodiment, the polypeptide preferably comprises or consists of the amino acid sequence shown in SEQ ID NO: 30; comprises the amino acid sequence shown in SEQ ID NO: 30 and a N-terminal and/or C-terminal His-tag and/or HQ-tag; comprises the amino acid sequence of SEQ ID NO: 30 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 30.

In some embodiments, the polypeptide has been isolated. A polypeptide of the present invention preferably comprises or consists of the amino acid sequence shown in SEQ ID NO: 33 or an allelic variant thereof; or is a fragment thereof having DNase activity. In another aspect, the polypeptide comprises or consists of the mature polypeptide of SEQ ID NO: 32. In another aspect, the polypeptide comprises or consists of amino acids 1 to 208 of SEQ ID NO: 32.

In one embodiment, the polypeptide preferably comprises or consists of the amino acid sequence shown in SEQ ID NO: 33; comprises the amino acid sequence shown in SEQ ID NO: 33 and a N-terminal and/or C-terminal His-tag and/or HQ-tag; comprises the amino acid sequence of SEQ ID NO: 33 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 33.

In some embodiments, the polypeptide has been isolated. A polypeptide of the present invention preferably comprises or consists of the amino acid sequence shown in SEQ ID NO: 36 or an allelic variant thereof; or is a fragment thereof having DNase activity. In another aspect, the polypeptide comprises or consists of the mature polypeptide of SEQ ID NO: 35. In another aspect, the polypeptide comprises or consists of amino acids 1 to 210 of SEQ ID NO: 35.

In one embodiment, the polypeptide preferably comprises or consists of the amino acid sequence shown in SEQ ID NO: 36; comprises the amino acid sequence shown in SEQ ID NO: 36 and a N-terminal and/or C-terminal His-tag and/or HQ-tag; comprises the amino acid sequence of SEQ ID NO: 36 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 36.

In some embodiments, the polypeptide has been isolated. A polypeptide of the present invention preferably comprises or consists of the amino acid sequence shown in SEQ ID NO: 39 or an allelic variant thereof; or is a fragment thereof having DNase activity. In another aspect, the polypeptide comprises or consists of the mature polypeptide of SEQ ID NO: 38. In another aspect, the polypeptide comprises or consists of amino acids 1 to 191 of SEQ ID NO: 38.

In one embodiment, the polypeptide preferably comprises or consists of the amino acid sequence shown in SEQ ID NO: 39; comprises the amino acid sequence shown in SEQ ID NO: 39 and a N-terminal and/or C-terminal His-tag and/or HQ-tag; comprises the amino acid sequence of SEQ ID NO: 39 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 39.

In some embodiments, the polypeptide has been isolated. A polypeptide of the present invention preferably comprises or consists of the amino acid sequence shown in SEQ ID NO: 42 or an allelic variant thereof; or is a fragment thereof having DNase activity. In another aspect, the polypeptide comprises or consists of the mature polypeptide of SEQ ID NO: 41. In another aspect, the polypeptide comprises or consists of amino acids 1 to 206 of SEQ ID NO: 41.

In one embodiment, the polypeptide preferably comprises or consists of the amino acid sequence shown in SEQ ID NO: 42; comprises the amino acid sequence shown in SEQ ID NO: 42 and a N-terminal and/or C-terminal His-tag and/or HQ-tag; comprises the amino acid sequence of SEQ ID NO: 42 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 42.

In some embodiments, the polypeptide has been isolated. A polypeptide of the present invention preferably comprises or consists of the amino acid sequence shown in SEQ ID NO: 45 or an allelic variant thereof; or is a fragment thereof having DNase activity. In another aspect, the polypeptide comprises or consists of the mature polypeptide of SEQ ID NO: 44. In another aspect, the polypeptide comprises or consists of amino acids 1 to 210 of SEQ ID NO: 44.

In one embodiment, the polypeptide preferably comprises or consists of the amino acid sequence shown in SEQ ID NO: 45; comprises the amino acid sequence shown in SEQ ID NO: 45 and a N-terminal and/or C-terminal His-tag and/or HQ-tag; comprises the amino acid sequence of SEQ ID NO: 45 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 45.

In some embodiments, the polypeptide has been isolated. A polypeptide of the present invention preferably comprises or consists of the amino acid sequence shown in SEQ ID NO: 48 or an allelic variant thereof; or is a fragment thereof having DNase activity. In another aspect, the polypeptide comprises or consists of the mature polypeptide of SEQ ID NO: 47. In another aspect, the polypeptide comprises or consists of amino acids 1 to 193 of SEQ ID NO: 47.

In one embodiment, the polypeptide preferably comprises or consists of the amino acid sequence shown in SEQ ID NO: 48; comprises the amino acid sequence shown in SEQ ID NO: 48 and a N-terminal and/or C-terminal His-tag and/or HQ-tag; comprises the amino acid sequence of SEQ ID NO: 48 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 48.

In some embodiments, the polypeptide has been isolated. A polypeptide of the present invention preferably comprises or consists of the amino acid sequence shown in SEQ ID NO: 51 or an allelic variant thereof; or is a fragment thereof having DNase activity. In another aspect, the polypeptide comprises or consists of the mature polypeptide of SEQ ID NO: 50. In another aspect, the polypeptide comprises or consists of amino acids 1 to 210 of SEQ ID NO: 50.

In one embodiment, the polypeptide preferably comprises or consists of the amino acid sequence shown in SEQ ID NO: 51; comprises the amino acid sequence shown in SEQ ID NO: 51 and a N-terminal and/or C-terminal His-tag and/or HQ-tag; comprises the amino acid sequence of SEQ ID NO: 51 and a N-terminal and/or C-terminal extension of between 1 and 10 amino acids; or is a fragment thereof having DNase activity and having at least 50% such as at least 60%, at least 70%, at least 75%, at least 80%, at least 85%, at least 90%, at least 95%, at least 96%, at least 97%, at least 98% or at least 99% of the length of SEQ ID NO: 51.

In one embodiment, the present invention relates to variants of the mature polypeptide shown in SEQ ID NO: 3 comprising a substitution, deletion, and/or insertion at one or more (e.g., several) positions. In some embodiments, the number of amino acid substitutions, deletions and/or insertions introduced into the mature polypeptide shown in SEQ ID NO: 3 is up to 10, e.g., 1, 2, 3, 4, 5, 6, 7, 8, 9, or 10.

In one embodiment, the present invention relates to variants of the mature polypeptide shown in SEQ ID NO: 6 comprising a substitution, deletion, and/or insertion at one or more (e.g., several) positions. In some embodiments, the number of amino acid substitutions, deletions and/or insertions introduced into the mature polypeptide shown in SEQ ID NO: 6 is up to 10, e.g., 1, 2, 3, 4, 5, 6, 7, 8, 9, or 10.

In one embodiment, the present invention relates to variants of the mature polypeptide shown in SEQ ID NO: 9 comprising a substitution, deletion, and/or insertion at one or more (e.g., several) positions. In some embodiments, the number of amino acid substitutions, deletions and/or insertions introduced into the mature polypeptide shown in SEQ ID NO: 9 is up to 10, e.g., 1, 2, 3, 4, 5, 6, 7, 8, 9, or 10.

In one embodiment, the present invention relates to variants of the mature polypeptide shown in SEQ ID NO: 12 comprising a substitution, deletion, and/or insertion at one or more (e.g., several) positions. In some embodiments, the number of amino acid substitutions, deletions and/or insertions introduced into the mature polypeptide shown in SEQ ID NO: 12 is up to 10, e.g., 1, 2, 3, 4, 5, 6, 7, 8, 9, or 10.

In one embodiment, the present invention relates to variants of the mature polypeptide shown in SEQ ID NO: 15 comprising a substitution, deletion, and/or insertion at one or more (e.g., several) positions. In some embodiments, the number of amino acid substitutions, deletions and/or insertions introduced into the mature polypeptide shown in SEQ ID NO: 15 is up to 10, e.g., 1, 2, 3, 4, 5, 6, 7, 8, 9, or 10.

In one embodiment, the present invention relates to variants of the mature polypeptide shown in SEQ ID NO: 18 comprising a substitution, deletion, and/or insertion at one or more (e.g., several) positions. In some embodiments, the number of amino acid substitutions, deletions and/or insertions introduced into the mature polypeptide shown in SEQ ID NO: 18 is up to 10, e.g., 1, 2, 3, 4, 5, 6, 7, 8, 9, or 10.

In one embodiment, the present invention relates to variants of the mature polypeptide shown in SEQ ID NO: 21 comprising a substitution, deletion, and/or insertion at one or more (e.g., several) positions. In some embodiments, the number of amino acid substitutions, deletions and/or insertions introduced into the mature polypeptide shown in SEQ ID NO: 21 is up to 10, e.g., 1, 2, 3, 4, 5, 6, 7, 8, 9, or 10.

In one embodiment, the present invention relates to variants of the mature polypeptide shown in SEQ ID NO: 24 comprising a substitution, deletion, and/or insertion at one or more (e.g., several) positions. In some embodiments, the number of amino acid substitutions, deletions and/or insertions introduced into the mature polypeptide shown in SEQ ID NO: 24 is up to 10, e.g., 1, 2, 3, 4, 5, 6, 7, 8, 9, or 10.

In one embodiment, the present invention relates to variants of the mature polypeptide shown in SEQ ID NO: 27 comprising a substitution, deletion, and/or insertion at one or more (e.g., several) positions. In some embodiments, the number of amino acid substitutions, deletions and/or insertions introduced into the mature polypeptide shown in SEQ ID NO: 27 is up to 10, e.g., 1, 2, 3, 4, 5, 6, 7, 8, 9, or 10.

In one embodiment, the present invention relates to variants of the mature polypeptide shown in SEQ ID NO: 30 comprising a substitution, deletion, and/or insertion at one or more (e.g., several) positions. In some embodiments, the number of amino acid substitutions, deletions and/or insertions introduced into the mature polypeptide shown in SEQ ID NO: 30 is up to 10, e.g., 1, 2, 3, 4, 5, 6, 7, 8, 9, or 10.

In one embodiment, the present invention relates to variants of the mature polypeptide shown in SEQ ID NO: 33 comprising a substitution, deletion, and/or insertion at one or more (e.g., several) positions. In some embodiments, the number of amino acid substitutions, deletions and/or insertions introduced into the mature polypeptide shown in SEQ ID NO: 33 is up to 10, e.g., 1, 2, 3, 4, 5, 6, 7, 8, 9, or 10.

In one embodiment, the present invention relates to variants of the mature polypeptide shown in SEQ ID NO: 36 comprising a substitution, deletion, and/or insertion at one or more (e.g., several) positions. In some embodiments, the number of amino acid substitutions, deletions and/or insertions introduced into the mature polypeptide shown in SEQ ID NO: 36 is up to 10, e.g., 1, 2, 3, 4, 5, 6, 7, 8, 9, or 10.

In one embodiment, the present invention relates to variants of the mature polypeptide shown in SEQ ID NO: 39 comprising a substitution, deletion, and/or insertion at one or more (e.g., several) positions. In some embodiments, the number of amino acid substitutions, deletions and/or insertions introduced into the mature polypeptide shown in SEQ ID NO: 39 is up to 10, e.g., 1, 2, 3, 4, 5, 6, 7, 8, 9, or 10.

In one embodiment, the present invention relates to variants of the mature polypeptide shown in SEQ ID NO: 42 comprising a substitution, deletion, and/or insertion at one or more (e.g., several) positions. In some embodiments, the number of amino acid substitutions, deletions and/or insertions introduced into the mature polypeptide shown in SEQ ID NO: 42 is up to 10, e.g., 1, 2, 3, 4, 5, 6, 7, 8, 9, or 10.

In one embodiment, the present invention relates to variants of the mature polypeptide shown in SEQ ID NO: 45 comprising a substitution, deletion, and/or insertion at one or more (e.g., several) positions. In some embodiments, the number of amino acid substitutions, deletions and/or insertions introduced into the mature polypeptide shown in SEQ ID NO: 45 is up to 10, e.g., 1, 2, 3, 4, 5, 6, 7, 8, 9, or 10.

In one embodiment, the present invention relates to variants of the mature polypeptide shown in SEQ ID NO: 45 comprising a substitution, deletion, and/or insertion at one or more (e.g., several) positions. In some embodiments, the number of amino acid substitutions, deletions and/or insertions introduced into the mature polypeptide shown in SEQ ID NO: 48 is up to 10, e.g., 1, 2, 3, 4, 5, 6, 7, 8, 9, or 10.

In one embodiment, the present invention relates to variants of the mature polypeptide shown in SEQ ID NO: 45 comprising a substitution, deletion, and/or insertion at one or more (e.g., several) positions. In some embodiments, the number of amino acid substitutions, deletions and/or insertions introduced into the mature polypeptide shown in SEQ ID NO: 51 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for DNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having DNase Activity

A polypeptide having DNase activity of the present invention may be obtained from microorganisms of any genus, in particular from a fungal microorganism. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is a *Rhizoctonia* polypeptide, e.g., a polypeptide obtained from *Rhizoctonia solani*.

In one aspect, the polypeptide is a *Cercospora* polypeptide, e.g., a polypeptide obtained from *Cercospora fusimaculans*.

In one aspect, the polypeptide is a *Cladosporium* polypeptide, e.g., a polypeptide obtained from *Cladosporium cladosporioides*.

In one aspect, the polypeptide is a *Irpex* polypeptide, e.g., a polypeptide obtained from *Irpex lacteus*.

In one aspect, the polypeptide is a *Phlebia* polypeptide, e.g., a polypeptide obtained from *Phlebia subochracea*.

In one aspect, the polypeptide is a *Mortierella* polypeptide, e.g., a polypeptide obtained from *Mortierella humilis*.

In one aspect, the polypeptide is a *Stropharia* polypeptide, e.g., a polypeptide obtained from *Stropharia semiglobata*.

In one aspect, the polypeptide is a *Physisporinus* polypeptide, e.g., a polypeptide obtained from *Physisporinus sanguinolentus*.

In one aspect, the polypeptide is a *Deconica* polypeptide, e.g., a polypeptide obtained from *Deconica coprophila*.

In one aspect, the polypeptide is a *Marasmius* polypeptide, e.g., a polypeptide obtained from *Marasmius oreades*.

In one aspect, the polypeptide is a *Pholiota* polypeptide, e.g., a polypeptide obtained from *Pholiota squarrosa*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and *Agricultural Research* Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In some embodiments, the polynucleotide encoding the polypeptide of the present invention has been isolated.

One embodiment of the invention relates to a polypeptide encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO 1, SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40 or SEQ ID NO: 43, SEQ ID NO: 46, SEQ ID NO: 49.

In one embodiment, the present invention relates to a polynucleotide encoding a polypeptide having DNase activity, wherein the polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 10 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 13 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 16 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 19 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 22 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 25 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 28 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 31 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 34 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 37 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 40 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 43 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 46 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

In one embodiment, the present invention relates to a polynucleotide encoding a polypeptide having DNase activity, wherein the polynucleotide having a sequence identity to the mature polypeptide coding sequence of SEQ ID NO: 49 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polynucleotide has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences. The control sequence may be heterologous to the host cell.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences, which may be heterologous to each other, may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. The control sequence(s) may be heterologous to the host cell. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus altitudinis*, *Bacillus amyloliquefaciens*, *B. amyloliquefaciens* subsp. *plantarum*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus methylotrophicus*, *Bacillus pumilus*, *Bacillus safensis*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J.*

*Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No. 9*, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides having DNase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In one embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells.

In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may, for example, be produced by a method described in WO 90/15861 or WO 2010/096673.

Enzyme Compositions

The invention relates to compositions comprising a DNase of the present invention in combination with one or more additional component(s). The choice of additional components is within the skill of the artisan and includes conventional ingredients, including the exemplary non-limiting components set forth below.

One embodiment of the invention relates to a composition comprising:
  a) at least 0.001 ppm of at least one polypeptide having DNase activity, wherein the DNase is selected for the group consisting of: SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51 and polypeptides having at least 80% sequence identity hereto;
  b) one or more adjunct ingredient.

One embodiment of the invention relates to a cleaning composition comprising:
  a) at least 0.001 ppm of at least one polypeptide having DNase activity, wherein the DNase is selected for the group consisting of: SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51 and polypeptides having at least 80% sequence identity hereto;

b) one or more cleaning composition component, preferably selected from surfactants, builders, bleach components, polymers, dispersing agents and additional enzymes.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.1% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.1% to about 10% by weight of a zwitterionic surfactant. Non-limiting examples of zwitterionic surfactants include betaines such as alkyldimethylbetaines, sulfobetaines, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-KN-methanylylidene)triphenolato-κ3O]manganese(II). The bleach catalysts may also be other metal compounds; such as iron or cobalt complexes.

In some embodiments, where a source of a peracid is included, an organic bleach catalyst or bleach booster may be used having one of the following formulae:

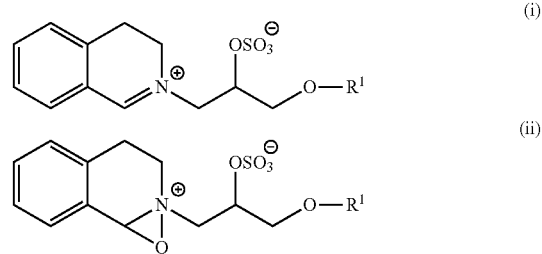

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain Ci-C20-alkyl groups (e.g., C1-C20-alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-κ30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The detergent additive as well as the detergent composition may comprise one or more additional enzymes such as one or more lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii,* or *H. insolens*. Suitable mannanases are described in WO 1999/064619. A commercially available mannanase is Mannaway (Novozymes A/S).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes A/S).

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from Thermobifida fusca (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases:

Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T491+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K
E187P+I203Y+R458N+T459S+D460T+G476K wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21D+D97N+V128I wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz 5110 (from Genencor International Inc./DuPont).

Proteases:

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., *Protein Engng.* 4 (1991) 719-737 and Siezen et al. *Protein Science* 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO 92/175177, WO 01/016285, WO 02/026024 and WO 02/016547. Examples of trypsin-like proteases are trypsin (e.g. of porcine or bovine origin) and the *Fusarium* protease described in WO 89/06270, WO 94/25583 and WO 05/040372, and the chymotrypsin proteases derived from *Cellumonas* described in WO 05/052161 and WO 05/052146.

A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of metalloproteases are the neutral metalloprotease as described in WO07/044993 (Genencor Int.) such as those derived from *Bacillus amyloliquefaciens*.

Examples of useful proteases are the variants described in: WO 92/19729, WO 96/034946, WO 98/20115, WO 98/20116, WO 99/011768, WO 01/44452, WO 03/006602, WO 04/03186, WO 04/041979, WO 07/006305, WO 11/036263, WO 11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO 1 of WO 2016/001449. More preferred the subtilase variants may comprise one or more of the following mutations: S3T, V41, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A, R269H. The protease variants are preferably variants of the *Bacillus lentus* protease (Savinase®) shown in SEQ ID NO 1 of WO 2016/001449, the *Bacillus amyloliquefaciens* protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO 2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™ Purafect®™, Effectenz P1050™ Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea*, as disclosed in WO 97/08325; or from *Myceliophthora thermophila*, as disclosed in WO 95/33836.

Dispersants

The detergent compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, CI-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040. Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%.

Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Detergent Formulations

The DNase of the invention may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said the multi enzyme co-granule comprises from 10 to 98 wt % moisture sink component and the composition additionally comprises from 20 to 80 wt % detergent moisture sink component. A co-granule may comprise a DNase of the invention and e.g. one or more enzymes selected from the group consisting of hemicellulases, proteases, care cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

In one aspect, the present invention provides a granule, which comprises:

(a) a core comprising a polypeptide comprising the amino acid sequence shown in SEQ ID NO 3, SEQ ID NO 6, SEQ ID NO 9, SEQ ID NO 12, SEQ ID NO 15, SEQ ID NO 18, SEQ ID NO 21, SEQ ID NO 24, SEQ ID NO 27, SEQ ID NO 30, SEQ ID NO 33, SEQ ID NO 36, SEQ ID NO 39, SEQ ID NO 42, SEQ ID NO 45, SEQ ID NO 48, SEQ ID NO 51 or polypeptides having at least 80% sequence identity hereto, and (b) optionally a coating consisting of one or more layer(s) surrounding the core.

In one aspect, the invention relates to a granule which comprises:

(a) a core comprising a polypeptide having DNase activity and wherein the polypeptide comprises one or more of the motifs selected from the motifs PL[KR]E[AG]W (SEQ ID NO 56), and C[TK]Y[VI][RC][AS]WI (SEQ ID NO 57), and (b) optionally a coating consisting of one or more layer(s) surrounding the core Uses The polypeptides of the invention having DNase activity may be used for deep cleaning of an item, such as a textile. In one embodiment of the invention relates to the use of a DNase according to the invention for prevention reduction or removal of malodor. One embodiment of the invention relates to the use of an DNase of the invention for prevention or reduction of anti-redeposition and improvement of whiteness of a textile subjected to multiple washes. When the biofilm components e.g. DNA of the extracellular biofilm matrix are removed, or reduced the stickiness coursed caused by biofilm is also reduced. The DNases of the invention therefore reduced the greyness of textiles when applied in the compositions of the invention to a cleaning process such as laundry. One embodiment of the invention relates to the use of a polypeptide according to the invention for deep cleaning of an item, wherein the item is a textile. One embodiment of the invention relates to the use of a polypeptide according to the invention (i) for preventing, reducing or removing stickiness of the item;
(ii) for pretreating stains on the item;
(iii) for preventing, reducing or removing redeposition of soil during a wash cycle;
(iv) for preventing, reducing or removing adherence of soil to the item;
(v) for maintaining or improving whiteness of the item;
(vi) for preventing, reducing or removal malodor from the item, wherein the item is a textile.

In one aspect, the invention relates to use of a polypeptide of the invention having DNase activity for cleaning of a textile item in the presence of sulphite. In a particular embodiment of this aspect of the invention the polypeptide is an *R. solani* DNase selected from the group consisting of:

a polypeptide having at least 80% sequence identity, for example at least at least 85%, at least 90% or at least 95% identity, to the polypeptide of SEQ ID NO: 33;

a polypeptide having at least 80% sequence identity, for example at least at least 85%, at least 90% or at least 95% identity, to the polypeptide of SEQ ID NO: 36;

a polypeptide having at least 80% sequence identity, for example at least at least 85%, at least 90% or at least 95% identity, to the polypeptide of SEQ ID NO: 39;

a polypeptide having at least 80% sequence identity, for example at least at least 85%, at least 90% or at least 95% identity, to the polypeptide of SEQ ID NO: 42;

a polypeptide having at least 80% sequence identity, for example at least at least 85%, at least 90% or at least 95% identity, to the polypeptide of SEQ ID NO: 45;

a polypeptide having at least 80% sequence identity, for example at least at least 85%, at least 90% or at least 95% identity, to the polypeptide of SEQ ID NO: 48; and a polypeptide having at least 80% sequence identity, for example at least at least 85%, at least 90% or at least 95% identity, to the polypeptide of SEQ ID NO: 51.

In a preferred embodiment, the polypeptide for use for cleaning of a textile item in the presence of sulfite has at least 80% sequence identity to the polypeptide of SEQ ID NO: 45, for example at least at least 85%, at least 90%, at least 91%, at least 92%, at least 93%, at least 94%, at least 95%, at least 96%, at least 97%, at least 98%, at least 99% or 100% sequence identity.

Sulfites are used as a preservative e.g. in unidose detergent compositions. However, wash performance of enzymes such as DNases can be negatively influenced by the presence of sulfite. It has surprisingly been found that an *R. solani* DNase of the invention shows improved wash performance with increasing concentrations of sulphite.

It is contemplated that the DNase may be used in detergent compositions comprising any amount of sulfite and in any form typically used in detergent compositions, e.g. a salt such as potassium sulfite or sodium sulfite. The detergent composition may, for example, comprise at least about 0.01% (w/v or w/w, depending on whether the composition is a liquid or a powder) of a sulfite compound, e.g. at least about 0.05%, at least about 0.1% or at least about 0.2%, and for example up to about 2%, e.g. up to about 1% or up to about 0.5% of a sulfite compound.

The invention is further summarized in the following paragraphs:
1. Use of a polypeptide having DNase activity and comprising a motif selected from PL[KR]E[AG]W (SEQ ID NO 56) or C[TK]Y[VI][RC][AS]WI (SEQ ID NO 57) for deep cleaning of an item, wherein the item is a textile.
2. Use according to paragraph 1 for preventing, reducing or removing stickiness of the item.
3. Use according to any of paragraphs 1 or 2 for pre-treating stains on the item.
4. Use according to any of paragraphs 1-3 for preventing, reducing or removing re-deposition of soil during a wash cycle.
5. Use according to any of paragraphs 1-4 for preventing, reducing or removing adherence of soil to the item.
6. Use according to any of the preceding paragraphs for maintaining or improving the whiteness of the item.
7. Use according to any of the preceding paragraphs, wherein a malodor is reduced or removed from the item.
8. Use according to any of the preceding composition paragraphs, wherein the surface is a textile surface.
9. Use according to any of the preceding composition paragraphs, wherein the textile is made of cotton, cotton/polyester, polyester, polyamide, polyacrylic and/or silk.
10. Use according to any of the preceding paragraphs, wherein the polypeptide is a polypeptide of paragraphs 47-61
11. A composition comprising a polypeptide having DNase activity, the polypeptide comprising a motif selected from PL[KR]E[AG]W (SEQ ID NO 56) or C[TK]Y[VI][RC][AS]WI (SEQ ID NO 57), and at least one detergent adjunct ingredient.
12. Composition according to paragraph 11, wherein the polypeptide is the polypeptide of paragraphs 45-59.
13. Composition according to any of the preceding composition paragraphs, wherein the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.
14. Composition according to any of the preceding composition paragraphs wherein the composition comprises from about 5 wt % to about 50 wt %, from about 5 wt % to about 40 wt %, from about 5 wt % to about 30 wt %, from about 5 wt % to about 20 wt %, from about 5 wt % to about 10 wt % anionic surfactant, preferably selected from linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.
15. Composition according to any of the preceding composition paragraphs wherein the composition comprises from about 10 wt % to about 50 wt % of at least one builder, preferably selected from citric acid, methylglycine-N,N-diacetic acid (MGDA) and/or glutamic acid-N,N-diacetic acid (GLDA) and mixtures thereof.
16. Composition according to any of the preceding paragraphs comprising from about 5 wt % to about 40 wt % nonionic surfactant, and from about 0 wt % to about 5 wt % anionic surfactant.
17. Composition according to paragraph 16, wherein the nonionic surfactant is selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA) and combinations thereof.
18. Composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.
19. Composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.
20. Composition according to any of the preceding composition paragraphs, wherein the composition is a cleaning composition selected from liquid detergent, powder detergent and granule detergent compositions.

21. Composition according to any of the preceding composition paragraphs wherein the polypeptide comprises one or more motif(s) selected from PL[KR]E[AG]W (SEQ ID NO 56) and C[TK]Y[VI][RC][AS]WI (SEQ ID NO 57), and wherein the polypeptide is selected from the group consisting of polypeptides having the amino acid sequence of SEQ ID NO 3, 6, 9, 12, 15, 18, 21, 24, 27, 30, 33, 36, 39, 42, 45, 48 or 51 and polypeptides having at least 80% sequence identity hereto.

22. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) comprises the amino acid sequence shown SEQ ID NO 3 or a sequence having at least 60% sequence identity hereto, e.g. at least 70%, at least 80% or at least 90%.

23. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 6 or a sequence having at least 60% sequence identity hereto, e.g. at least 70%, at least 80% or at least 90%.

24. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 9 or a sequence having at least 60% sequence identity hereto, e.g. at least 70%, at least 80% or at least 90%.

25. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 12 or a sequence having at least 60% sequence identity hereto, e.g. at least 70%, at least 80% or at least 90%.

26. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 15 or a sequence having at least 60% sequence identity hereto, e.g. at least 70%, at least 80% or at least 90%.

27. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 18 or a sequence having at least 60% sequence identity hereto, e.g. at least 70%, at least 80% or at least 90%.

28. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 21 or a sequence having at least 60% sequence identity hereto, e.g. at least 70%, at least 80% or at least 90%.

29. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 24 or a sequence having at least 60% sequence identity hereto, e.g. at least 70%, at least 80% or at least 90%.

30. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 27 or a sequence having at least 60% sequence identity hereto, e.g. at least 70%, at least 80% or at least 90%.

31. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 30 or a sequence having at least 60% sequence identity hereto, e.g. at least 70%, at least 80% or at least 90%.

32. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 33 or a sequence having at least 60% sequence identity hereto, e.g. at least 70%, at least 80% or at least 90%.

33. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 36 or a sequence having at least 60% sequence identity hereto, e.g. at least 70%, at least 80% or at least 90%.

34. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 39 or a sequence having at least 60% sequence identity hereto, e.g. at least 70%, at least 80% or at least 90%.

35. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 42 or a sequence having at least 60% sequence identity hereto, e.g. at least 70%, at least 80% or at least 90%.

36. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 45 or a sequence having at least 60% sequence identity hereto, e.g. at least 70%, at least 80% or at least 90%.

37. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) and comprises the amino acid sequence shown SEQ ID NO 48 or a sequence having at least 60% sequence identity hereto, e.g. at least 70%, at least 80% or at least 90%.

38. Composition according to any of the preceding composition paragraphs wherein the polypeptide comprising one or more motif(s) selected from PL[KR]E[AG]W (SEQ ID NO 56) or C[TK]Y[VI][RC][AS]WI (SEQ ID NO 57) comprises the amino acid sequence shown in SEQ ID NO 51 or a sequence having at least 60% sequence identity hereto, e.g. at least 70%, at least 80% or at least 90%.

39. A method for laundering an item comprising the steps of:
   a. Exposing an item to a wash liquor comprising a polypeptide of paragraphs 51-65 or a composition according to any of paragraphs 11-38;
   b. Completing at least one wash cycle; and
   c. Optionally rinsing the item,
   wherein the item is a textile.

40. A method of treating an item, wherein the item is preferably a textile, said method comprising the step of exposing an item to a polypeptide selected from the group consisting of a polypeptide having at least 80% sequence identity to the mature polypeptide of SEQ ID NO: 2, 5, 8, 11, 14, 17, 20, 23, 26, 29, 32, 35, 38, 41, 44, 47 or 50; a wash liquor comprising said polypeptide or a detergent composition according to any preceding paragraph.

41. Method according to any preceding paragraph, wherein the pH of the wash liquor is in the range of 1 to 11.

42. Method according to any of the preceding method paragraphs, wherein the pH of the wash liquor is in the range 5.5 to 11, such as in the range of 7 to 9, in the range of 7 to 8 or in the range of 7 to 8.5.

43. Method according to any of the preceding method paragraphs, wherein the temperature of the wash liquor is in the range of 5° C. to 95° C., or in the range of 100° C. to 80° C., in the range of 10° C. to 70° C., in the range of 10° C. to 60° C., in the range of 10° C. to 50° C., in the range of 15° C. to 40° C., in the range of 20° C. to 40° C., in the range of 15° C. to 30° C. or in the range of 20° C. to 30° C.

44. Method according to any of the preceding method paragraphs, wherein the temperature of the wash liquor is from about 20° C. to about 40° C.

45. Method according to any of the preceding method paragraphs, wherein the temperature of the wash liquor is from about 15° C. to about 30° C.

46. Method according to any of the preceding method paragraphs, wherein stains present on the item is pretreated with a polypeptide of paragraphs 53-68 or a detergent composition according to any of paragraphs 11-38.

47. Method according to any of the preceding method paragraphs, wherein stickiness of the item is reduced.

48. Method according to any of the preceding method paragraphs, wherein redeposition of soil is reduced.

49. Method according to any of the preceding method paragraphs, wherein adherence of soil to the item is reduced or removed.

50. Method according to any of the preceding method paragraphs, wherein whiteness of the item is maintained or improved.

51. Method according to any of the preceding method paragraphs, wherein malodor is reduced or removed from the item.

52. Method according to any of the preceding method paragraphs, wherein the concentration of the polypeptide having DNase activity in the wash liquor is at least 0,001 mg of polypeptide, such as at least 5 mg of protein, preferably at least 10 mg of protein, more preferably at least 15 mg of protein, per liter of wash liquor, optionally the concentration of polypeptide in the wash liquor is in the range 0,002 mg/L to 2 mg/L, such as 0.02 mg/L til 2 mg/L, such as 0.2 mg/L to 2 mg/L or in the range of 0,0001 mg/L to 10 mg/L or in the range of in the range of 0,001 mg/L to 10 mg/L, or in the range of 0.01 mg/L to 10 mg/L, or in in the range of 0.1 mg/L to 10 mg/L per liter of wash liquor, optionally the concentration of the polypeptide of the invention is 0.0001% to 2 wt %, such as 0.001 to 0.1 wt %, such as 0.005 to 0.1 wt %, such as 0.01 to 0.1 wt %, such as 0.01 to 0.5 wt % or most preferred 0.002 to 0.09 wt % in the total detergent concentration.

53. A polypeptide having DNase activity, selected from the group consisting of:
   a. a polypeptide having at least 80% sequence identity to the mature polypeptide of SEQ ID NO: 2, 5, 8, 11, 14, 17, 20, 23, 26, 29, 32, 35, 38, 41, 44, 47 or 50 or a polypeptide having at least 80% sequence identity to the mature polypeptide shown in SEQ ID NO: 3, 6, 9, 12, 15, 18, 21, 24, 27, 30, 33, 36, 39, 42, 45, 48 or 51;
   b. a polypeptide encoded by a polynucleotide that hybridizes under low stringency conditions with
      i. the mature polypeptide coding sequence of SEQ ID NO: 1, 4, 7, 10, 13, 16, 19, 22, 25, 28, 31, 34, 37, 40, 43, 46 or 49;
      ii. the cDNA sequence thereof, or
      iii. the full-length complement of (i) or (ii);
   c. a polypeptide encoded by a polynucleotide having at least 60% sequence identity to the mature polypeptide coding sequence of SEQ ID NO: 1, 4, 7, 10, 13, 16, 19, 22, 25, 28, 31, 34, 37, 40, 43, 46, 49 or the cDNA sequence thereof;
   d. a variant of the mature polypeptide shown in SEQ ID NO: 23, 6, 9, 12, 15, 18, 21, 24, 27, 30, 33, 36, 39, 42, 45, 48 or 51 comprising a substitution, deletion, and/or insertion at one or more positions or a variant of the mature polypeptide shown in SEQ ID NO: 3, 6, 9, 12, 15, 18, 21, 24, 27, 30, 33, 36, 39, 42, 45, 48 or 51 comprising a substitution, deletion, and/or insertion at one or more positions; and
   e. a fragment of the polypeptide of (a), (b), (c), or (d) that comprises one or more of the motifs selected from PL[KR]E[AG]W (SEQ ID NO 56) or C[TK]Y[VI][RC][AS]WI (SEQ ID NO 57);

54. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, 5, 8, 11, 14, 17, 20, 23, 26, 29, 32, 35, 38, 41, 44, 47, 50 or to the mature polypeptide shown in SEQ ID NO: 3, 6, 9, 12, 15, 18, 21, 24, 27, 30, 33, 36, 39, 42, 45, 48 or 51.

55. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2 or to the mature polypeptide shown in SEQ ID NO: 3.

56. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 5 or to the mature polypeptide shown in SEQ ID NO: 6.

57. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 8 or to the mature polypeptide shown in SEQ ID NO: 9.

58. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 11 or to the mature polypeptide shown in SEQ ID NO: 12.

59. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 14 or to the mature polypeptide shown in SEQ ID NO: 15.

60. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 17 or to the mature polypeptide shown in SEQ ID NO: 18.

61. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 20 or to the mature polypeptide shown in SEQ ID NO: 21.

62. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 23 or to the mature polypeptide shown in SEQ ID NO: 24.

63. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 26 or to the mature polypeptide shown in SEQ ID NO: 27.

64. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 29 or to the mature polypeptide shown in SEQ ID NO: 30.

65. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 32 or to the mature polypeptide shown in SEQ ID NO: 33.

66. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 35 or to the mature polypeptide shown in SEQ ID NO: 36.

67. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 38 or to the mature polypeptide shown in SEQ ID NO: 39.

68. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 41 or to the mature polypeptide shown in SEQ ID NO: 42.

69. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 44 or to the mature polypeptide shown in SEQ ID NO: 45.

70. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 47 or to the mature polypeptide shown in SEQ ID NO: 48.

71. The polypeptide of paragraph 53, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 50 or to the mature polypeptide shown in SEQ ID NO: 53.

72. The polypeptide according to any of paragraphs 53 to 71, which is encoded by a polynucleotide that hybridizes under low stringency conditions, low-medium stringency conditions, medium stringency conditions, medium-high stringency conditions, high stringency conditions, or very high stringency conditions with
    i. the mature polypeptide coding sequence of SEQ ID NO: 1, 4, 7, 10, 13, 16, 19, 22, 25, 28, 31, 34, 37, 40, 43, 46 or 49,
    ii. the cDNA sequence thereof, or
    iii. the full-length complement of (i) or (ii).

73. The polypeptide according to any of paragraphs 53 to 72, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1, 4, 7, 10, 13, 16, 19, 22, 25, 28, 31, 34, 37, 40, 43, 46 or 49 or the cDNA sequence thereof.

74. The polypeptide according to any of paragraphs 53 to 72, comprising or consisting of SEQ ID NO: 3, 6, 9, 12, 15, 18, 21, 24, 27, 30, 33, 36, 39, 42, 45, 48, 51 or the mature polypeptide of SEQ ID NO: 2, 5, 8, 11, 14, 17, 20, 23, 26, 29, 32, 35, 38, 41, 44, 47 or 50.

75. The polypeptide according to any of paragraphs 51 to 69, which is a variant of the any of the polypeptides with SEQ ID NO: 3, 6, 9, 12, 15, 18, 21, 24, 27, 30, 33, 36, 39, 42, 45, 48 or 51 comprising a substitution, deletion, and/or insertion at one or more positions.
76. A polynucleotide encoding the polypeptide according to any of paragraphs 53-75.
77. A nucleic acid construct or expression vector comprising the polynucleotide of paragraph 76 operably linked to one or more optionally heterologous control sequences that direct the production of the polypeptide in an expression host.
78. A recombinant host cell comprising the polynucleotide of paragraph 76 operably linked to one or more optionally heterologous control sequences that direct the production of the polypeptide.
79. A method of producing the polypeptide of any of paragraphs 53-75, comprising cultivating a cell, which in its wild-type form produces the polypeptide, under conditions conducive for production of the polypeptide.
80. The method of paragraph 79, further comprising recovering the polypeptide.
81. A method of producing a polypeptide according to any of paragraphs 53-75, comprising cultivating the host cell of paragraph 80 under conditions conducive for production of the polypeptide.
82. The method of paragraph 81, further comprising recovering the polypeptide.
83. A nucleic acid construct or expression vector comprising a gene encoding a protein operably linked to the polynucleotide of paragraph 76, wherein the gene is foreign or heterologous to the polynucleotide encoding the signal peptide.
84. A recombinant host cell comprising a gene encoding a protein operably linked to the polynucleotide of paragraph 76, wherein the gene is foreign or heterologous to the polynucleotide encoding the signal peptide.
85. A method of producing a protein, comprising cultivating a recombinant host cell comprising a gene encoding a protein operably linked to the polynucleotide of paragraph 76, wherein the gene is foreign to the polynucleotide encoding the signal peptide, under conditions conducive for production of the protein.
86. The method of paragraph 85, further comprising recovering the protein.
87. Use of a polypeptide for cleaning of a textile item in the presence of sulfite, wherein the polypeptide is a DNase having at least 80% sequence identity to SEQ ID NO: 33, 36, 39, 42, 45, 48 or 51, preferably a DNase having at least 80% sequence identity to SEQ ID NO: 45.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

EXAMPLES

Assay I
Testing of DNase activity
DNase activity may be determined on DNase Test Agar with Methyl Green (BD, Franklin Lakes, N.J., USA), which is prepared according to the manual from the supplier. Briefly, 21 g of agar is dissolved in 500 ml water and then autoclaved for 15 min at 121° C. Autoclaved agar is tempered to 48° C. in a water bath, and 20 ml of agar is poured into Petri dishes and allowed to solidify by incubation overnight at room temperature. On solidified agar plates, 5 μl of enzyme solutions are added, and DNase activity is observed as colorless zones around the spotted enzyme solutions.

Assay II
DNase activity may be determined by fluorescence using a fluorescence-quenched DNA oligonucleotide probe. This probe emits a signal after nuclease degradation according to the manual from the supplier (DNase alert kit, Integrated DNA Technology, Coralville, Iowa, USA). Briefly, 5 μl of the substrate is added to 95 μl of DNase. If the signal is too high, further dilutions of DNase are performed in a suitable buffer. Kinetic curves are measured for 20 min at 22° C. using a Clariostar microplate reader (536 nm excitation, 556 nm emission).

Example 1: Cloning, Expression and Fermentation of DNases

DNase encoding genes were cloned from a variety of fungal strains that were isolated from environmental samples or obtained from culture collections. Other DNase encoding genes were found in publicly available genome sequences. Source materials for the DNases are described the tables 1 to 2 below.

TABLE 1

| Strain | Source country | Mature protein SEQ ID |
|---|---|---|
| Rhizoctonia solani 123E | EMBL: PRJNA227561 | SEQ ID NO: 48 |
| Rhizoctonia solani 9843 | Brazil | SEQ ID NO: 33 |
| Marasmius oreades | Denmark | SEQ ID NO: 6 |
| Physisporinus sanguinolentus | Denmark | SEQ ID NO: 18 |
| Irpex lacteus | Russia | SEQ ID NO: 27 |
| Pholiota squarrosa | Denmark | SEQ ID NO: 3 |
| Cladosporium cladosporioides | Brazil | SEQ ID NO: 24 |
| Deconica coprophila | Denmark | SEQ ID NO: 12 |
| Phlebia subochracea | Denmark | SEQ ID NO: 30 |
| Rhizoctonia solani AG-1 IB | EMBL: PRJEB40 | SEQ ID NO: 51 |
| Rhizoctonia solani AG-1 IA | EMBL: PRJNA354902 | SEQ ID NO: 42 |
| Stropharia semiglobata | Denmark | SEQ ID NO: 21 |
| Mortierella humilis | Denmark | SEQ ID NO: 15 |
| Rhizoctonia solani AG2-2IIIB | EMBL: PRJEB9381 | SEQ ID NO: 45 |

TABLE 2

| Strain | Strain no. | Source country | Mature protein SEQ ID |
|---|---|---|---|
| Rhizoctonia solani 1135 | CBS213.84 | Unknown | SEQ ID NO: 39 |
| Rhizoctonia solani 1135 | CBS213.84 | Unknown | SEQ ID NO: 36 |
| Cercospora fusimaculans | IMI167426 | Australia | SEQ ID NO: 9 |

CBS = CBS-KNAW Fungal Biodiversity Centre, Utrecht, The Netherlands
IMI = International Mycological Institute, now part of The Centre for Biosciences and Agriculture International, Wallingford, Oxfordshire, England.

Chromosomal DNA was isolated from the strains and the full genome of each strain was sequenced, assembled and annotated by standard methods known to the person skilled in the art, or by purchasing the services commercially. Public genomes were downloaded with annotations or as assembled whole genome sequences and annotated by standard methods known to the person skilled in the art. The annotated genomes were searched for predicted peptides with the NUC1_A domain, and 17 putative DNases were identified. The genes encoding these putative DNases were cloned into an *Aspergillus* expression vector either by using PCR to amplify the DNase gene from genomic DNA or by purchasing a custom synthesized gene encoding the DNase. The cloning method used for each DNase is given in table 3 below.

TABLE 3

| Source strain | Mature protein SEQ ID |
|---|---|
| *Rhizoctonia solani* 123E | SEQ ID NO: 48 |
| *Rhizoctonia solani* | SEQ ID NO: 33 |
| *Marasmius oreades* | SEQ ID NO: 6 |
| *Physisporinus sanguinolentus* | SEQ ID NO: 18 |
| *Irpex lacteus* | SEQ ID NO: 27 |
| *Pholiota squarrosa* | SEQ ID NO: 3 |
| *Cladosporium cladosporioides* | SEQ ID NO: 24 |
| *Deconica coprophila* | SEQ ID NO: 12 |
| *Phlebia subochracea* | SEQ ID NO: 30 |
| *Rhizoctonia solani* AG-1 IB | SEQ ID NO: 51 |
| *Rhizoctonia solani* AG-1 IA | SEQ ID NO: 42 |
| *Stropharia semiglobata* | SEQ ID NO: 21 |
| *Mortierella humilis* | SEQ ID NO: 15 |
| *Rhizoctonia solani* AG2-2IIIB | SEQ ID NO: 45 |
| *Rhizoctonia solani* 1135 | SEQ ID NO: 39 |
| *Rhizoctonia solani* 1135 | SEQ ID NO: 36 |
| *Cercospora fusimaculans* | SEQ ID NO: 9 |

*Aspergillus* expression vector pMStr57 is described in WO04/032648 and pDAu222 is described in WO13/024021. DNases cloned by PCR were amplified from genomic DNA with gene-specific primers that also append a Kozak translation initiation sequence "TCACC" immediately 5' of the start codon and cloned into BamHI and XhoI digested pMStr57. DNases cloned by synthesis were reverse translated with a method that preferentially utilizes codons that are used frequently in *Aspergillus oryzae*, and analyzes the resulting DNA sequences with algorithms designed to identify and remove sequence features that might hinder cloning or expression (WO06/066595). These DNase encoding genes were purchased as custom syntheses cloned into the BamHI and HindIII of pDAu222 from Thermo Fisher Scientific/GeneArt, Regensburg, Germany. The cloned NUC1_A encoding genes were sequenced and confirmed to be identical with the corresponding genes found in the genome sequences, and transformed into the *Aspergillus oryzae* strain MT3568 (WO11/057140) by the methods described in Christensen et al., 1988, *Biotechnology* 6, 1419-1422 and WO04/032648. Transformants were selected during regeneration from protoplasts based on the ability to utilize acetamide as a nitrogen source conferred by a selectable marker in the expression vectors, and were subsequently re-isolated under selection. Production of the recombinant DNases was evaluated by culturing the transformants in 96-well deep-well microtiter plates for 4 days at 30° C. in YPG medium (WO 05/066338) and monitoring DNase expression by SDS-PAGE. For larger-scale production of the recombinant DNases, select transformants were cultured in 500 ml baffled flasks containing 150 ml of either YPG medium or DAP-4C-1 medium (WO12/103350). The cultures were shaken on a rotary table at 150 RPM at for 4 days. The culture broth was subsequently separated from cellular material by passage through a 0.22 um filtration unit.

Example 2: Chromatographic Purification of Recombinant DNases pH of the filtered sample was adjusted to around pH 7.5 and 1.8M ammonium sulfate was added. The sample was applied to a 5 ml HiTrap™ Phenyl (HS) column on an Akta Explorer. Prior to loading, the column had been equilibrated in 5 column volumes (CV) of 50 mM HEPES+1.8M AMS pH 7. In order to remove unbound material, the column was washed with 5 CV of 50 mM HEPES+1.8M AMS pH 7. The target protein was eluted from the column into a 10 ml loop using 50 mM HEPES+20% isopropanol pH 7. From the loop, the sample was loaded onto a desalting column (HiPrep™ 26/10 Desalting), which had been equilibrated with 3CV of 50 mM HEPES+100 mM NaCl pH 7.0. The target protein was eluted with 50 mM HEPES+100 mM NaCl pH 7.0 and relevant fractions were selected and pooled based on the chromatogram. The flow rate was 5 ml/min.

Protein concentration in the final sample was estimated by measuring absorption at 280 nm.

Example 3: Wash Data

Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Darmstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

Swatches with biofilm of *Brevundimonas* sp. and *Micrococcus luteus* were included in the present study. Bacteria was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, cells were pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600\,nm}$ of 0.03, and 20 mL was added into a petridish (diameter 9 mm), in which a swatch (50 mm×50 mm) of either sterile cotton (WFK1A), Polyester-cotton (WFK20A) or polyester (WFK30A) was placed. After incubation (48 h at 15° C. with shaking (100 rpm), swatches were rinsed twice with 0.9% (w/v) NaCl.

Wash Experiment

Wash liquor of liquid Ariel color & style was prepared by weighing out and dissolving detergents in water with water hardness 15° dH. (Pigmentschmutz, 09V, wfk, Krefeld, Germany) (0.7 g/L) was added to the wash liquor, and 1000 ml was added to each TOM beaker. Two rinsed WFK10A swatches with *Brevundimonas* sp. biofilm, two rinsed WFK20A swatches with *Brevundimonas* sp. biofilm, two rinsed WFK30A swatches with *Brevundimonas* sp. biofilm, two rinsed WFK10A swatches with *Micrococcus luteus* biofilm, two rinsed WFK20A swatches with *Micrococcus luteus* biofilm, two rinsed WFK30A swatches with *Micrococcus luteus* biofilm, two sterile WFK10A swatches, two sterile WFK20A swatches and two sterile WFK30A swatches were added and washed for 35 min at 30° C. In washes, where DNase was included, DNase was dosed 0.2, 0.02 or 0.002 ppm to the wash liquor. After wash, all swatches were rinsed twice in tap water and dried on filter paper over night. Color difference (L values) was measured using a Color Eye (Macbeth Color Eye 7000 reflectance spectrophotometer). The measurements were made without UV in the incident light and the L value from the CIE Lab color space was extracted.

The color difference (L value, L*) represents the darkest black at L*=0, and the brightest white at L*=100. Data is represented as Delta L values meaning the L value of the swatch washed with DNase minus the L value of swatch washed without DNase.

TABLE 4

Deep-cleaning of *Rhizoctonia solani* (SEQ ID NO 45) DNase *Brevundimonas* sp. Biofilm.

| Textile | Remission | | | ΔRemission | | |
|---|---|---|---|---|---|---|
| | 10A | 20A | 30A | 10A | 20A | 30A |
| DNase 0 | 64 | 66 | 66 | | | |
| DNase 0.2 ppm | 66 | 68 | 67 | 3 | 2 | 2 |
| DNase 0.02 ppm | 65 | 68 | 68 | 2 | 2 | 3 |
| DNase 0.002 ppm | 67 | 69 | 69 | 3 | 3 | 3 |

Tabel 5

Deep-cleaning of *Rhizoctonia solani* (SEQ ID NO 45) DNase *Micrococcus luteus* biofilm.

| Textile | Remission | | | ΔRemission | | |
|---|---|---|---|---|---|---|
| | 10A | 20A | 30A | 10A | 20A | 30A |
| DNase 0 | 64 | 64 | 61 | | | |
| DNase 0.2 ppm | 68 | 69 | 64 | 4 | 5 | 3 |
| DNase 0.02 ppm | 68 | 69 | 68 | 4 | 4 | 7 |
| DNase 0.002 ppm | 69 | 69 | 69 | 4 | 5 | 8 |

TABLE 6

Soil inhibition transfer of *Rhizoctonia solani* DNAse Sterile swatches (no biofilm).

| Textile | Remission | | | ΔRemission | | |
|---|---|---|---|---|---|---|
| | 10A | 20A | 30A | 10A | 20A | 30A |
| DNase 0 | 64 | 66 | 63 | | | |
| DNase 0.2 ppm | 68 | 70 | 71 | 4 | 4 | 8 |
| DNase 0.02 ppm | 67 | 70 | 70 | 3 | 4 | 7 |
| DNase 0.002 ppm | 68 | 71 | 71 | 5 | 6 | 8 |

Example 4: Deep Cleaning Effect of DNases

Preparation of Biofilm Swatches

Biofilm swatches were made by growing *Brevundimonas* sp. on polyester swatches for two days. The biofilm swatches were rinsed twice in water and dried for 1 h under a flow and subsequently punched into small circles and stored at 4° C. for further use.

Washing Experiment

Biofilm swatches punctures were placed in a deep well 96 format plate. The 96 well plate was placed in a Hamilton robot and subjected to a wash simulation program using the following conditions: Shaking speed: 30 sec at 1000 rpm. Duration of wash cycle: 30 minutes with shaking; temperature 30° C.; Volume of wash liquor (total): 0.5 ml per well. (490 wash liquor+10 uL sample). For screening of wash performance of WT DNAses, Model detergent A (3.3 g/L) dissolved in water hardness 15° dH was used.

Model detergent A wash liquor (100%) was prepared by dissolving 3.33 g/l of model detergent A containing 12% LAS, 11% AEO Biosoft N25-7 (NI), 5% AEOS (SLES), 6% MPG (mono propylene glycol), 3% ethanol, 3% TEA (triethanolamine), 2.75% cocoa soap, 2.75% soya soap, 2% glycerol, 2% sodium hydroxide, 2% sodium citrate, 1% sodium formiate, 0.2% DTMPA and 0.2% PCA (Propenoic acid=acrylic maleic copolymer)(all percentages are w/w (weight volume) in water with hardness 15 dH.

Soil was subsequently added to reach a concentration of 0.7 g soil/L (WFK 09V pigment soil). A 96 well plate was filled with each enzyme sample, and the program was started on the robot. DNAses were tested in concentration 0.5-0.05 ppm. The blank consisted of biofilm swatches without any enzyme addition. After completion of the wash simulation cycle, the swatch punctures were removed from the wash liquor and dried on a filter paper. The dried swatch punctures were fixed on a sheet of white paper for scanning. The scanned picture was further used with the software color-analyzer. Each sample will have an intensity measurement from the color analyzer software analysis, that will be used to calculate the delta intensity (remission), by subtracting the intensity of the blank, without enzyme. Values over 70 are visual for the human eye.

TABLE 7

Wash performance of DNAses.

| Name | Intensity (with DNAse) | Intensity (without DNAse) | Delta Intensity |
|---|---|---|---|
| SEQ ID NO: 39 *Rhizoctonia solani* | 380 | 288 | 92 |
| SEQ ID NO: 30 *Phlebia subochracea* | 371 | 288 | 83 |
| SEQ ID NO: 36 *Rhizoctonia solani* | 376 | 288 | 88 |

TABLE 7-continued

Wash performance of DNAses.

| Name | Intensity (with DNAse) | Intensity (without DNAse) | Delta Intensity |
|---|---|---|---|
| SEQ ID NO: 51 Rhizoctonia solani AG-1 IB | 377 | 288 | 89 |
| SEQ ID NO: 42 Rhizoctonia solani AG-1 IA | 379 | 288 | 91 |
| SEQ ID NO: 21 Stropharia semiglobata | 371 | 288 | 83 |
| SEQ ID NO: 15 Mortierella humilis | 372 | 288 | 84 |
| SEQ ID NO: 18 Physisporinus sanguinolentus | 354 | 258 | 97 |
| SEQ ID NO: 24 Cladosporium cladosporioides | 352 | 258 | 94 |
| SEQ ID NO: 6 Marasmius oreades | 349 | 258 | 92 |
| SEQ ID NO: 12 Deconica coprophila | 346 | 258 | 88 |
| SEQ ID NO: 27 Irpex lacteus | 345 | 258 | 87 |
| SEQ ID NO: 3 Pholiota squarrosa | 344 | 258 | 86 |
| SEQ ID NO: 48 Rhizoctonia solani 123E | 334 | 258 | 76 |
| SEQ ID NO: 45 Rhizoctonia solani | 384 | 285 | 99 |
| SEQ ID NO: 33 Rhizoctonia solani | 333 | 258 | 75 |

Example 5: Wash Performance of DNase from *R. solani* with Sulfite

The wash performance of a DNase of the invention from *Rhizoctonia solani* (SEQ ID NO: 45) was tested with and without sulfite.

Preparation of Biofilm Swatches

*Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectrophotometer (POLARstar Omega (BMG Labtech, Ortenberg, Germany). Fresh TSB diluted twice with water was inoculated to an $OD_{600\ nm}$ of 0.03, and 20 mL was added to a Petri dish, in which a swatch (8×12 cm) of sterile Polyester WFK30A was placed. After incubation (48 h at 15° C. with shaking (100 rpm), swatches were rinsed twice with 0.9% (w/v) NaCl.

Automatic Mechanical Stress Assay (AMSA) for Laundry

To assess wash performance in laundry, washing experiments were performed using the Automatic Mechanical Stress Assay (AMSA). With the AMSA, wash performance of a large quantity of small volume enzyme-detergent solutions can be examined. The AMSA plate has slots for test solutions and a lid firmly squeezing the textile sample, and thus the textile sample is washed against all the slot openings. During washing, the plate, test solutions, textile and lid are vigorously shaken to bring the test solution in contact with the textile and apply mechanical stress in a regular, periodic oscillating manner. For further description see WO 02/42740, especially the paragraph "Special method embodiments" at pages 23-24.

Washing experiments were conducted under the experimental conditions specified below:

| Detergent | Tide Pod White Phase |
|---|---|
| Detergent dosage | 1 g/L |
| pH | As is |
| Wash time | 20 minutes |
| Temperature | 30° C. |

-continued

| Detergent | Tide Pod White Phase |
|---|---|
| Water hardness | 6° dH $Ca^{2+}/Mg^{2+}/NaHCO_3$ 2:1:4.5 |
| Addition of Potassium Sulfite ($K_2SO_3$ (90%) Sigma Aldrich 658510) | 0%-0.4% (4.4 g/l) |
| Addition of Carbon Black to Detergent Solution | 0.7 g/L Pigment soil 09V obtained from WFK Testgewebe GmbH, Christenfeld 10, D-41379 Brüggen, Germany. |
| Enzyme dosage | 0.001-0.002-0.005-0.01 ppm |
| Test material | *Brevundimonas* Polyester Biofilm swatch |

After washing the textiles were flushed in tap water and dried.

The wash performance is measured as the brightness of the colour of the washed textile. Brightness can also be expressed as the intensity of the light reflected from the sample when illuminated with white light. When the sample is stained the intensity of the reflected light is lower than that of a clean sample. Therefore, the intensity of the reflected light can be used to measure wash performance.

Color measurements are made with a professional flatbed scanner (Epson Expression 10000 XL), which is used to capture an image of the washed textile. To calculate the value for the light intensity from the scanned images, values from the image are converted into values for red, green and blue (RGB). The intensity value (Int) is calculated by adding the RGB values together as vectors and then taking the length of the resulting vector:

$$Int = \sqrt{r^2 + g^2 + b^2}$$

The improvement of the wash performance of the DNase from *R. solani* is expressed as a sum of the delta intensities at the four tested wash concentrations relative to the wash performance of a prior art DNase (SEQ ID NO: 21 from WO 2017/060475).

The results show that the DNase from *R. solani* has a better performance on the biofilm stain than the prior art DNase in the presence of sulfite. Most interestingly, *R. solani* DNase has a substantially improved performance in the presence of potassium sulfite (0.4%, w/v) in the same detergent.

Tables 8a, 8b, 8c and 8d below show how detergent containing the *R. solani* DNase results in improved wash performance in the presence of potassium sulfite. Table 8a shows the measured intensities, without sulfite, with the prior art DNase or the *R. solani* DNase at the four different enzyme concentrations. Table 8b shows the delta intensity (intensity with the *R. solani* DNase minus intensity with the prior art DNase as shown in Table 8a) at the four different enzyme concentrations without sulfite. Table 8c shows the measured intensities, with sulfite, with the prior art DNase or the *R. solani* DNase at the four different enzyme concentrations. Table 8d shows the delta intensity (intensity with the *R. solani* DNase minus intensity with the prior art DNase as shown in Table 8c) at the four different enzyme concentrations with sulfite. Tables 8b and 8d thus show the sum of the delta intensities without and with sulfite, respectively.

TABLE 8a

Tide Pod White Phase – no sulfite Intensity

|  | 0.001 ppm | 0.002 ppm | 0.005 ppm | 0.01 ppm |
|---|---|---|---|---|
| Prior art DNase | 374 | 375 | 373 | 376 |
| R. solani DNase | 374 | 377 | 375 | 377 |

TABLE 8b

| | Tide Pod White Phase – no sulfite Delta Intensity (minus "prior art") | | | | SUM of "Delta intensity" |
|---|---|---|---|---|---|
| | 0.001 ppm | 0.002 ppm | 0.005 ppm | 0.01 ppm | (minus "prior art") of 4 concentrations |
| Prior art DNase | 0 | 0 | 0 | 0 | |
| R. solani DNase | 0.6 | 2.1 | 2.0 | 1.1 | 5.8 |

TABLE 8c

Tide Pod White Phase + 0.4% Potassium Sulfite Intensity

|  | 0.001 ppm | 0.002 ppm | 0.005 ppm | 0.01 ppm |
|---|---|---|---|---|
| Prior art DNase | 364 | 367 | 367 | 372 |
| R. solani DNase | 366 | 369 | 372 | 372 |

TABLE 8d

| | Tide Pod White Phase + 0.4% Potassium Sulfite Delta Intensity (minus "prior art") | | | | SUM of "Delta intensity" |
|---|---|---|---|---|---|
| | 0.001 ppm | 0.002 ppm | 0.005 ppm | 0.01 ppm | (minus "prior art") of 4 concentrations |
| Prior art DNase | 0 | 0 | 0 | 0 | |
| R. solani DNase | 2.2 | 1.8 | 4.9 | 0.6 | 9.5 |

The results above show that the sum of the delta intensities with the R. solani DNase in the presence of 0.4% potassium sulfite was 9.5, whereas the corresponding sum in the absence of sulfite was only 5.8. Surprisingly, and in contrast to what is observed with most DNases, the R. solani DNase with SEQ ID NO: 45 was thus found to have an improved wash performance in the presence of sulfite compared to the wash performance under the same conditions without sulfite.

Example 6: Construction of Phylogenetic Trees

The NUC1 domain includes the polypeptides of the invention having DNase activity and comprises the NUC1_A domain as well as the clusters such as the clades. A phylogenetic tree was constructed, of polypeptide sequences containing a DUF1524 domain, as defined in PFAM (PF07510, Pfam version 30.0 Finn (2016). Nucleic Acids Research, Database Issue 44:D279-D285). The phylogenetic tree was constructed from a multiple alignment of mature polypeptide sequences containing at least one DUF1524 domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128). The polypeptide comprises of the DUF1524 domain comprises several motifs one example is [E/D/H]H[I/V/V/F/M]X[P/A/S] (SEQ ID NO 52) situated in positions corresponding to positions 101 to 105 in R. solani (SEQ ID NO 45). H102 is a catalytic residue involved in the catalytic activity of DUF1524, and part of the HXXP motif.

The polypeptides in DUF1524 can be separated into distinct sub-clusters. The sub-clusters are defined by one or more short sequence motifs, as well as by containing a DUF1524 domain as defined in PFAM (PF07510, Pfam version 30.0). We denoted one sub-cluster comprising the motif [F/L/Y/I]A[N/R]D[L/I/P/V] (SEQ ID NO 53), corresponding to positions 125 to 129 in SEQ ID NO: 45 as family NUC1. Another motif characteristic of this domain is C[DIN]T[A/R](SEQ ID NO 54), corresponding to position 56 to 59 in SEQ ID NO 45. All polypeptide sequences containing a DUF1524 as well as the two motifs will be denoted as containing a NUC1 domain.

Generation of NUC1 a Domain

A phylogenetic tree was constructed of polypeptide sequences containing a NUC1 domain as defined above. The phylogenetic tree was constructed from a multiple alignment of mature polypeptide sequences containing at least one NUC1 domain. The sequences were aligned using the MUSCLE algorithm version 3.8.31 (Edgar, 2004. *Nucleic Acids Research* 32(5): 1792-1797), and the tree was constructed using FastTree version 2.1.8 (Price et al., 2010, *PloS one* 5(3)) and visualized using iTOL (Letunic & Bork, 2007. *Bioinformatics* 23(1): 127-128). The polypeptides in NUC1 can be separated into at least distinct sub-clusters, one of which is denoted NUC1_A. A characteristic motif for this subgroup is the motif [DQ][IV]D[H] (SEQ ID NO 55) corresponding to amino acid 99 to 102 in the reference polypeptide (SEQ ID NO 45). The D at the position corresponding to position 101 of SEQ ID NO 45 is predicted to be involved in binding of catalytic metal ion cofactor.

Generation of Phylogenetic Trees

A phylogenetic tree was constructed, of polypeptide sequences containing a DUF1524 domain, a NUC1 domain, and a NUC1_A domain, as defined above. The phylogenetic tree was constructed from a multiple alignment of mature polypeptide sequences containing at least one NUC1_A domain. The sequences were aligned using the MUSCLE algorithm version 3.8.31 (Edgar, 2004. *Nucleic Acids Research* 32(5): 1792-1797), and the tree was constructed using FastTree version 2.1.8 (Price et al., 2010, *PloS one* 5(3)) and visualized using iTOL (Letunic & Bork, 2007, *Bioinformatics* 23(1): 127-128). The polypeptides in NUC1_A can be separated into multiple distinct sub-clusters, or clades, where we denoted the clades listed below. The distinct motifs for each clade are described in details below.

Generation of KEAW Clade

The KEAW clade comprises polypeptides of fungal origin, containing a DUF1524 domain, a NUC1 domain, and a NUC1_A domain, and having DNase activity. The polypeptides of the clade comprise the motif example PL[KR]E[AG]W (SEQ ID NO: 56), corresponding to position 100 to 105 of SEQ ID NO 45, where P (corresponding to position 100 of SEQ ID NO 45) is fully conserved in KEAW clade. An alignment of the polypeptides of the invention comprised in the clade is shown in FIG. 1.

A phylogenetic tree of the KEAW clade is shown in FIG. 2.

Generation of RAWI Clade

The RAWI clade comprises polypeptides within the KEAW clade, containing a DUF1524 domain, a NUC1 domain, and a NUC1_A domain, having DNase activity, and belonging to fungal taxonomic order Cantharellales. The polypeptides of the clade comprise the motif example C[TK]Y[VI][RC][AS]WI (SEQ ID NO: 57), corresponding to position 162 to 168 in SEQ ID NO 45.

An alignment of the polypeptides of the invention comprised in the clade is shown in FIG. 3.

A phylogenetic tree of the RAWI clade is shown in FIG. 4.

The invention claimed is:

1. A composition comprising a polypeptide of the KEAW or the RAWI clade, a detergent adjunct ingredient, and a surfactant, wherein the polypeptide has DNase activity and is selected from the group consisting of:
   (a) a polypeptide having at least 80% sequence identity to the polypeptide of SEQ ID NO: 33;
   (b) a polypeptide having at least 80% sequence identity to the polypeptide of SEQ ID NO: 36;
   (c) a polypeptide having at least 80% sequence identity to the polypeptide of SEQ ID NO: 42;
   (d) a polypeptide having at least 80% sequence identity to the polypeptide of SEQ ID NO: 45;
   (e) a polypeptide comprising the polypeptide of (a) to (d) and a N-terminal and/or C-terminal His-tag and/or HQ-tag;
   (f) a polypeptide comprising the polypeptide of (a) to (e) and a N-terminal and/or C-terminal extension of between 1 and 10 amino acids; and
   (g) a fragment of the polypeptide of (a) to (d) having DNase activity and having at least 90% of the length of the mature polypeptide
   wherein the composition is a bar, a homogenous tablet, a tablet having two or more layers, a pouch having one or more compartments, a regular or compact powder, a granule, a paste, a gel, or a regular, compact or concentrated liquid.

2. The composition of claim 1, wherein the polypeptide has at least 85% sequence identity to the polypeptide of SEQ ID NO: 45.

3. The composition of claim 1, wherein the polypeptide has at least 90% sequence identity to the polypeptide of SEQ ID NO: 45.

4. The composition of claim 1, wherein the polypeptide has at least 95% sequence identity to the polypeptide of SEQ ID NO: 45.

5. The composition of claim 1, wherein the polypeptide has at least 97% sequence identity to the polypeptide of SEQ ID NO: 45.

6. The composition of claim 1, wherein the polypeptide is a variant of the polypeptide of SEQ ID NO: 45, wherein the variant has DNase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions.

7. The composition of claim 1, wherein the polypeptide is a fragment of the polypeptide of SEQ ID NO: 45, which has DNase activity and at least 90% of the length of SEQ ID NO: 45.

8. The composition of claim 1, wherein the polypeptide comprises one or both the motif(s) PL[KR]E[AG]W (SEQ ID NO:56) or C[TK]Y[VI][RC][AS]WI (SEQ ID NO: 57).

9. The composition of claim 1, wherein the polypeptide is SEQ ID NO: 45.

10. The composition of claim 1, wherein the detergent adjunct ingredient is a builder, flocculating aid, chelating agent, dye transfer inhibitor, enzyme, enzyme stabilizer, enzyme inhibitor, catalytic material, bleach activator, hydrogen peroxide, source of hydrogen peroxide, preformed peracid, polymeric agent, clay soil removal/anti-redeposition agent, brightener, suds suppressor, dye, perfume, structure elasticizing agent, fabric softener, carrier, hydrotrope, co-builder, fabric huing agent, anti-foaming agent, dispersant, processing aid, or pigment.

11. The composition of claim 1, wherein the polypeptide has at least 88% sequence identity to the polypeptide of SEQ ID NO: 33, 36, or 42.

12. The composition of claim 1, wherein the polypeptide has at least 95% sequence identity to the polypeptide of SEQ ID NO: 33, 36, or 42.

13. A method for laundering a textile, comprising:
(a) exposing the textile to a wash liquor comprising a composition of claim 1;
(b) completing at least one wash cycle; and
(c) optionally rinsing the textile.

14. A recombinant host cell comprising a polynucleotide encoding a polypeptide of the KEAW or the RAWI clade, wherein the polynucleotide is operably linked to one or more control sequences that direct the production of the polypeptide and is introduced into the host cell and wherein the polypeptide has DNase activity and is selected from the group consisting of:
(a) a polypeptide having at least 80% sequence identity to the polypeptide of SEQ ID NO: 33;
(b) a polypeptide having at least 80% sequence identity to the polypeptide of SEQ ID NO: 36;
(c) a polypeptide having at least 80% sequence identity to the polypeptide of SEQ ID NO: 42;
(d) a polypeptide having at least 80% sequence identity to the polypeptide of SEQ ID NO: 45;
(e) a polypeptide comprising the polypeptide of (a) to (d) and a N-terminal and/or C-terminal His-tag and/or HQ-tag;
(f) a polypeptide comprising the polypeptide of (a) to (e) and a N-terminal and/or C-terminal extension of between 1 and 10 amino acids; and
(g) a fragment of the polypeptide of (a) to (d) having DNase activity and having at least 90% of the length of the mature polypeptide.

15. A method of producing a polypeptide having DNase activity, comprising cultivating the host cell of claim 14 under conditions conducive for production of the polypeptide.

16. The method of claim 15, wherein the polypeptide has at least 85% sequence identity to the polypeptide of SEQ ID NO: 45.

17. The method of claim 15, wherein the polypeptide has at least 90% sequence identity to the polypeptide of SEQ ID NO: 45.

18. The method of claim 15, wherein the polypeptide has at least 95% sequence identity to the polypeptide of SEQ ID NO: 45.

19. The method of claim 15, wherein the polypeptide has at least 97% sequence identity to the polypeptide of SEQ ID NO: 45.

20. The method of claim 15, wherein the host cell is a *Bacillus* cell.

21. The method of claim 15, wherein the host cell is a yeast or filamentous fungal cell.

22. The method of claim 15, wherein the host cell is an *Aspergillus* or *Trichoderma* cell.

23. The method of claim 15, wherein the host cell comprises multiple copies of the polynucleotide encoding the polypeptide.

24. The method of claim 15, wherein the polypeptide has at least 88% sequence identity to the polypeptide of SEQ ID NO: 33, 36, or 42.

25. The method of claim 15, wherein the polypeptide has at least 95% sequence identity to the polypeptide of SEQ ID NO: 33, 36, or 42.

* * * * *